United States Patent
Edmunds et al.

(10) Patent No.: US 10,961,248 B2
(45) Date of Patent: Mar. 30, 2021

(54) PESTICIDALLY ACTIVE HETEROCYCLIC DERIVATIVES WITH SULFUR CONTAINING SUBSTITUENTS

(71) Applicant: SYNGENTA PARTICIPATIONS AG, Basel (CH)

(72) Inventors: Andrew Edmunds, Stein (CH); Michel Muehlebach, Stein (CH); Pierre Joseph Marcel Jung, Stein (CH); Sebastian Rendler, Stein (CH); Vikas Sikervar, Goa (IN); Girish Rawal, Goa (IN); Indira Sen, Goa (IN); Régis Jean Georges Mondiere, Stein (CH); Tomas Smejkal, Stein (CH); Myriem El Qacemi, Stein (CH); Denis Gribkov, Stein (CH)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

(21) Appl. No.: 16/465,014

(22) PCT Filed: Nov. 24, 2017

(86) PCT No.: PCT/EP2017/080295
§ 371 (c)(1),
(2) Date: May 29, 2019

(87) PCT Pub. No.: WO2018/099812
PCT Pub. Date: Jun. 7, 2018

(65) Prior Publication Data
US 2019/0322675 A1  Oct. 24, 2019

(30) Foreign Application Priority Data

Dec. 1, 2016 (IN) .............................. 201611041146
Mar. 28, 2017 (IN) .............................. 201711010969

(51) Int. Cl.
| | | |
|---|---|---|
| C07D 487/04 | (2006.01) |
| C07D 471/04 | (2006.01) |
| A01N 43/90 | (2006.01) |
| C07D 487/02 | (2006.01) |
| C07D 471/02 | (2006.01) |
| C07C 211/21 | (2006.01) |
| C07C 211/25 | (2006.01) |
| C07C 211/40 | (2006.01) |
| C07C 225/14 | (2006.01) |

(52) U.S. Cl.
CPC .......... *C07D 487/04* (2013.01); *A01N 43/90* (2013.01); *C07D 471/04* (2013.01)

(58) Field of Classification Search
None
See application file for complete search history.

(56) References Cited

FOREIGN PATENT DOCUMENTS

| | | |
|---|---|---|
| EP | 2 862 853 A1 | 4/2015 |
| EP | 3 018 130 A1 | 5/2016 |
| WO | 2015000715 A1 | 1/2015 |
| WO | 2017084879 A1 | 5/2017 |

OTHER PUBLICATIONS

Dorokhov et al: "Alkyl 3-aminoo-5-aryl-2-benzoyl-5-oxo-2-pentenoates as new chelating ligands and reagents of heterocyclic synthesis"; Russian Chemical Bulletin 52(9), pp. 2057-2062.
International Search Report for International Application No. PCT/EP2017/080295 dated Mar. 19, 2018.

*Primary Examiner* — Alton N Pryor
(74) *Attorney, Agent, or Firm* — Bakerhostetler; Toni-Junell Herbert

(57) ABSTRACT

Compounds of formula (I), wherein the substituents are as defined in claim 1, and the agrochemically acceptable salts, stereoisomers, enantiomers, tautomers and N-oxides of those compounds, can be used as insecticides and can be prepared in a manner known per se.

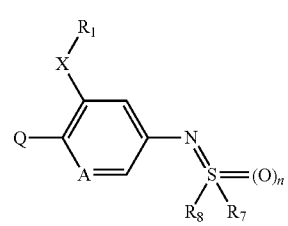

22 Claims, No Drawings

PESTICIDALLY ACTIVE HETEROCYCLIC DERIVATIVES WITH SULFUR CONTAINING SUBSTITUENTS

CROSS-REFERENCE TO RELATED APPLICATIONS

This application is a 371 National Stage application of International Application No. PCT/EP2017/080295, filed Nov. 24, 2017, which claims priority European Patent Application Nos. 201611041146, filed Dec. 1, 2016, and 201711010969, filed Mar. 28, 2017, the entire contents of which applications are hereby incorporated by reference.

The present invention relates to pesticidally active, in particular insecticidally active heterocyclic derivatives containing sulfur substituents, to processes for their preparation, to compositions comprising those compounds, and to their use for controlling animal pests, including arthropods and in particular insects or representatives of the order *Acarina*.

Heterocyclic compounds with pesticidal action are known and described, for example, in WO 2015/002211, WO 2015/121136 and WO 2016/124557. There have now been found novel pesticidally active heterocyclic sulfilimine and sulfoximine derivatives with sulfur containing phenyl and pyridyl substituents.

The present invention accordingly relates to compounds of formula I,

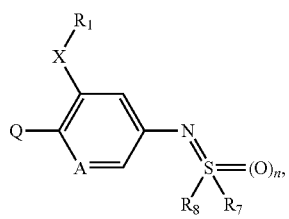

(I)

wherein
A is CH or N;
X is S, SO or $SO_2$;
$R_1$ is $C_1$-$C_4$alkyl, $C_1$-$C_4$haloalkyl or $C_3$-$C_6$cycloalkyl-$C_1$-$C_4$alkyl;
$R_7$ and $R_8$ are, independently from each other, $C_1$-$C_6$alkyl, $C_1$-$C_6$haloalkyl, $C_3$-$C_6$cycloalkyl, $C_1$-$C_6$cyanoalkyl, $C_1$-$C_4$alkoxy$C_1$-$C_4$alkyl, pyridyl or phenyl, wherein said pyridyl or phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or $R_7$ and $R_8$, together with the sulfur atom to which they are attached, form a four- to six-membered, saturated ring system, said ring system can be mono- or polysubstituted by substituents selected from the group consisting of halogen, cyano, $C_1$-$C_4$alkyl, $C_1$-$C_4$alkoxy and $C_1$-$C_4$haloalkyl; and said ring system may contain one heteroatom selected from the group consisting of nitrogen, oxygen and sulfur;

n is 0 or 1;

Q is a radical selected from the group consisting of formula $Q_1$ to $Q_3$

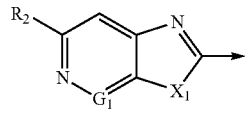

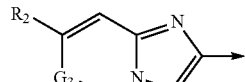

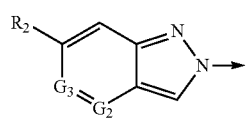

wherein the arrow denotes the point of attachment to the ring incorporating the radical A;
and wherein
$X_1$ is O, S or $NR_3$, wherein $R_3$ is $C_1$-$C_4$alkyl;
$R_2$ is halogen, $C_1$-$C_6$haloalkyl, $C_1$-$C_4$haloalkylsulfanyl, $C_1$-$C_4$haloalkylsulfinyl, $C_1$-$C_4$haloalkylsulfonyl or $C_1$-$C_6$haloalkoxy;
$G_1$ is N or CH;
$G_2$ and $G_3$ are, independently from each other, N or CH; and agrochemically acceptable salts, stereoisomers, enantiomers, tautomers and N-oxides of the compounds of formula I.

Compounds of formula I which have at least one basic centre can form, for example, acid addition salts, for example with strong inorganic acids such as mineral acids, for example perchloric acid, sulfuric acid, nitric acid, nitrose acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, nonyl, decyl and their branched isomers. Alkylsulfanyl, alkylsulfinyl, alkylsulfonyl, alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

Alkoxy groups preferably have a preferred chain length of from 1 to 6 carbon atoms. Alkoxy is, for example, methoxy, ethoxy, propoxy, i-propoxy, n-butoxy, isobutoxy, sec-butoxy and tert-butoxy and also the isomeric pentyloxy and hexyloxy radicals; preferably methoxy and ethoxy.

Alkoxyalkyl groups preferably have a chain length of 1 to 6 carbon atoms, more preferably a chain length of 1 to 4 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkylsulfanyl is for example methylsulfanyl, ethylsulfanyl, propylsulfanyl, isopropylsulfanyl, butylsulfanyl, pentylsulfanyl, and hexylsulfanyl.

Alkylsulfinyl is for example methylsulfinyl, ethylsulfinyl, propylsulfinyl, isopropylsulfinyl, a butylsulfinyl, pentylsulfinyl, and hexylsulfinyl.

Alkylsulfonyl is for example methylsulfonyl, ethylsulfonyl, propylsulfonyl, isopropylsulfonyl, butylsulfonyl, pentylsulfonyl, and hexylsulfonyl.

The cycloalkyl groups preferably have from 3 to 6 ring carbon atoms, for example cyclopropyl, cyclobutyl, cyclopentyl and cyclohexyl.

Haloalkoxy groups preferably have a chain length of from 1 to 4 carbon atoms. Haloalkoxy is, for example, difluoromethoxy, trifluoromethoxy or 2,2,2-trifluoroethoxy.

Haloalkylsulfanyl groups preferably have a chain length of from 1 to 4 carbon atoms. Haloalkylsulfanyl is, for example, difluoromethylsulfanyl, trifluoromethylsulfanyl or 2,2,2-trifluoroethylsulfanyl. Similar considerations apply to the radicals $C_1$-$C_4$haloalkylsulfinyl and $C_1$-$C_4$haloalkylsulfonyl, which may be, for example, trifluoromethylsulfinyl, trifluoromethylsulfonyl or 2,2,2-trifluoroethylsulfonyl.

In the context of this invention "mono- to polysubstituted" in the definition of the substituents, means typically, depending on the chemical structure of the substituents, monosubstituted to four-times substituted, preferably monosubstituted to three-times substituted, more preferably mono-, or double-substituted.

Free radicals represents methyl groups.

The compounds of formula I according to the invention also include hydrates which may be formed during the salt formation.

Preferably $R_7$ and $R_8$ are, independently from each other, $C_1$-$C_6$alkyl, $C_1$-$C_6$haloalkyl, $C_3$-$C_6$cycloalkyl, pyridyl or phenyl, wherein said pyridyl or phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or $R_7$ and $R_8$, together with the sulfur atom to which they are attached, form a four- to six-membered, saturated ring system, said ring system can be mono- or polysubstituted by substituents selected from the group consisting of halogen, cyano, $C_1$-$C_4$alkyl and $C_1$-$C_4$haloalkyl; and said ring system may contain one heteroatom selected from the group consisting of nitrogen, oxygen and sulfur.

A preferred group of compounds of formula I is represented by the compounds of formula I-1

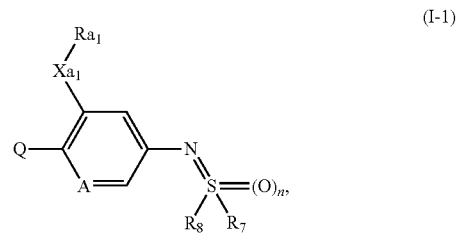

wherein Q, A, n, $R_7$ and $R_8$ are as defined under formula I above; and wherein $Xa_1$ is S, SO or $SO_2$;

$Ra_1$ is methyl, ethyl, n-propyl, i-propyl or cyclopropylmethyl.

In said preferred group of compounds of formula I-1, A is preferably N, $Xa_1$ is preferably S or $SO_2$, more preferably $SO_2$, and $Ra_1$ is preferably ethyl. In a further preferred group of compounds of formula I-1, A is preferably CH, $Xa_1$ is preferably S or $SO_2$, more preferably $SO_2$, and $Ra_1$ is preferably ethyl.

In another preferred group of compounds of formula I-1, n is 0 or 1, in particular n is preferably 1, and $R_7$ and $R_8$ are, independently from each other, $C_1$-$C_6$alkyl, $C_3$-$C_6$ cycloalkyl or phenyl monosubstituted by $C_1$-$C_4$alkyl, even more preferably methyl, ethyl, cyclopropyl or phenyl substituted by methyl (preferably in the 4-position); in particular $R_7$ and $R_8$ are, independently from each other, $C_1$-$C_6$alkyl or $C_3$-$C_6$cycloalkyl, even more preferably methyl or cyclopropyl.

In yet another preferred group of compounds of formula I-1, n is 0 or 1, preferably n is 1, and $R_7$ and $R_8$, together with the sulfur atom to which they are attached, form a four- to six-membered, saturated ring system, preferably said ring system is unsubstituted, and said ring system contains no or one oxygen atom.

A further preferred embodiment of said especially preferred groups of compounds of formula I-1 comprises compounds wherein A is N or CH, in particular A is preferably N; $Xa_1$ is preferably $SO_2$; $Ra_1$ is preferably ethyl; n is 0 or 1, in particular n is preferably 1; and $R_7$ and $R_8$ are, independently from each other, $C_1$-$C_6$alkyl, $C_3$-$C_6$ cycloalkyl or phenyl monosubstituted by $C_1$-$C_4$alkyl, even more preferably methyl, ethyl, cyclopropyl or phenyl substituted by methyl (preferably in the 4-position); in particular $C_1$-$C_6$alkyl or $C_3$-$C_6$cycloalkyl, even more preferably methyl or cyclopropyl; or $R_7$ and $R_8$, together with the sulfur atom to which they are attached, form a four- to six-membered, saturated ring system, preferably said ring system is unsubstituted, and said ring system contains no or one oxygen atom.

In compounds of formula I-1 and all of the preferred embodiments of compounds of formula I-1 mentioned above, Q is preferably selected from $Q_1$ to $Q_3$, in particular selected from $Q_1$ and $Q_2$, wherein $X_1$, $R_2$, $G_1$, $G_2$ and $G_3$ are as defined under formula I above. In said especially preferred group of compounds of formula I-1, $X_1$ is preferably $NR_3$, in which $R_3$ is $C_1$-$C_4$alkyl, more preferably methyl; $R_2$ is preferably $C_1$-$C_6$haloalkyl, more preferably trifluoromethyl; $G_1$ is CH or N, in particular $G_1$ is CH; $G_2$ is CH; and $G_3$ is N.

A further preferred group of compounds of formula I is represented by the compounds of formula I-2

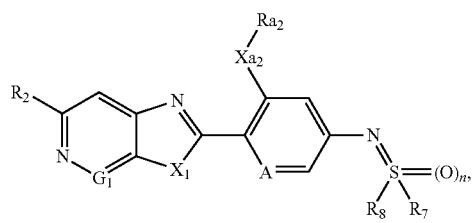

(I-2)

wherein $X_1$, $R_2$, $G_1$, A, n, $R_7$ and $R_8$ are as defined under formula I above; and wherein $Xa_2$ is S, SO or $SO_2$; $Ra_2$ is methyl, ethyl, n-propyl, i-propyl or cyclopropylmethyl.

In said preferred group of compounds of formula I-2, A is CH or N, in particular A is preferably N; $Xa_2$ is preferably S or $SO_2$, more preferably $SO_2$; and $Ra_2$ is preferably ethyl. In another preferred group of compounds of formula I-2, $X_1$ is preferably $NR_3$, in which $R_3$ is $C_1$-$C_4$alkyl, more preferably methyl; $R_2$ is preferably $C_1$-$C_6$haloalkyl, more preferably trifluoromethyl; and $G_1$ is CH or N, preferably CH.

In compounds of formula I-2 and all of the preferred embodiments of compounds of formula I-2 mentioned above, n is 0 or 1, in particular n is preferably 1; and $R_7$ and $R_8$ are as defined under formula I above. A further preferred embodiment of said especially preferred group of compounds of formula I-2 comprises compounds wherein $R_7$ and $R_8$ are, independently from each other, $C_1$-$C_6$alkyl, $C_3$-$C_6$cycloalkyl or phenyl monosubstituted by $C_1$-$C_4$alkyl, even more preferably methyl, ethyl, cyclopropyl or phenyl substituted by methyl (preferably in the 4-position); in particular $C_1$-$C_6$alkyl or $C_3$-$C_6$cycloalkyl, even more preferably methyl or cyclopropyl; or $R_7$ and $R_8$, together with the sulfur atom to which they are attached, form a four- to six-membered, saturated ring system, preferably said ring system is unsubstituted, and said ring system contains no or one oxygen atom.

Another preferred group of compounds of formula I is represented by the compounds of formula I-3

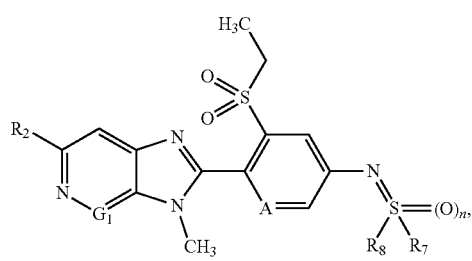

(I-3)

wherein
A is CH or N; in particular A is N;
$R_2$ is $C_1$-$C_6$haloalkyl, preferably trifluoromethyl;
$G_1$ is N or CH, preferably CH;
n is 0 or 1; in particular n is 1;
$R_7$ and $R_8$ are, independently from each other, $C_1$-$C_6$alkyl, $C_3$-$C_6$cycloalkyl or phenyl monosubstituted by $C_1$-$C_4$alkyl, preferably methyl, ethyl, cyclopropyl or phenyl substituted by methyl (preferably in the 4-position); in particular $C_1$-$C_6$alkyl or $C_3$-$C_6$cycloalkyl, preferably methyl or cyclopropyl; or $R_7$ and $R_8$, together with the sulfur atom to which they are attached, form a four- to six-membered, saturated ring system, preferably said ring system is unsubstituted, and said ring system can contain one oxygen atom.

Yet another preferred group of compounds of formula I is represented by the compounds of formula I-3a

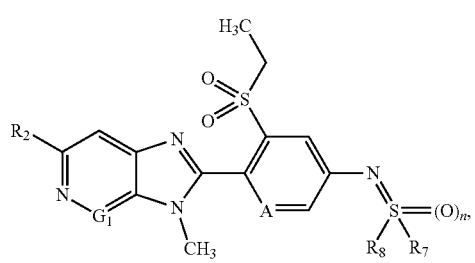

(I-3a)

wherein
A is CH or N;
$R_2$ is $C_1$-$C_6$haloalkyl, preferably trifluoromethyl;
$G_1$ is N or CH;
n is 0 or 1;
$R_7$ and $R_8$ are, independently from each other, $C_1$-$C_6$alkyl or $C_3$-$C_6$cycloalkyl, preferably methyl, ethyl or cyclopropyl; or $R_7$ and $R_8$, together with the sulfur atom to which they are attached, form a four- to six-membered, saturated ring system, preferably said ring system is unsubstituted, and said ring system can contain one oxygen atom.

Yet another preferred group of compounds of formula I is represented by the compounds of formula I-3b

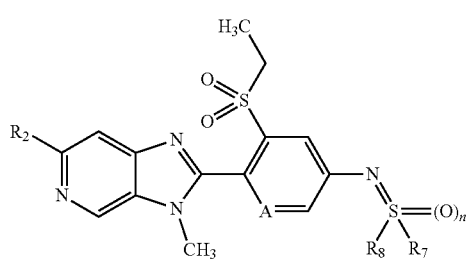

(I-3b)

wherein
A is CH or N;
$R_2$ is $C_1$-$C_6$haloalkyl, preferably trifluoromethyl;
n is 0 or 1;
$R_7$ and $R_8$ are, independently from each other, $C_1$-$C_6$alkyl or $C_3$-$C_6$cycloalkyl, preferably methyl, ethyl or cyclopropyl; or $R_7$ and $R_8$, together with the sulfur atom to which they are attached, form a four- to six-membered, saturated ring system, preferably said ring system is unsubstituted, and said ring system can contain one oxygen atom.

Yet another preferred group of compounds of formula I is represented by the compounds of formula I-3c

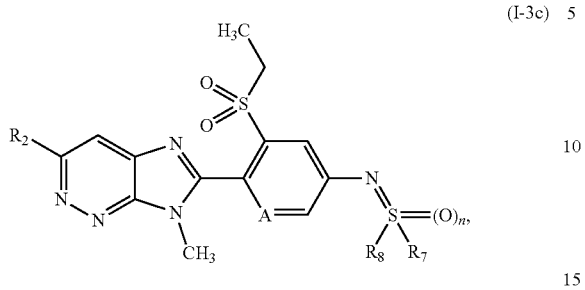

(I-3c)

wherein
A is CH or N;
R$_2$ is C$_1$-C$_6$haloalkyl, preferably trifluoromethyl;
n is 1;
R$_7$ and R$_8$ are, independently from each other, C$_1$-C$_6$alkyl or C$_3$-C$_6$cycloalkyl, preferably methyl, ethyl or cyclopropyl; or
R$_7$ and R$_8$, together with the sulfur atom to which they are attached, form a four- to six-membered, saturated ring system, preferably said ring system is unsubstituted, and said ring system can contain one oxygen atom.

A further preferred group of compounds of formula I is represented by the compounds of formula I-4

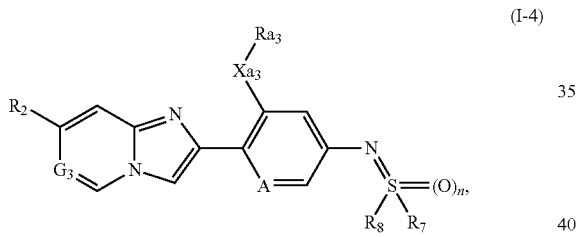

(I-4)

wherein R$_2$, G$_3$, A, n, R$_7$ and R$_8$ are as defined under formula I above; and wherein Xa$_3$ is S, SO or SO$_2$; Ra$_3$ is methyl, ethyl, n-propyl, i-propyl or cyclopropylmethyl.

In said preferred group of compounds of formula I-4, A is CH or N, in particular A is preferably N; Xa$_3$ is preferably S or SO$_2$, more preferably SO$_2$; and Ra$_3$ is preferably ethyl. In another preferred group of compounds of formula I-4, R$_2$ is preferably C$_1$-C$_6$haloalkyl, more preferably trifluoromethyl; and G$_3$ is CH or N, preferably N.

In compounds of formula I-4 and all of the preferred embodiments of compounds of formula I-4 mentioned above, n is 0 or 1, in particular preferably 1; and R$_7$ and R$_8$ are as defined under formula I above. A further preferred embodiment of said especially preferred group of compounds of formula I-4 comprises compounds wherein R$_7$ and R$_8$ are, independently from each other, C$_1$-C$_6$alkyl, C$_3$-C$_6$cycloalkyl or phenyl monosubstituted by C$_1$-C$_4$alkyl, even more preferably methyl, ethyl, cyclopropyl or phenyl substituted by methyl (preferably in the 4-position); in particular C$_1$-C$_6$alkyl or C$_3$-C$_6$cycloalkyl, even more preferably methyl or cyclopropyl; or R$_7$ and R$_8$, together with the sulfur atom to which they are attached, form a four- to six-membered, saturated ring system, preferably said ring system is unsubstituted, and said ring system contains no or one oxygen atom.

Another preferred group of compounds of formula I is represented by the compounds of formula I-5

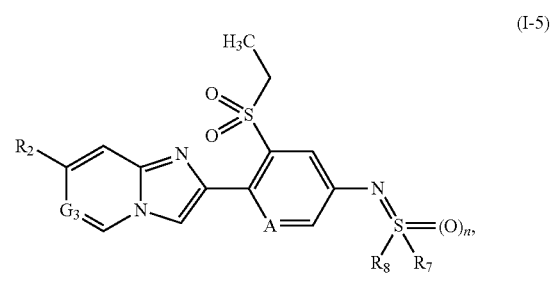

(I-5)

wherein
A is CH or N; in particular A is N;
R$_2$ is C$_1$-C$_6$haloalkyl, preferably trifluoromethyl;
G$_3$ is N or CH, preferably N;
n is 0 or 1; in particular n is 1;
R$_7$ and R$_8$ are, independently from each other, C$_1$-C$_6$alkyl, C$_3$-C$_6$cycloalkyl or phenyl monosubstituted by C$_1$-C$_4$alkyl, preferably methyl, ethyl, cyclopropyl or phenyl substituted by methyl (preferably in the 4-position); in particular C$_1$-C$_6$alkyl or C$_3$-C$_6$cycloalkyl, preferably methyl or cyclopropyl; or
R$_7$ and R$_8$, together with the sulfur atom to which they are attached, form a four- to six-membered, saturated ring system, preferably said ring system is unsubstituted, and said ring system can contain one oxygen atom.

Yet another preferred group of compounds of formula I is represented by the compounds of formula I-5a

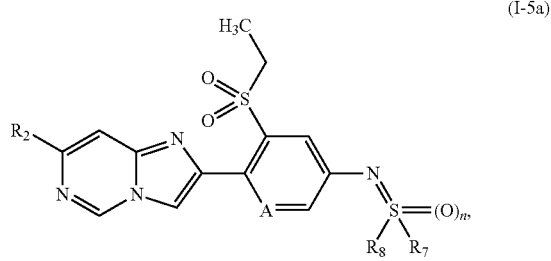

(I-5a)

wherein
A is CH or N;
R$_2$ is C$_1$-C$_6$haloalkyl, preferably trifluoromethyl;
n is 1;
R$_7$ and R$_8$ are, independently from each other, C$_1$-C$_6$alkyl, C$_3$-C$_6$cycloalkyl or phenyl monosubstituted by C$_1$-C$_4$alkyl, preferably methyl, ethyl, cyclopropyl or phenyl substituted by methyl (preferably in the 4-position); or
R$_7$ and R$_8$, together with the sulfur atom to which they are attached, form a four- to six-membered, saturated ring system, preferably said ring system is unsubstituted, and said ring system can contain one oxygen atom.

A further preferred group of compounds of formula I is represented by the compounds of formula I-7

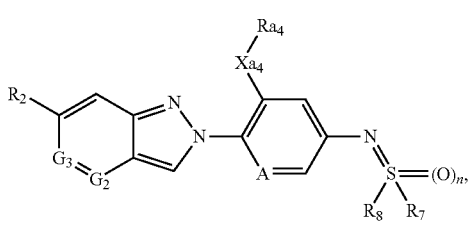

(I-7)

wherein $R_2$, $G_2$, $G_3$, A, n, $R_7$ and $R_8$ are as defined under formula I above; and wherein $Xa_4$ is S, SO or $SO_2$; $Ra_4$ is methyl, ethyl, n-propyl, i-propyl or cyclopropylmethyl.

In said preferred group of compounds of formula I-7, A is CH or N, preferably N; $Xa_4$ is preferably S or $SO_2$, more preferably $SO_2$; and $Ra_4$ is preferably ethyl. In another preferred group of compounds of formula I-7, $R_2$ is preferably $C_1$-$C_6$haloalkyl, more preferably trifluoromethyl; $G_2$ is CH; and $G_3$ is CH or N, preferably N.

In compounds of formula I-7 and all of the preferred embodiments of compounds of formula I-7 mentioned above, n is 0 or 1, preferably 1; and $R_7$ and $R_8$ are as defined under formula I above. A further preferred embodiment of said especially preferred group of compounds of formula I-7 comprises compounds wherein $R_7$ and $R_8$ are, independently from each other, $C_1$-$C_6$alkyl, $C_3$-$C_6$cycloalkyl or phenyl monosubstituted by $C_1$-$C_4$alkyl, even more preferably methyl, ethyl, cyclopropyl or phenyl substituted by methyl (preferably in the 4-position); or $R_7$ and $R_8$, together with the sulfur atom to which they are attached, form a four- to six-membered, saturated ring system, preferably said ring system is unsubstituted, and said ring system contains no or one oxygen atom.

Another preferred group of compounds of formula I is represented by the compounds of formula I-8

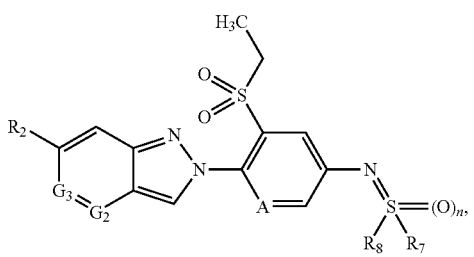

(I-8)

wherein
A is CH or N;
$R_2$ is $C_1$-$C_6$haloalkyl, preferably trifluoromethyl;
$G_2$ is CH;
$G_3$ is N or CH, preferably N;
n is 0 or 1;
$R_7$ and $R_8$ are, independently from each other, $C_1$-$C_6$alkyl, $C_3$-$C_6$cycloalkyl or phenyl monosubstituted by $C_1$-$C_4$alkyl, preferably methyl, ethyl, cyclopropyl or phenyl substituted by methyl (preferably in the 4-position); or
$R_7$ and $R_8$, together with the sulfur atom to which they are attached, form a four- to six-membered, saturated ring system, preferably said ring system is unsubstituted, and said ring system contains no or one oxygen atom.

Yet another preferred group of compounds of formula I is represented by the compounds of formula I-8a

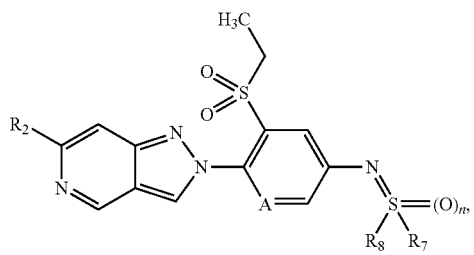

(I-8a)

wherein
A is N;
$R_2$ is $C_1$-$C_6$haloalkyl, preferably trifluoromethyl;
n is 1;
$R_7$ and $R_8$ are, independently from each other, $C_1$-$C_6$alkyl or $C_3$-$C_6$cycloalkyl, preferably methyl, ethyl or cyclopropyl; or
$R_7$ and $R_8$, together with the sulfur atom to which they are attached, form a four- to six-membered, saturated ring system, preferably said ring system is unsubstituted, and said ring system can contain one oxygen atom.

An outstanding group of compounds of formula I is represented by the compounds of formula I-6

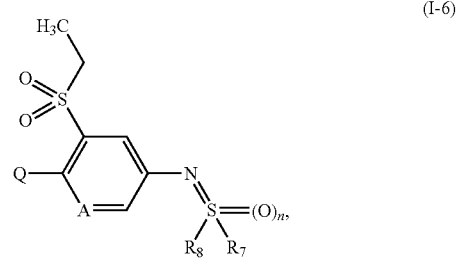

(I-6)

wherein
A is CH or N; in particular A is N;
n is 0 or 1; in particular n is 1;
$R_7$ and $R_8$ are, independently from each other, $C_1$-$C_6$alkyl, $C_3$-$C_6$cycloalkyl or phenyl which phenyl is monosubstituted by $C_1$-$C_4$alkyl, preferably methyl, ethyl, cyclopropyl or phenyl substituted by methyl (preferably in the 4-position); in particular $C_1$-$C_6$alkyl or $C_3$-$C_6$cycloalkyl, preferably methyl or cyclopropyl; or
$R_7$ and $R_8$, together with the sulfur atom to which they are attached, form a four- to six-membered, saturated ring system, preferably said ring system is unsubstituted, and said ring system can contain one oxygen atom; and
Q is a radical selected from the group consisting of formula $Q_{1a}$, $Q_{1b}$, $Q_{2a}$ and $Q_{3a}$

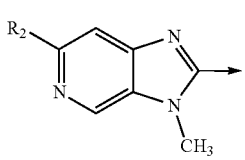

$Q_{1a}$

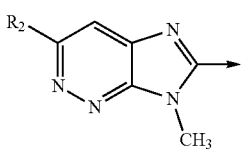

Q_{1b}

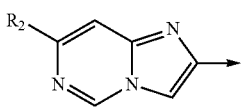

Q_{2a}

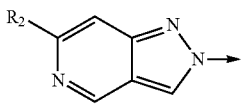

Q_{3a} in particular selected from $Q_{1a}$ and $Q_{2a}$;

wherein the arrow denotes the point of attachment to the ring incorporating the radical A; and in which $R_2$ is $C_1$-$C_6$haloalkyl, preferably trifluoromethyl.

The process according to the invention for preparing compounds of formula I is carried out in principle by methods known to those skilled in the art. More specifically, the subgroup of compounds of formula I, wherein X is SO (sulfoxide) and/or SO$_2$ (sulfone), may be obtained by means of an oxidation reaction of the corresponding sulfide compounds of formula I, wherein X is S, involving reagents such as, for example, m-chloroperoxybenzoic acid (mCPBA), hydrogen peroxide, oxone, sodium periodate, sodium hypochlorite or tert-butyl hypochlorite amongst other oxidants. The oxidation reaction is generally conducted in the presence of a solvent. Examples of the solvent to be used in the reaction include aliphatic halogenated hydrocarbons such as dichloromethane and chloroform; alcohols such as methanol and ethanol; acetic acid; water; and mixtures thereof. The amount of the oxidant to be used in the reaction is generally 1 to 3 moles, preferably 1 to 1.2 moles, relative to 1 mole of the sulfide compounds I to produce the sulfoxide compounds I, and preferably 2 to 2.2 moles of oxidant, relative to 1 mole of of the sulfide compounds I to produce the sulfone compounds I. Such oxidation reactions are disclosed, for example, in WO 2013/018928.

The subgroup of compounds of the formula I wherein n is 1, defining compounds of the formula Ia, wherein X, $R_1$, $R_7$, $R_8$, A and Q are as defined in formula I, Scheme 1

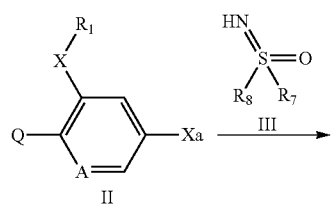

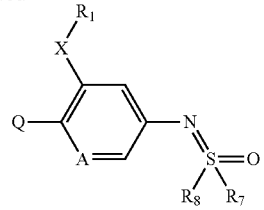

Ia may be prepared by reacting compounds of formula II, wherein X, $R_1$, A and Q are as defined in formula I, and in which Xa is a leaving group such as, for example, chlorine, bromine or iodine (preferably bromine), or an aryl-, alkyl- or haloalkylsulfonate such as trifluoromethanesulfonate, with a reagent HN=S(O)$R_7R_8$ of the formula Ill, wherein $R_7$ and $R_8$ are as defined in formula I (scheme 1). The reaction may be catalyzed by a palladium based catalyst, involving for example bis(dibenzylidene-acetone)palladium(0) (Pd(dba)$_2$), tris(dibenzylideneacetone)dipalladium(0) (Pd$_2$(dba)$_3$; optionally in form of its chloroform adduct) or palladium(II) acetate, and a ligand, for example XantPhos ((5-di-phenylphosphanyl-9,9-dimethyl-xanthen-4-yl)diphenylphosphane), RuPhos (2-dicyclohexylphosphino-2',6'-diisopropoxybiphenyl), JohnPhos ([1,1'-biphenyl]-2-ylbis(1,1-dimethyl-ethyl)phosphine), BINAP (2,2'-bis(diphenylphosphino)-1,1'-binaphthalene), tol-BINAP ([2,2'-bis(di-p-tolyl-phosphino)-1,1'-binaphthyl]) or tri-(o-tolyl)phosphine, in presence of a base, like sodium, potassium or cesium carbonate, or sodium or potassium tert-butylate, in a solvent or a solvent mixture, like, for example dioxane, 1,2-dimethoxyethane or toluene, preferably under inert atmosphere. The reaction temperature can preferentially range from room temperature to the boiling point of the reaction mixture, or the reaction may be performed under microwave irradiation. Such reactions have been described, for example, in Journal of Organic Chemistry, 65(1), 169-175; 2000, Tetrahedron Letters, 39(32), 5731-5734; 1998, Chem. Commun., 47, 7665-7667; 2011 or Tetrahedron, 70(37), 6613-6622; 2014. Alternatively, the reaction may be catalyzed by iron, for example iron(III) chloride, in presence of a ligand, such as N,N'-dimethyl-1,2-ethanediamine, and a base, such as sodium, potassium or cesium carbonate, in a solvent or a solvent mixture, like, for example dioxane, 1,2-dimethoxyethane or toluene, preferably under inert atmosphere. The reaction temperature can preferentially range from room temperature to the boiling point of the reaction mixture, or the reaction may be performed under microwave irradiation. Such reactions have been described, for example, in Advanced Synthesis & Catalysis, 350(3), 391-394; 2008. As a further alternative, the reaction may be catalyzed by copper, for example copper(I) iodide, copper(I) acetate or copper(I) oxide, optionally in presence of a ligand, such as N,N'-dimethyl-1,2-ethanediamine, and a base, such as sodium, potassium or cesium carbonate, or potassium phosphate, in a solvent or a solvent mixture, like, for example dioxane, 1,2-dimethoxyethane, toluene, N,N-dimethylformamide or dimethylsulfoxide, preferably under inert atmosphere. The reaction temperature can preferentially range from room temperature to the boiling point of the reaction mixture, or the reaction may be performed under microwave irradiation. Such reactions have been described, for example, in Advanced Synthesis & Catalysis, 349(17+18), 2673-2676; 2007, or Angewandte Chemie, International Edition, 48, 5691-5693; 2009.

Compounds of formula III, wherein $R_7$ and $R_8$ are as defined in formula I, are either known compounds, commercially available or can be prepared by known methods, described in the literature, as for example in Journal of the Chemical Society, 3004-5; 1965 or e-EROS Encyclopedia of Reagents for Organic Synthesis, 1-8; 2013. Of advantage are preparation methods for compounds of formula III starting from readily available sulfide compounds of formula V (see Chem. Commun. 53, 348-351; 2017), or from the corresponding sulfoxide compounds of formula VI (see Angewandte Chemie, International Edition, 55, 7203-7207; 2016), wherein $R_7$ and $R_8$ are as defined in formula I,

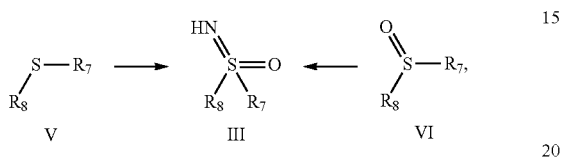

that involve, for example, ammonia, ammonium carbamate or ammonium acetate as a suitable nitrogen source, and mediated by hypervalent iodine reagents, such as diacetoxyiodobenzene, in solvents such as toluene, acetonitrile or methanol, at temperatures between 0 and 100° C., preferably around room temperature.

Compounds of formula II, wherein X, $R_1$, A and Q are as defined in formula I, and in which Xa is a leaving group, in particular those compounds wherein Xa is a halogen, are known compounds, or can be prepared by known methods, or can be synthesized in analogy to described methods found in the literature. See in particular WO 2016/071214 (Q is $Q_2$), WO 2016/026848 (Q is $Q_1$, $G_1$ is CH), WO 2016/059145 (Q is $Q_1$, $G_1$ is N) and WO 2016/020286 (Q is $Q_3$). More specifically, compounds of formula II, wherein Q is $Q_1$, and wherein X, $R_1$ and A are as defined in formula I, and in which Xa is a leaving group, in particular those compounds wherein Xa is a halogen (even more preferably chlorine, bromine or iodine), are represented by compounds of formula II-Q1 below (scheme 1a), wherein $G_1$, $X_1$ and $R_2$ are defined as under formula I above. Preparation of compounds of formula II-Q1, wherein $G_1$ is CH can be achieved in analogy to descriptions found in WO 2015/000715 and WO 2016/026848; preparation of compounds of formula II-Q1, wherein $G_1$ is N can be achieved in analogy to descriptions found in WO 2016/059145.

Similarly, compounds of formula II, wherein Q is $Q_2$, and wherein X, $R_1$ and A are as defined in formula I, and in which Xa is a leaving group, in particular those compounds wherein Xa is a halogen (even more preferably chlorine, bromine or iodine), are represented by compounds of formula II-Q2 below (scheme 1a), wherein $G_3$ and $R_2$ are defined as under formula I above. Preparation of compounds of formula II-Q2, wherein $G_3$ is N can be achieved in analogy to descriptions found in WO 2016/071214; preparation of compounds of formula II-Q2, wherein $G_3$ is CH can be achieved in analogy to descriptions found in WO 2015/000715.

Furthermore, compounds of formula II, wherein Q is $Q_3$, and wherein X, $R_1$ and A are as defined in formula I, and in which Xa is a leaving group, in particular those compounds wherein Xa is a halogen (even more preferably chlorine, bromine or iodine), are represented by compounds of formula II-Q3 below (scheme 1a), wherein $G_2$, $G_3$ and $R_2$ are defined as under formula I above. Preparation of compounds of formula II-Q3, wherein $G_2$ and $G_3$ are CH can be achieved in analogy to descriptions found in WO 2013/191113; preparation of compounds of formula II-Q3, wherein $G_2$ is N and $G_3$ is CH can also be achieved in analogy to descriptions found in WO 2013/191113; preparation of compounds of formula II-Q3, wherein $G_2$ is CH and $G_3$ is N can be achieved in analogy to descriptions found in WO 2017/134066; preparation of compounds of formula II-Q3, wherein $G_2$ and $G_3$ are N can be achieved in analogy to descriptions found in WO 2016/020286.

Scheme 1a

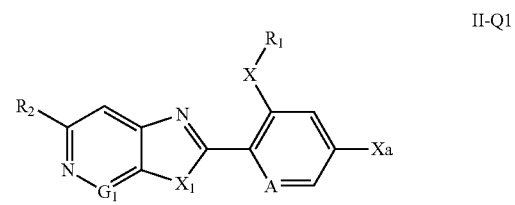

$G_1$ = CH: WO 2015/000715,
WO 2016/026848
$G_1$ = N:  WO 2015/059145

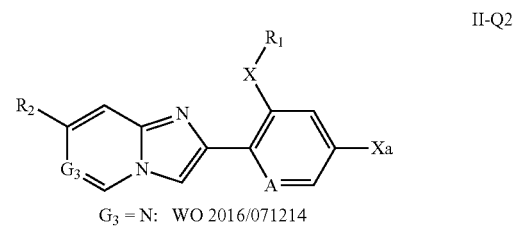

$G_3$ = N:  WO 2016/071214
$G_3$ = CH: WO 2015/000715

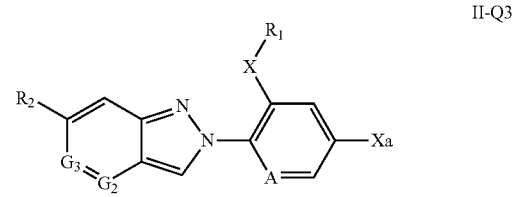

$G_2$, $G_3$ = CH:     WO 2013/191113
$G_2$ = N, $G_3$ = CH: WO 2013/191113
$G_2$ = CH, $G_3$ = N: WO 2017/134066
$G_2$, $G_3$ = N:      WO 2016/020286

Alternatively, compounds of the formula Ia, wherein X, $R_1$, $R_7$, $R_8$, A and Q are as defined in formula I, Scheme 2a

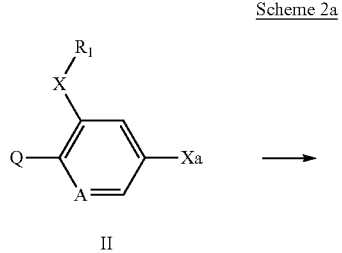

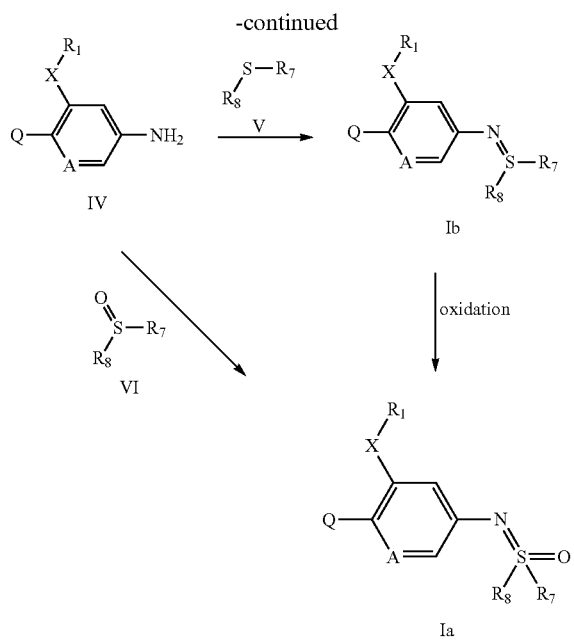

may be prepared by an oxidation step from the subgroup of compounds of the formula I wherein n is 0, defining compounds of the formula Ib, wherein X, $R_1$, $R_7$, $R_8$, A and Q are as defined in formula I (scheme 2a). In such transformations, classical oxidation reagents may be used such as, for example, $KMnO_4$, $NaMnO_4$, mCPBA, $NaIO_4/RuO_2$, $NaIO_4/RuCl_3$, $H_2O_2$, or oxone, under conditions described in, for example, Journal of Organic Chemistry, 44, 2510; 1979 or Monatshefte fuer Chemie 116(10), 1153-64; 1985. In particular, the use of ruthenium salts in combination with alkali metal periodates and alternatively the use of alkali metal permanganates was described in WO 2008/097235 and WO2008/106006. Suitable solvents for the oxidation are, for example, dichloromethane, chloroform, methanol, ethanol or acetic acid.

Compounds of the formula Ib, wherein X, $R_1$, $R_7$, $R_8$, A and Q are as defined in formula I, may be prepared by reacting compounds of formula IV, wherein X, $R_1$, A and Q are as defined in formula I, with a sulfide reagent $SR_7R_8$ of the formula V, wherein $R_7$ and $R_8$ are as defined in formula I, under imination reaction conditions. Likewise, compounds of the formula Ia, wherein X, $R_1$, $R_7$, $R_8$, A and Q are as defined in formula I, may be prepared by reacting compounds of formula IV, wherein X, $R_1$, A and Q are as defined in formula I, with a sulfoxide reagent $S(O)R_7R_8$ of the formula VI, wherein $R_7$ and $R_8$ are as defined in formula I, under similar imination reaction conditions. Typical preparation methods and reaction conditions may be found, for example, in H. Okamura, C. Bolm, Org. Lett. 2004, 6, 1305-1307; H. Okamura, C. Bolm, Chem. Lett. 2004, 33, 482-487; D. Leca, K. Song, M. Amatore, L. Fensterbank, E. Lacôte, M. Malacria, Chem. Eur. J. 2004, 10, 906-916; or M. Reggelin, C. Zur, Synthesis, 2000, 1-64. Of particular interest are metal-free imination methods involving compounds of the formula IV, reagents of the formula V or VI, and an oxidant, for example, $PhI(OAc)_2$ (hypervalent iodine) as described in G. Y. Cho, C. Bolm, Tetrahedron Lett. 2005, 46, 8007-8008; or N-bromo-succinimide (NBS) and a base such as sodium or potassium ter-butoxide as described in C. Bolm et al., Synthesis 2010, No 17, 2922-2925. Oxidants such as N-iodosuccinimide (NIS) or iodine may be also used alternatively as described, for example, in O. G. Mancheno, C. Bolm, Org. Lett. 2007, 9, 3809-3811. An example of hypochlorite salts being used as oxidant, such as sodium hypochlorite NaOCl or calcium hypochlorite $Ca(OCl)_2$, was described in WO2008/106006.

Compounds of formula V and compounds of formula VI, wherein $R_7$ and $R_8$ are as defined in formula I, are either known compounds, commercially available or can be prepared by known methods, described in the literature.

Alternatively, compounds of the formula Ib, wherein X, $R_1$, $R_7$, $R_8$, A and Q are as defined in formula I, Scheme 2b

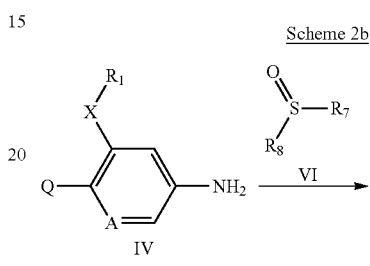

may be prepared (scheme 2b) by reacting compounds of formula IV, wherein X, $R_1$, A and Q are as defined in formula I, with a sulfoxide reagent $S(O)R_7R_8$ of the formula VI, wherein $R_7$ and $R_8$ are as defined in formula I, for example by involving phosphorus pentoxide (Monatsh. Chem. 101, 396-404; 1970), or or trifluoroacetic anhydride (J. Org. Chem. 40, 2758-2764; 1975), in presence of triethylamine, and in solvents such as chloroform or dichloromethane, at temperatures between −80 and 100° C., preferably between −70 and 60° C.

Compounds of formula IV, wherein X, $R_1$, A and Q are as defined in formula I, may be prepared in a two steps process from compounds of formula II, wherein X, $R_1$, A and Q are as defined in formula I, and in which Xa is a leaving group such as, for example, chlorine, bromine or iodine, or an aryl-, alkyl- or haloalkylsulfonate such as trifluoromethanesulfonate (scheme 3).

Scheme 3

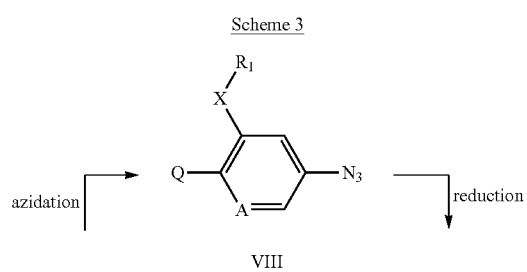

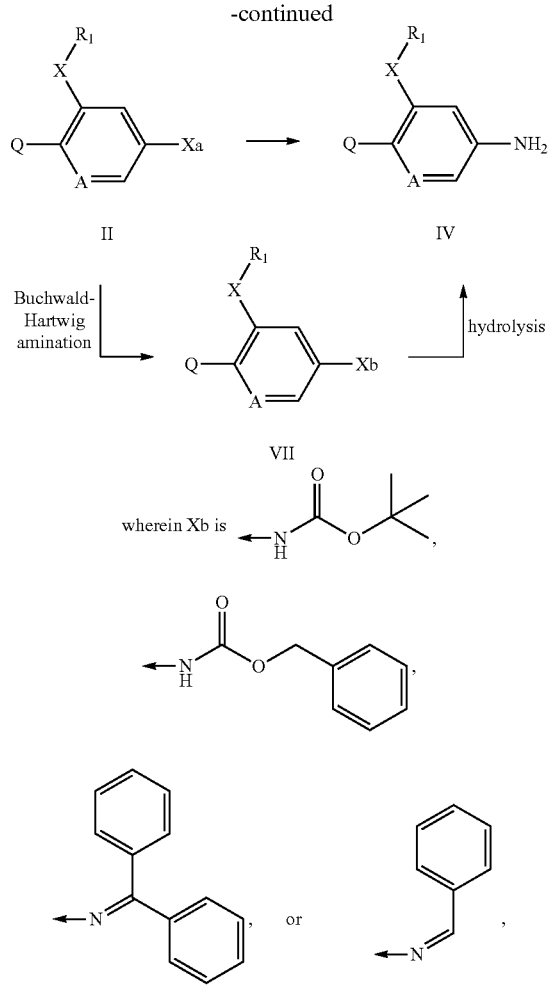

Such a transformation involves (i) reacting a compound of the formula II, wherein the leaving group Xa is preferably chlorine or bromine, with, for example, tert-butylcarbamate, benzyl carbamate (wherein the phenyl may be optionally substituted by one or two methoxy), diphenylmethanimine or phenyl-methanimine under Buchwald-Hartwig type cross coupling conditions generating compounds of the formula VII, wherein X, $R_1$, A and Q are as defined in formula I, and in which Xb is either —NHC(O)Ot-Bu, —NHC(O)OCH$_2$Ph (wherein the phenyl may be optionally substituted by one or two methoxy), —N=C(Ph)$_2$ or —N=CH(Ph); followed by (ii) hydrolysis of the intermediate compounds of formula VII into the compounds of formula IV. Such a process (i) may be catalyzed by a palladium based catalyst, involving for example bis(dibenzylideneacetone)palladium(0) (Pd (dba)$_2$), tris(dibenzylideneacetone)dipalladium(0) (Pd$_2$ (dba)$_3$; optionally in form of its chloroform adduct) or palladium(II) acetate, and a ligand, for example XPhos (2-dicyclohexylphosphino-2',4',6'-triisopropyl-biphenyl), XantPhos ((5-di-phenylphosphanyl-9,9-dimethyl-xanthen-4-yl)diphenyl-phosphane), RuPhos (2-dicyclohexylphosphino-2',6'-diisopropoxybiphenyl), JohnPhos ([1,1'-biphenyl]-2-ylbis(1,1-dimethyl-ethyl)phosphine), BINAP (2,2'-bis(diphenylphosphino)-1,1'-binaphthalene), tol-BINAP ([2,2'-bis(di-p-tolyl-phosphino)-1,1'-binaphthyl]) or tri-(o-tolyl) phosphine, in presence of a base, like sodium, potassium or cesium carbonate, or sodium or potassium tert-butylate, in a solvent or a solvent mixture, like, for example dioxane, 1,2-dimethoxyethane or toluene, preferably under inert atmosphere, at reaction temperatures ranging preferentially from room temperature to the boiling point of the reaction mixture, or the reaction may be performed under microwave irradiation. Alternatively, such a process (i) may be catalyzed by a copper based catalyst, involving for example copper(I) iodide (CuI) or copper(II) trifluoromethanesulfonate, optionally in the presence of a ligand, such as 2,2'-bipyridine, proline, N,N'-dimethyl glycine or ethylene glycol, in the presence of a suitable base such as triethylamine, sodium carbonate, potassium carbonate, cesium carbonate, sodium methoxide, sodium tert-butoxide, potassium tert-but oxide, in a suitable solvent such as 1,4-dioxane, N,N-dimethyl-formamide, dimethyl sulfoxide or N-methylpyrrolidinone at temperatures between 100 and 180° C., or the reaction may be performed under microwave irradiation. Hydrolysis (ii) may be conducted usually under aqueous, either acidic or basic, conditions known to a person skilled in the art. Typically, compounds of the formula VII are treated with aqueous hydrogen chloride, or trifluoroacetic acid, optionally in the presence of a solvent, such as 1,4-dioxane, tetrahydrofurane or dichloromethane, at reaction temperatures ranging preferentially from 0° C. to the boiling point of the reaction mixture, or the reaction may be performed under microwave irradiation.

Alternatively, such a transformation II to IV involves (iii) reacting a compound of the formula II, wherein the leaving group Xa is preferably chlorine or bromine with, for example, sodium- or trimethylsilyl-azide under azidation conditions generating compounds of the formula VIII, wherein X, $R_1$, A and Q are as defined in formula I; followed by (iv) reduction of the intermediate compounds of formula VIII into the compounds of formula IV. Such a process (iii) may be conducted in a solvent such as N,N-dimethylformamide or dimethyl sulfoxide, optionally in the presence of a copper catalyst, such as copper iodide, optionally in the further presence of a ligand, such as proline or N,N'-dimethylethylenediamine at temperatures between 50 and 150° C. Reduction (iv) may be conducted under conditions known to a person skilled in the art (see for example: R. C. Larock, Synthetic Organic Methodology: Comprehensive Organic Transformations. A Guide to Functional Group Preparations, 1989; p. 409) in various organic or aqueous solvents compatible to these conditions, at temperatures from below 0° C. up to the boiling point of the solvent system. Alternatively, the sequence from II to IV via VIII may be done in one step, whereby the intermediate azide VIII is reduced in situ under copper catalyst conditions as described in, for example, Journal of Organic Chemistry (2010), 75(14), 4887-4890 and references cited therein. Such a one-pot process II to IV via VIII was also described in, for example, WO 2016/091731.

Alternatively, compounds of the formula I, wherein Q is $Q_1$, defining compounds of the formula I-Q1, wherein X, R, n, $R_7$, $R_8$, A, $X_1$, $G_1$ and $R_2$ are as defined in formula I, Scheme 4

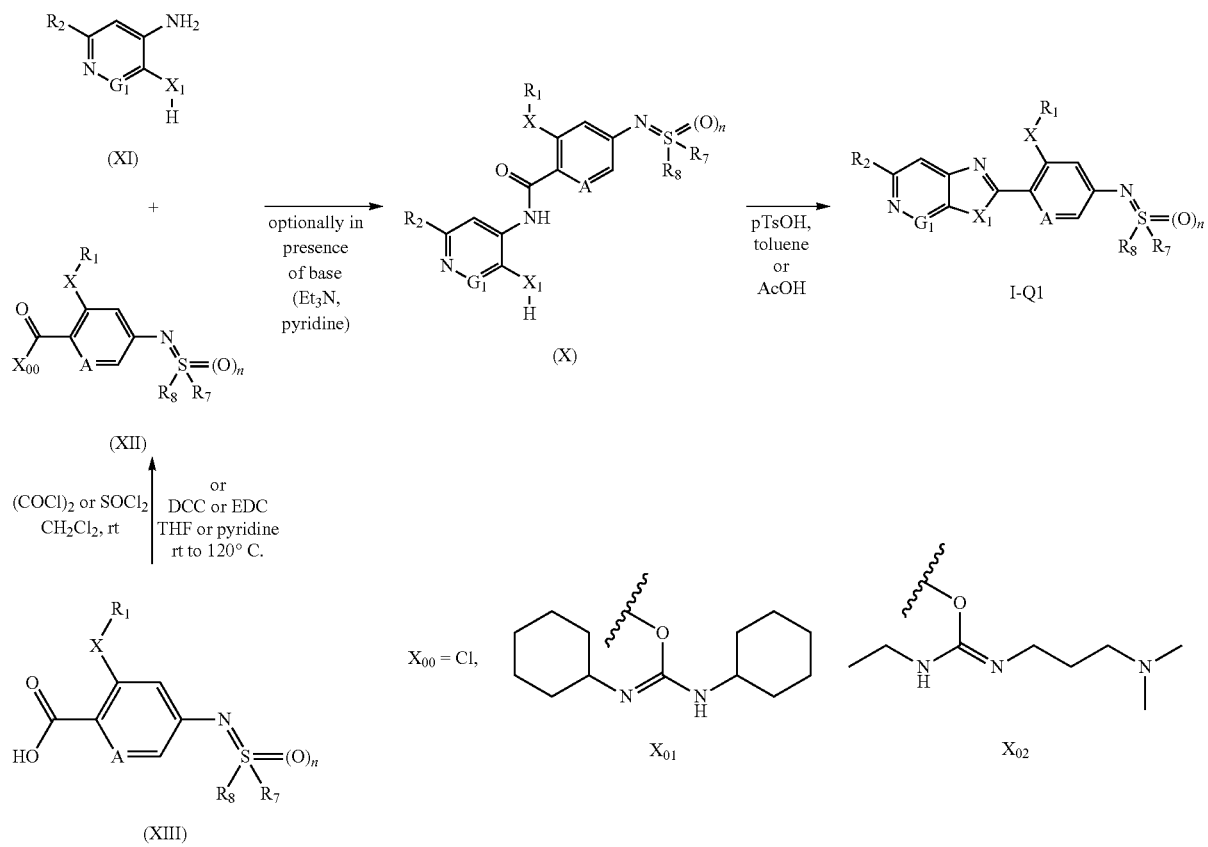

may be prepared (scheme 4) by cyclizing compounds of the formula (X), wherein X, $R_1$, n, $R_7$, $R_8$, A, $X_1$, $G_1$ and $R_2$ are as defined in formula I, for example through heating in acetic acid or trifluoroacetic acid (preferably when $X_1$ is $NR_3$, wherein $R_3$ is $C_1$-$C_4$alkyl), at temperatures between 0 and 180° C., preferably between 20 and 150° C., optionally under microwave irradiation. Cyclization of compounds of formula (X) may also be achieved in the presence of an acid catalyst, for example methanesulfonic acid, or para-toluene-sulfonic acid p-TsOH, in an inert solvent such as N-methyl pyrrolidone or xylene, at temperatures between 25-180° C., preferably 100-170° C. Such processes have been described previously, for example, in WO 2010/125985. Alternatively, compounds of formula (X) may be converted into compounds of formula I-Q1 (preferably when $X_1$ is O) using triphenylphosphine, di-isopropyl azodicarboxylate (or di-ethyl azodicarboxylate) in an inert solvent such as tetrahydrofuran THF at temperatures between 20-50° C. Such Mitsunobu conditions have been previously described for these transformations (see WO 2009/131237).

Compounds of the formula (X), wherein X, $R_1$, n, $R_7$, $R_8$, A, $X_1$, $G_1$ and $R_2$ are as defined in formula I, may be prepared by i) Activation of compounds of formula (XIII), wherein X, $R_1$, n, $R_7$, $R_8$ and A are as defined in formula I, by methods known to those skilled in the art and described in, for example, Tetrahedron, 2005, 61 (46), 10827-10852, to form an activated species (XII), wherein X, $R_1$, n, $R_7$, $R_8$ and A are as defined in formula I, and wherein $X_{00}$ is halogen, preferably chlorine. For example, compounds (XII) where $X_{00}$ is halogen, preferably chlorine, are formed by treatment of (XIII) with, for example, oxalyl chloride $(COCl)_2$ or thionyl chloride $SOCl_2$ in the presence of catalytic quantities of N,N-dimethylformamide DMF in inert solvents such as methylene chloride $CH_2Cl_2$ or tetrahydrofuran THF at temperatures between 20 to 100° C., preferably 25° C. Alternatively, treatment of compounds of formula (XIII) with, for example, 1-ethyl-3-(3-dimethylaminopropyl)carbodiimide EDC or dicyclohexyl carbodiimide DCC will generate an activated species (XII), wherein $X_{00}$ is $X_{01}$ or $X_{02}$ respectively, in an inert solvent, such as pyridine or tetrahydrofuran THF, optionally in the presence of a base, such as triethyl-amine, at temperatures between 50-180° C.; followed by ii) Treatment of the activated species (XII) with compounds of the formula XI, wherein $X_1$, $G_1$ and $R_2$ are as defined in formula I, in the presence of a base, such as triethylamine, N,N-diisopropylethyl-amine or pyridine, in an inert solvents such as dichloromethane, tetrahydrofuran, dioxane, N,N-dimethylformamide, N,N-dimethylacetamide, acetonitrile, ethyl acetate or toluene, at temperatures between 0 and 50° C., to form the compounds of formula (X). Compounds of formula (XI), wherein $X_1$, $G_1$ and $R_2$ are as defined in formula I, have been previously described, for example, in WO 2012/086848, WO 2015/000715, and WO 2016/116338.

Compounds of formula (XIII), wherein X, $R_1$, n, $R_7$, $R_8$ and A are as defined in formula I, Scheme 5

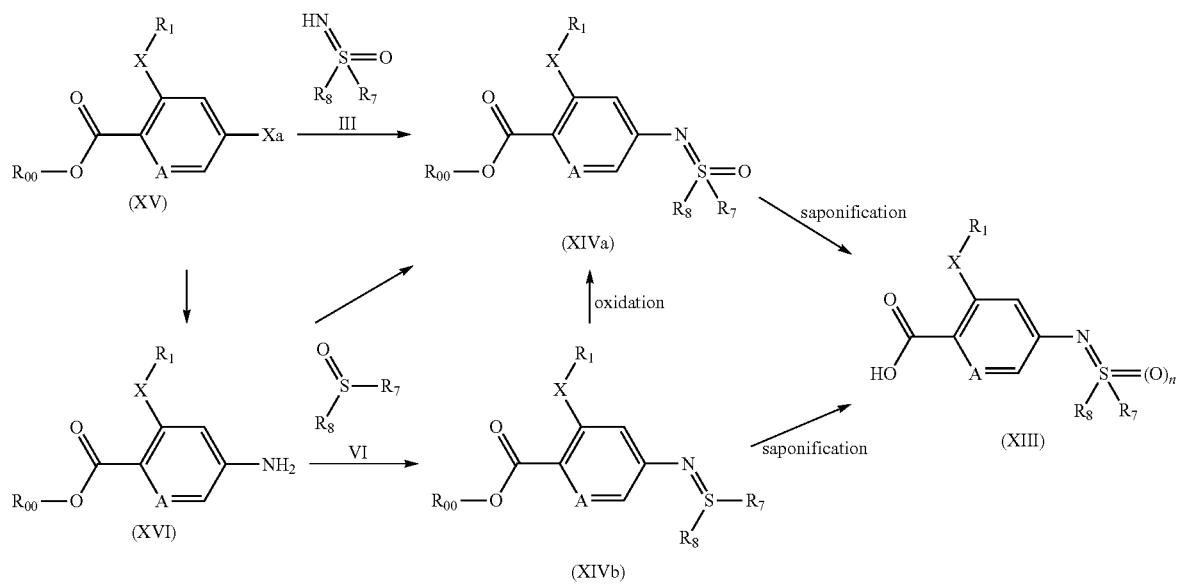

may be prepared (scheme 5) by saponification of either compounds of formula (XIVa) or compounds of formula (XIVb), wherein X, $R_1$, $R_7$, $R_8$ and A are as defined in formula I, and in which $R_{00}$ is $C_1$-$C_6$alkyl, under conditions known to a person skilled in the art (using for example conditions such as: aqueous sodium, potassium or lithium hydroxide in methanol, ethanol or dioxane at room temperature, or up to refluxing conditions).

Compounds of formula (XIVa), wherein X, $R_1$, $R_7$, $R_8$ and A are as defined in formula I, and in which $R_{00}$ is $C_1$-$C_6$alkyl, may be prepared by reacting compounds of formula (XV), wherein X, $R_1$ and A are as defined in formula I, and wherein $R_{00}$ is $C_1$-$C_6$alkyl, and in which Xa is a leaving group such as, for example, chlorine, bromine or iodine (preferably chlorine or bromine), or an aryl-, alkyl- or haloalkylsulfonate such as trifluoromethanesulfonate, with a reagent HN=S(O)$R_7R_8$ of formula III, wherein $R_7$ and $R_8$ are as defined in formula I, under conditions already described above (see scheme 1, transformation of compounds II into Ia).

Compounds of formula (XIVa), wherein X, $R_1$, $R_7$, $R_8$ and A are as defined in formula I, and in which $R_{00}$ is $C_1$-$C_6$alkyl, may also be prepared by oxidation of compounds of formula (XIVb), wherein X, $R_1$, $R_7$, $R_8$ and A are as defined in formula I, and in which $R_{00}$ is $C_1$-$C_6$alkyl, under conditions already described above (see scheme 2a, transformation of compounds Ib into Ia). Alternatively, compounds of formula (XIVa), wherein X, $R_1$, $R_7$, $R_8$ and A are as defined in formula I, and in which $R_{00}$ is $C_1$-$C_6$alkyl, may also be prepared from compounds of formula (XVI), wherein X, $R_1$ and A are as defined in formula I, and in which $R_{00}$ is $C_1$-$C_6$alkyl, under conditions already described above (see scheme 2a, transformation of compounds IV into Ia).

Compounds of formula (XIVb), wherein X, $R_1$, $R_7$, $R_8$ and A are as defined in formula I, and in which $R_{00}$ is $C_1$-$C_6$alkyl, may be prepared by reacting compounds of formula (XVI), wherein X, $R_1$ and A are as defined in formula I, and in which $R_{00}$ is $C_1$-$C_6$alkyl, with a reagent S(O)$R_7R_8$ of formula VI, wherein $R_7$ and $R_8$ are as defined in formula I, under conditions already described above (see scheme 2b, transformation of compounds IV into Ib). Alternatively, compounds of formula (XIVb), wherein X, $R_1$, $R_7$, $R_8$ and A are as defined in formula I, and in which $R_{00}$ is $C_1$-$C_6$alkyl, may be prepared by reacting compounds of formula (XVI), wherein X, $R_1$ and A are as defined in formula I, and in which $R_{00}$ is $C_1$-$C_6$alkyl, with a reagent $SR_7R_8$ of formula V, wherein $R_7$ and $R_8$ are as defined in formula I, under conditions already described above (see scheme 2a, transformation of compounds IV into Ib). Compounds of formula (XVI), wherein X, $R_1$ and A are as defined in formula I, and in which $R_{00}$ is $C_1$-$C_6$alkyl, may be prepared from compounds of formula (XV), wherein X, $R_1$ and A are as defined in formula I, and wherein $R_{00}$ is $C_1$-$C_6$alkyl, and in which Xa is a leaving group such as, for example, chlorine, bromine or iodine (preferably chlorine or bromine), or an aryl-, alkyl- or haloalkylsulfonate such as trifluoromethanesulfonate, under conditions already described above (see scheme 3, transformation of compounds II into IV).

Compounds of formula (XV), wherein X, $R_1$ and A are as defined in formula I, and wherein $R_{00}$ is $C_1$-$C_6$alkyl, and in which Xa is a leaving group such as, for example, chlorine, bromine or iodine, or an aryl-, alkyl- or haloalkylsulfonate such as trifluoromethanesulfonate, in particular those compounds wherein Xa is a halogen (even more preferably chlorine, bromine or iodine), are either known compounds, commercially available or may be prepared by known methods, described in the literature, as for example in WO 2016/005263, WO 2016/023954, WO 2016/026848 and WO 2016/104746.

Compounds of the formula I-$Q_1$, wherein X, $R_1$, n, $R_7$, $R_8$ and A, are as defined in formula I, and in which $X_1$ is $NR_3$, wherein $R_3$ is $C_1$-$C_4$alkyl, even more specifically in which $X_1$ is $NCH_3$, and wherein $G_1$ is CH and $R_2$ is $C_1$-$C_6$haloalkyl (preferably trifluoromethyl), defining compounds of formula I-$Q_1$-A,

Scheme 6

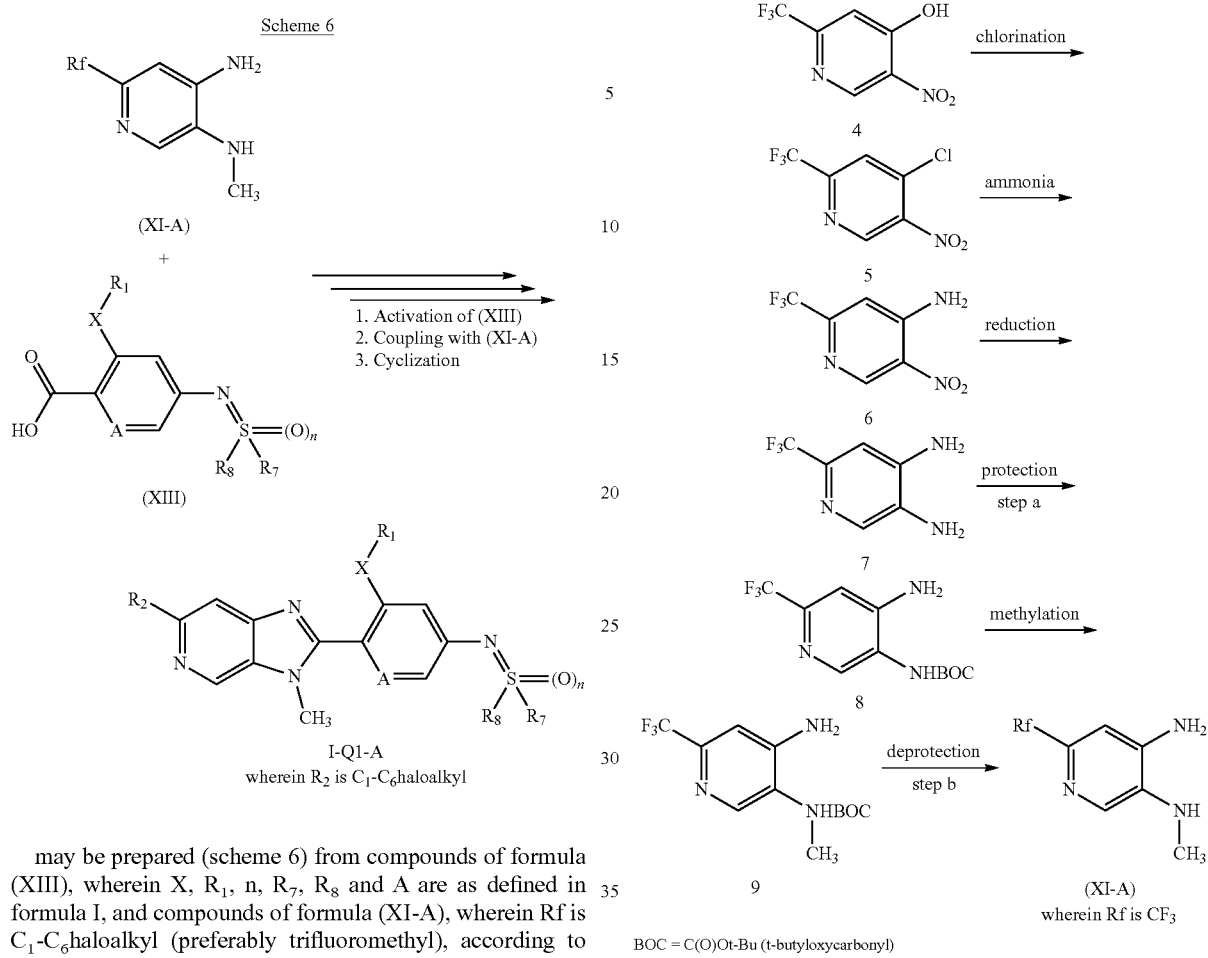

may be prepared (scheme 6) from compounds of formula (XIII), wherein X, $R_1$, n, $R_7$, $R_8$ and A are as defined in formula I, and compounds of formula (XI-A), wherein Rf is $C_1$-$C_6$haloalkyl (preferably trifluoromethyl), according to processes and conditions described above in scheme 4 and, for example, in WO 2015/000715.

In the particular situation where Rf is trifluoromethyl, compounds of formula (XI-A) may be prepared from commercially available reactants 1 and 1' via a sequence shown in scheme 7 and according to methods described in WO 2011/161612, U.S. Pat. No. 7,767,687, WO 2002/050062, WO 2016/046071 and WO 2015/000715.

Scheme 7

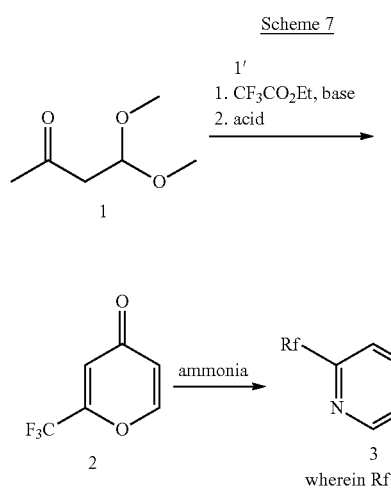

BOC = C(O)Ot-Bu (t-butyloxycarbonyl)

However, the described route encompasses many reaction steps which reduce yield and quality of the desired end-product. In particular, selective methylation of one nitrogen in the diaminopyridine intermediate 7 necessitates protection (step a) and deprotection (step b) steps which unfavorably contribute to a low atom-economy of the overall sequence.

Alternatively, compounds of formula (XI-A), or a salt thereof (such as a hydrohalide salt, preferably a hydrochloride or a hydrobromide salt, or any other equivalent salt), wherein Rf is $C_1$-$C_6$haloalkyl (preferably trifluoromethyl), can be advantageously prepared from compounds of formula 10, or a salt thereof (such as a hydrohalide salt, preferably a hydrochloride or a hydrobromide salt, or any other equivalent salt), wherein Rf is $C_1$-$C_6$haloalkyl (preferably trifluoromethyl), via halogenation and coupling of methylamine (scheme 8).

Scheme 8

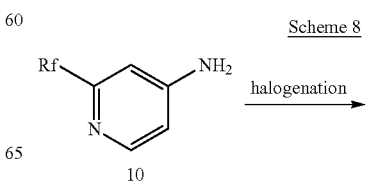

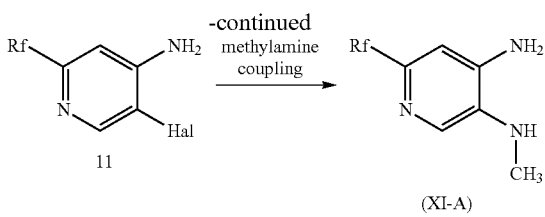

(XI-A)

Suitable halogenating agents for the preparation of compounds of formula 11, or a salt thereof (such as a hydrohalide salt, preferably a hydrochloride or a hydrobromide salt, or any other equivalent salt), wherein Rf is $C_1$-$C_6$haloalkyl (preferably trifluoromethyl), and in which Hal is a halogen, preferably chlorine, bromine or iodine (more preferably bromine), from compounds of formula 10, wherein Rf is $C_1$-$C_6$haloalkyl (preferably trifluoromethyl), are for example N-chlorosuccinimide (NCS), N-bromosuccinimide (NBS) or N-iodosuccinimide (NIS), or alternatively chlorine, bromine or iodine. Such halogenation reactions are carried out in an inert solvent, such as chloroform, carbon tetrachloride, 1,2-dichloroethane, acetic acid, ethers, acetonitrile or N,N-dimethylformamide, at temperatures between 20-200° C., preferably room temperature to 100° C. Particularly preferred are brominating reagents, such as bromine, N-bromosuccinimide NBS, 1,3-dibromo-5,5-dimethylhydantoin and $H_2O_2$/$NH_4Br$. Even more preferred is the combination of ammonium bromide $NH_4Br$ and hydrogen peroxide (such as a 10-30% solution in water by weight) in acetic acid as solvent, at temperatures between 20-100° C. Such brominations are known from the literature, for example from Journal of Molecular Catalysis A: Chemical, 2007, 267, 30-33; Heterocycles, 2013, 87, 1279; and Synthetic Communications 2004, 34, 12, 2143-2152.

Methylamine coupling conditions involve reacting compounds of formula 11, or a salt thereof (such as a hydrohalide salt, preferably a hydrochloride or a hydrobromide salt, or any other equivalent salt), wherein Rf is $C_1$-$C_6$haloalkyl (preferably trifluoromethyl), and in which Hal is a halogen, preferably chlorine, bromine or iodine (more preferably bromine), with methylamine, a methylamine salt (such as a hydrohalide salt, preferably a hydrochloride or a hydrobromide salt, or any other equivalent salt) or a suitable methylamine derivative to form the compound of formula (XI-A), or a salt thereof (such as a hydrohalide salt, preferably a hydrochloride or a hydrobromide salt, or any other equivalent salt), wherein Rf is $C_1$-$C_6$haloalkyl (preferably trifluoromethyl). Preferably, gaseous methylamine or an aqueous solution (strength of 10 to 40% by weight) of methylamine are used. Such a process may be catalyzed by a transition metal catalyst, such as a copper, palladium or nickel catalyst, optionally in the presence of a suitable ligand. Preferably, the coupling is catalyzed by a copper based catalyst, involving for example copper(I) iodide (CuI), copper(I) chloride (CuCl), copper (I) bromide (CuBr), copper(I) oxide ($Cu_2O$) or copper(II) sulfate ($CuSO_4$), optionally in the presence of a ligand. Preferred ligands are 8-hydroxyquinoline, 6,7-dihydro-5H-quinolin-8-one oxime and 1-(2-pyridyl)ethanone oxime. The amount of metal catalyst and ligand may be between 0.01 mol % and 25 mol %, more preferentially between 0.1 and 10 mol %. The coupling may be carried out in the presence of a base, such as sodium or potassium carbonate, sodium or potassium phosphate, sodium or potassium hydroxide, or alternatively using an access of methylamine and no additional base. Typically, the coupling reaction is done in a solvent or a solvent mixture, containing for example water, dioxane, 1,2-dimethoxyethane, methanol, ethanol, tetrahydrofuran, dioxane, dimethylsulfoxide DMSO or toluene. The preferred solvent is water or water with a water miscible co-solvent. Preferably, the coupling reaction is done under inert atmosphere, at reaction temperatures ranging preferentially from room temperature to 200° C., more preferentially from 50° C. to 150° C. Some suitable catalysts and coupling conditions are described for example in Adv. Synth. Catal. 2015, 357, 714-718; and Green Chem., 2012, 14, 1268-1271.

The sequence shown in scheme 8 to prepare the compound of formula (XI-A) is particularly advantageous as it avoids the unproductive protection and deprotection steps described in scheme 7.

Compounds of formula 10, or a salt thereof (such as a hydrohalide salt, preferably a hydrochloride or a hydrobromide salt, or any other equivalent salt), wherein Rf is $C_1$-$C_6$haloalkyl (preferably trifluoromethyl), can be prepared from compounds of formula 3, wherein Rf is $C_1$-$C_6$haloalkyl (preferably trifluoromethyl), via activation and ammonia condensation steps (scheme 9).

Scheme 9

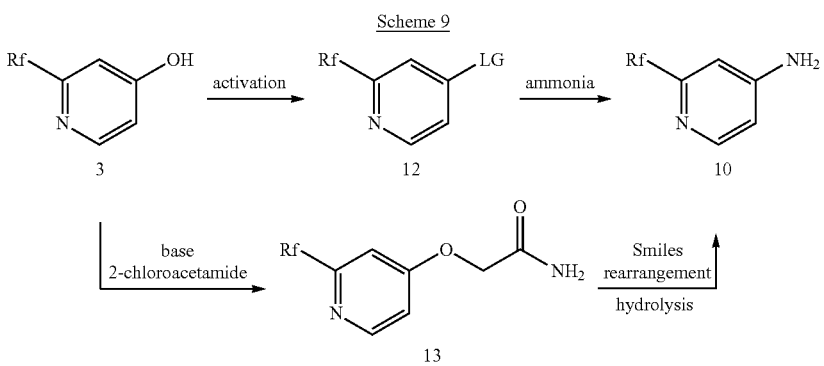

Compounds of formula 12, in which Rf is $C_1$-$C_6$haloalkyl (preferably trifluoromethyl), and wherein LG is a leaving group such as, for example, chlorine, bromine or iodine (preferably chlorine or bromine), or an arylsulfonate (such as p-toluenesulfonate or tosylate —OTs), an alkylsulfonate (such as methane-sulfonate or mesylate —OMs) or an haloalkylsulfonate (such as trifluoromethanesulfonate or triflate —OTf), can be prepared by treating compounds of formula 3, wherein Rf is $C_1$-$C_6$haloalkyl (preferably trifluoromethyl), with either, for example, oxalyl chloride, thionyl chloride, phosgene, diphosgene, triphosgene, phosphorus oxychloride, phosphorus oxybromide, mesyl chloride, tosyl chloride or trifluoromethanesulfonic anhydride under conditions known to a person skilled in the art. In particular, reacting compounds of formula 3 with oxalyl chloride, optionally in presence of a catalytic amount of N,N-dimethylformamide DMF, in an inert solvent such as dichloromethane, cyclohexane or toluene, at temperatures ranging preferentially from room temperature to 120° C., more preferentially from 25° C. to 100° C., will generate compounds of formula 12, wherein LG is chlorine.

Compounds of formula 10, wherein Rf is $C_1$-$C_6$haloalkyl (preferably trifluoromethyl), can be prepared by reacting compounds of formula 12, in which Rf is $C_1$-$C_6$haloalkyl (preferably trifluoromethyl), and wherein LG is a leaving group such as, for example, chlorine, bromine or iodine (preferably chlorine or bromine), or an arylsulfonate (such as p-toluenesulfonate or tosylate —OTs), an alkylsulfonate (such as methanesulfonate or mesylate —OMs) or an haloalkylsulfonate (such as trifluoromethanesulfonate or triflate —OTf), with ammonia $NH_3$ or an ammonia equivalent such as for example ammonium hydroxide $NH_4OH$, ammonium chloride $NH_4Cl$, ammonium acetate $NH_4OAc$, ammonium carbonate $(NH_4)_2CO_3$, and other $NH_3$ surrogates. This transformation is preferably performed in suitable solvents (or diluents) such as alcohols, amides, esters, ethers, nitriles, dimethylsulfoxide DMSO and water, particularly preferred are methanol, ethanol, 2,2,2-trifluoroethanol, propanol, isopropanol, N,N-dimethyl-formamide, N,N-dimethylacetamide, dioxane, tetrahydrofuran, dimethoxyethane, acetonitrile, dimethylsulfoxide, ethyl acetate, water or mixtures thereof, optionally in presence of a copper catalyst, for example copper(I) iodide, with or without an additive such as L-proline, N,N'-dimethylcyclohexane-1,2-diamine or N,N'-dimethylethylenediamine, optionally in presence of a base, for example potassium carbonate, sodium carbonate or cesium carbonate, at temperatures ranging preferentially from room temperature to 180° C., more preferentially from 25° C. to 150° C., optionally under microwave irradiation or pressurized conditions using an autoclave.

Alternatively, compounds of formula 10, wherein Rf is $C_1$-$C_6$haloalkyl (preferably trifluoromethyl), can be prepared via an alkylation, Smiles rearrangement and hydrolysis sequence (scheme 9). Reacting the compound of formula 3, wherein Rf is $C_1$-$C_6$haloalkyl (preferably trifluoromethyl), with 2-chloro-acetamide (alkylation) in presence of an inorganic or organic base, such as sodium bicarbonate, potassium carbonate, triethylamine or pyridine, in an inert solvent such as dioxane, acetonitrile, toluene, dimethylsulfoxide, N-methylpyrrolidone, N,N-dimethylformamide or N,N-dimethylacetamide, at temperatures ranging preferentially from room temperature to 200° C., more preferentially from 25° C. to 120° C., will generate the compound of formula 13, wherein Rf is $C_1$-$C_6$haloalkyl (preferably trifluoromethyl). Optionally, the compound of formula 13 may be isolated and purified. Advantageously however, upon further thermal activation, the compound of formula 13 can undergo a Smiles rearrangement, followed by an in-situ hydrolysis under the basic reaction conditions to yield directly the desired compound of formula 10, wherein Rf is $C_1$-$C_6$haloalkyl (preferably trifluoromethyl), in a one-pot procedure. Thermal activation is achieved by heating the mixture to temperatures ranging preferentially from 80° C. to 250° C., more preferentially from 120° C. to 200° C., with optional use of microwave heating. Such an advantageous one-pot procedure can be performed in analogy to descriptions found in, for example, V. I. Tyvorskii, D. N. Bobrov, O. G. Kulinkovich, K. A. Tehrani, N. De Kimpe, Tetrahedron 2001, 57, 2051-2055.

Alternatively, compounds of formula 10, or a salt thereof (such as a hydrohalide salt, preferably a hydrochloride or a hydrobromide salt, or any other equivalent salt), wherein Rf is $C_1$-$C_6$haloalkyl (preferably trifluoromethyl), can be prepared more directly from conveniently available reactants 14, wherein $Y_1$ is independently halogen or $C_1$-$C_4$-alkoxy, or the two radicals $Y_1$ in a compound of formula 14 together form a group —O—$(CH_2)_m$—O—, wherein m is 2, 3 or 4, and reactants 15, wherein Rf is $C_1$-$C_6$haloalkyl (preferably trifluoromethyl), and in which $Y_2$ is $C_1$-$C_6$alkoxy, chloro, fluoro or $C_1$-$C_6$dialkyl-amino, via a sequence shown in scheme 10.

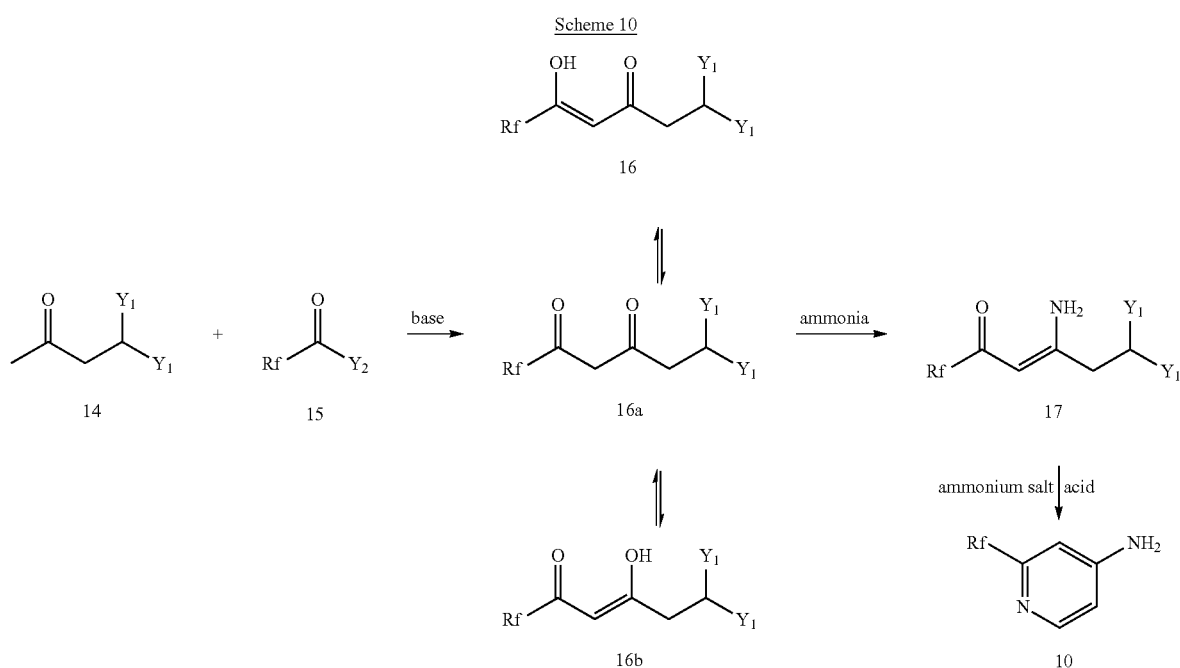

Compounds of formula 16, or a salt thereof, wherein Rf is $C_1$-$C_6$haloalkyl (preferably trifluoromethyl), and wherein $Y_1$ is independently halogen or $C_1$-$C_4$-alkoxy, or the two radicals $Y_1$ in a compound of formula 16 together form a group —O—$(CH_2)_m$—O—, wherein m is 2, 3 or 4, can be prepared by a condensation between compounds of formula 14, wherein $Y_1$ is independently halogen or $C_1$-$C_4$-alkoxy, or the two radicals $Y_1$ in a compound of formula 14 together form a group —O—$(CH_2)_m$—O—, wherein m is 2, 3 or 4, and compounds of formula 15, wherein Rf is $C_1$-$C_6$haloalkyl (preferably trifluoromethyl), and in which $Y_2$ is $C_1$-$C_6$alkoxy, chloro, fluoro or $C_1$-$C_6$dialkylamino, preferably under basic conditions. Preferably $Y_1$ is chlorine, methoxy or ethoxy, and $Y_2$ is methoxy or ethoxy. The condensation can be carried out in the presence of a base such as sodium hydride NaH, lithium diisopropylamide LDA, lithium hexamethyldisilazide LiHMDS, or the base is selected from alkali metal alcoholates, such as lithium, sodium and potassium methylate or ethylate or isopropylate or tert-butylate. Preferably the base is sodium methoxide NaOMe or sodium ethoxide NaOEt, in solvents such as toluene, tetrahydrofuran THF, N-methylpyrrolidone NMP or N,N-dimethylformamide DMF (or mixtures thereof), at temperatures between −78 to 120° C., preferably 0-100° C. In another embodiment, the base is dissolved in a monohydric $C_1$-$C_4$ alcohol, preferably ethanol or methanol, even more preferably methanol. The base sodium methylate dissolved in methanol is particularly preferred. Compounds of formula 16, or a salt thereof, may exist in different isomeric (for example E/Z isomers) and tautomeric forms (for example 16, 16a and/or 16b). This invention encompasses all such isomers and tautomers and mixtures thereof in all proportions.

Compounds of formula 17, wherein Rf is $C_1$-$C_6$haloalkyl (preferably trifluoromethyl), and wherein $Y_1$ is independently halogen or $C_1$-$C_4$-alkoxy, or the two radicals $Y_1$ in a compound of formula 17 together form a group —O—$(CH_2)_m$—O—, wherein m is 2, 3 or 4, can be prepared by reacting compounds of formula 16, or a salt thereof, or tautomers thereof, wherein Rf is $C_1$-$C_6$haloalkyl (preferably trifluoromethyl), and wherein $Y_1$ is independently halogen or $C_1$-$C_4$-alkoxy, or the two radicals $Y_1$ in a compound of formula 16 together form a group —O—$(CH_2)_m$—O—, wherein m is 2, 3 or 4, with ammonia $NH_3$ or an ammonia equivalent such as for example ammonium hydroxide $NH_4OH$, ammonium chloride $NH_4Cl$, ammonium bromide $NH_4Br$, ammonium acetate $NH_4OAc$, ammonium formate $NH_4HCO_2$, ammonium carbonate $(NH_4)_2CO_3$, ammonium sulfate and other $NH_3$ surrogates. Preferably, the ammonia source is gaseous ammonia. Preferably $Y_1$ is chlorine, methoxy or ethoxy. This transformation is preferably performed in suitable solvents (or diluents) such as amides, esters, ethers, nitriles and dimethylsulfoxide DMSO, particularly preferred are N,N-dimethylformamide, N,N-dimethylacetamide, N-methylpyrrolidinone, ethyl acetate, tetrahydrofuran, 1,4-dioxane, acetonitrile and dimethylsulfoxide or mixtures thereof, at temperatures ranging preferentially from room temperature to 180° C., more preferentially from 25° C. to 150° C., optionally under microwave irradiation or pressurized conditions using an autoclave. Advantageously the reaction is performed under elevated pressure of ammonia, for example 1-10 bar. Compounds of formula 17 may exist in different isomeric (for example E/Z isomers) and tautomeric forms. This invention covers all such isomers and tautomers and mixtures thereof in all proportions.

Compounds of the Formula 17

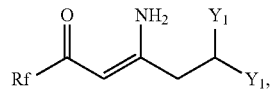

or tautomers and E/Z isomers thereof;

wherein Rf is $C_1$-$C_6$haloalkyl, preferably trifluoromethyl; and $Y_1$ is independently halogen or $C_1$-$C_4$-alkoxy, preferably chlorine, methoxy or ethoxy; or the two radicals $Y_1$ in a compound of formula 17 together form a group —O—$(CH_2)_m$—O—, in which m is 2, 3 or 4;

are novel and especially developed for the preparation of the compounds of formula (XI-A) of this invention. The compounds of formula 17 therefore constitute a further object of this invention. The preferred substituent definitions for the compounds of formula (XI-A) are also valid for the compounds of formula 17.

Even more preferably, $Y_1$ in compounds of the formula 17 is $C_1$-$C_4$-alkoxy, preferably methoxy or ethoxy.

Compounds of formula 10, or a salt thereof (such as a hydrohalide salt, preferably a hydrochloride or a hydrobromide salt, or any other equivalent salt), wherein Rf is $C_1$-$C_6$haloalkyl (preferably trifluoromethyl), can be prepared by cyclizing compounds of formula 17, wherein Rf is $C_1$-$C_6$haloalkyl (preferably trifluoromethyl), and wherein $Y_1$ is independently halogen or $C_1$-$C_4$-alkoxy, or the two radicals $Y_1$ in a compound of formula 17 together form a group —O—$(CH_2)_m$—O—, wherein m is 2, 3 or 4, in presence of a suitable ammonium salt, such as for example ammonium chloride $NH_4Cl$, ammonium bromide $NH_4Br$, ammonium acetate $NH_4OAc$, ammonium formate $NH_4HCO_2$, ammonium carbonate $(NH_4)_2CO_3$, or ammonium sulfate, preferably the ammonium source is ammonium acetate, in the presence of a suitable acid such as acetic acid or trifluoroacetic acid, preferably acetic acid, in a suitable solvent such as acetonitrile, propionitrile, 1,4-dioxane, N,N-dimethylformamide, dimethyl sulfoxide or N-methylpyrrolidinone, at temperatures between 50° C. and 200° C. Preferably $Y_1$ is chlorine, methoxy or ethoxy.

In the above sequence (scheme 10), compounds of formula 17 can be isolated and optionally purified. In a further aspect, the invention provides a process for the preparation of a compound of formula 10 as defined above comprising (scheme 10a)

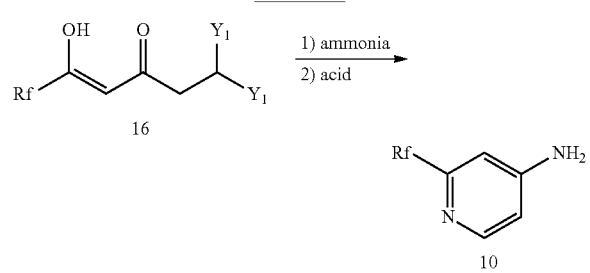

reacting a compound of formula 16 as defined above, or a salt thereof, or tautomers and E/Z isomers thereof, with ammonia as described above, preferably gaseous ammonia, preferably under pressure, and, without isolation of the in situ formed compound 17, submitting the reaction mixture directly to the cyclization step. In such a case, a suitable ammonium salt, preferably ammonium acetate, and a suitable acid such as acetic acid or trifluoroacetic acid, preferably acetic acid, may be added to the reaction mixture for the cyclization reaction. Heating is then proceeded at temperatures between 50° C. and 200° C.

Compounds of formula 14 are either known compounds, commercially available or can be prepared by known methods. 4,4-Dimethoxybutan-2-one, 4,4-diethoxybutan-2-one and 4,4-dichlorobutan-2-one are preferred examples of compounds of formula 14.

Compounds of formula 15 are either known compounds, commercially available or can be prepared by known methods. Methyltrifluoroacetate and ethyltrifluoroacetate are preferred examples of compounds of formula 15.

In schemes 8 to 10, Rf is preferably $C_1$-$C_6$fluoroalkyl, particularly preferred is trifluoromethyl.

In summary, the present invention also relates to novel methods of producing compounds of formula (XI-A) as shown in scheme 11.

The invention therefore also provides a process for the preparation of a compound of formula (XI-A)

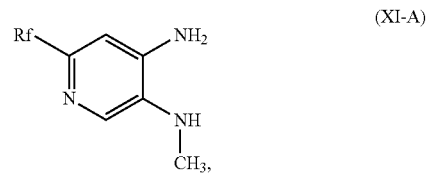

or a salt thereof;

wherein Rf is $C_1$-$C_6$haloalkyl, preferably trifluoromethyl;

comprising a. reacting a compound of formula 14

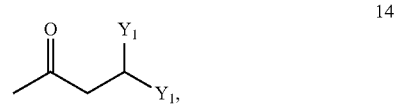

Scheme 11

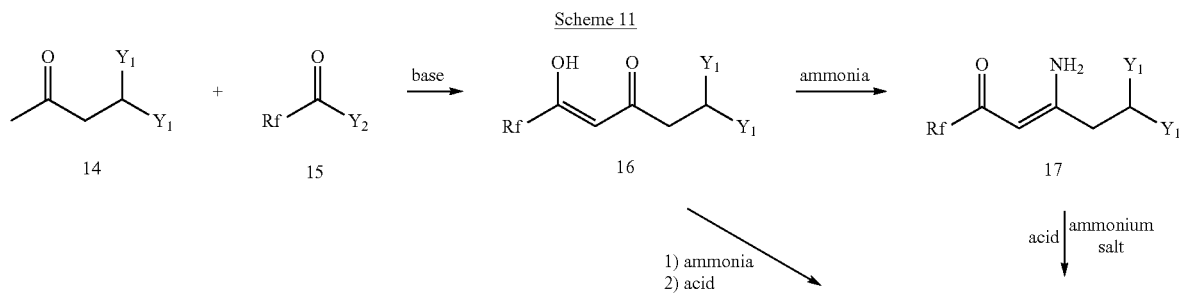

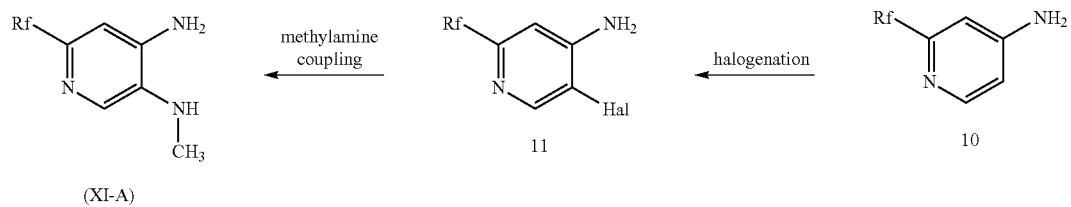

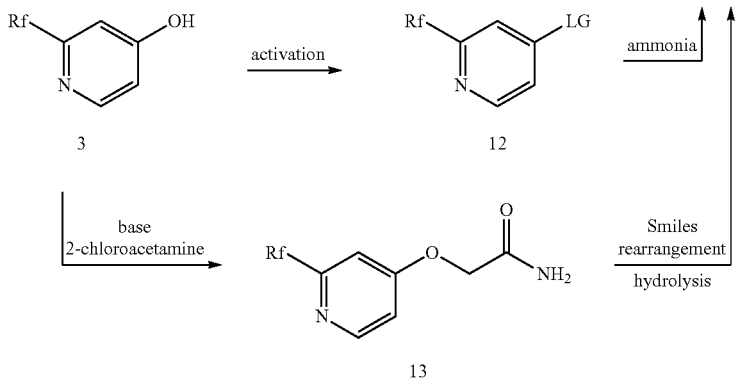

wherein $Y_1$ is independently halogen or $C_1$-$C_4$-alkoxy, preferably chlorine, methoxy or ethoxy; or
the two radicals $Y_1$ in a compound of formula 14 together form a group —O—(CH$_2$)$_m$—O—, wherein m is 2, 3 or 4;
with a compound of formula 15

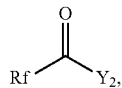
15 wherein Rf is $C_1$-$C_6$haloalkyl, preferably trifluoromethyl; and
$Y_2$ is $C_1$-$C_6$alkoxy, chloro, fluoro or $C_1$-$C_6$dialkylamino, preferably methoxy or ethoxy; in the presence of a base to produce a compound of formula 16

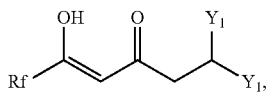
16 or a salt thereof;
or tautomers and E/Z isomers thereof;
wherein Rf is $C_1$-$C_6$haloalkyl, preferably trifluoromethyl; and
$Y_1$ is independently halogen or $C_1$-$C_4$-alkoxy, preferably chlorine, methoxy or ethoxy; or
the two radicals $Y_1$ in a compound of formula 16 together form a group —O—(CH$_2$)$_m$—O—, wherein m is 2, 3 or 4; and
b. reacting a compound of formula 16

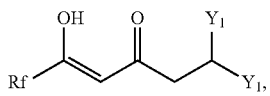
16 or a salt thereof;
or tautomers and E/Z isomers thereof;
wherein Rf is $C_1$-$C_6$haloalkyl, preferably trifluoromethyl; and
$Y_1$ is independently halogen or $C_1$-$C_4$-alkoxy, preferably chlorine, methoxy or ethoxy; or
the two radicals $Y_1$ in a compound of formula 16 together form a group —O—(CH$_2$)$_m$—O—, wherein m is 2, 3 or 4;
with ammonia, or a salt thereof;
to produce a compound of formula 17

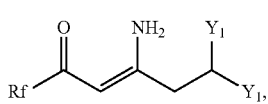
17 or tautomers and E/Z isomers thereof;
wherein Rf is $C_1$-$C_6$haloalkyl, preferably trifluoromethyl; and
$Y_1$ is independently halogen or $C_1$-$C_4$-alkoxy, preferably chlorine, methoxy or ethoxy; or
the two radicals $Y_1$ in a compound of formula 17 together form a group —O—(CH$_2$)$_m$—O—, in which m is 2, 3 or 4; and c. reacting a compound of formula 17

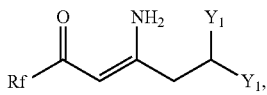
17 or tautomers and E/Z isomers thereof;
wherein Rf is $C_1$-$C_6$haloalkyl, preferably trifluoromethyl; and
$Y_1$ is independently halogen or $C_1$-$C_4$-alkoxy, preferably chlorine, methoxy or ethoxy; or
the two radicals $Y_1$ in a compound of formula 17 together form a group —O—(CH$_2$)$_m$—O—, in which m is 2, 3 or 4;
with an ammonium salt;
in the presence of an acid to produce a compound of formula 10

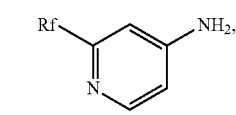
10 or a salt thereof;
wherein Rf is $C_1$-$C_6$haloalkyl, preferably trifluoromethyl; and
d. reacting a compound of formula 10

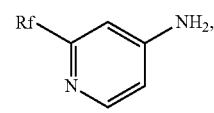
10 or a salt thereof;
wherein Rf is $C_1$-$C_6$haloalkyl, preferably trifluoromethyl;
with a halogenating agent;
to produce a compound of formula 11

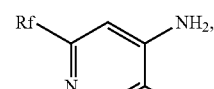
11 or a salt thereof;
wherein Rf is $C_1$-$C_6$haloalkyl, preferably trifluoromethyl; and
Hal is a halogen, preferably chlorine, bromine or iodine, more preferably bromine; and
e. reacting a compound of formula 11

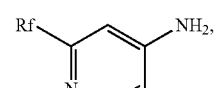
11 or a salt thereof;
wherein Rf is $C_1$-$C_6$haloalkyl, preferably trifluoromethyl; and
Hal is a halogen, preferably chlorine, bromine or iodine, more preferably bromine;
with methylamine, or a salt thereof;
to produce the compound of formula (XI-A)

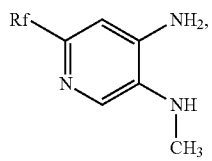

(XI-A)

or a salt thereof;
wherein Rf is $C_1$-$C_6$haloalkyl, preferably trifluoromethyl.

Preferably step a. is performed in the presence of a suitable base. Examples of suitable bases are given above.

Preferably the ammonia source in step b. is gaseous ammonia. Even more preferably, the reaction is performed under elevated pressure of ammonia.

Preferably step c. is performed in the presence of a suitable ammonium salt. Examples of suitable ammonium salts are given above. Preferably, the ammonium source is ammonium acetate. Preferably step c. is performed in the presence of a suitable acid. Examples of suitable acids are given above. Preferably, the acid is acetic acid.

Preferably the halogenating agent in step d. is a brominating agent. Examples of brominating agents are given above. Even more preferably the brominating agent is the combination of ammonium bromide and hydrogen peroxide, performed in acetic acid as solvent. In a further aspect the invention provides a process for the preparation of a compound of formula 11 comprising performing step d. as defined above, whereby an acetic acid solution of compound of formula 10 is heated
i. in the presence of ammonium bromide to form a reaction mixture; and
ii. the reaction mixture is treated with an aqueous hydrogen peroxide solution.

Preferably step e. is performed in the presence of a suitable copper catalyst, and optionally in the presence of a suitable ligand. Examples of suitable copper catalysts and optional ligands are given above. Preferably, gaseous methylamine or an aqueous solution (strength of 10 to 40% by weight) of methylamine are used in step e.

In a further aspect, the invention also provides a process for the preparation of a compound of formula 10 as defined above comprising
b1. reacting a compound of formula 16

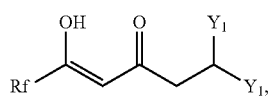

16 or a salt thereof;
or tautomers and E/Z isomers thereof;
wherein Rf is $C_1$-$C_6$haloalkyl, preferably trifluoromethyl; and
$Y_1$ is independently halogen or $C_1$-$C_4$-alkoxy, preferably chlorine, methoxy or ethoxy; or the two radicals $Y_1$ in a compound of formula 16 together form a group —O—$(CH_2)_m$—O—, wherein m is 2, 3 or 4;
with ammonia, or a salt thereof;
to produce a reaction mixture; and
b2. reacting said mixture directly
with an ammonium salt;
in the presence of an acid to produce the compound of formula 10

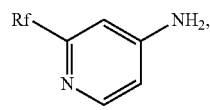

10 or a salt thereof;
wherein Rf is $C_1$-$C_6$haloalkyl, preferably trifluoromethyl.

Preferably the ammonia source in step b1. is gaseous ammonia. Even more preferably, the reaction is performed under elevated pressure of ammonia.

Preferably step b2. is performed in the presence of a suitable ammonium salt. Examples of suitable ammonium salts are given above. Preferably, the ammonium source is ammonium acetate. Preferably step b2. is performed in the presence of a suitable acid. Examples of suitable acids are given above. Preferably, the acid is acetic acid.

The sequence (scheme 11) towards compounds of formula 10, wherein Rf is $C_1$-$C_6$haloalkyl (preferably trifluoromethyl), from reactants 14 and 15 as described above is particularly advantageous as it has a lower number of steps and it avoids the activation of the 4-hydroxy group in a compound of formula 3 which is otherwise decreasing the atom economy and generating stoichiometric waste in the substitution step. Compounds of formula 3 and 12, and a process for transforming 3 into 12 are described in WO 2011/161612.

The direct formation of compounds of formula 10 from compounds of formula 16 without isolation of 17 under above described conditions may be seen surprising as similar conditions disclosed in WO 2011/161612 provided rather the pyridin-4-ol compounds of formula 3.

Alternatively, compounds of the formula I, wherein Q is $Q_2$, defining compounds of the formula I-$Q_2$, wherein X, $R_1$, n, $R_7$, $R_8$, A, $G_3$ and $R_2$ are as defined in formula I Scheme 12

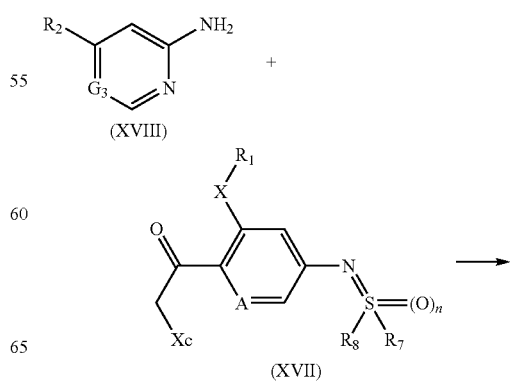

(XVIII)

(XVII)

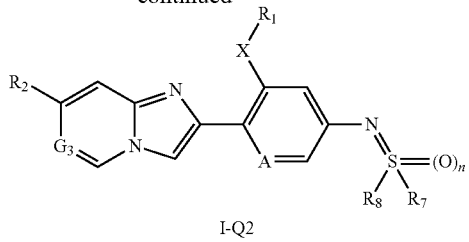

I-Q2 may be prepared (scheme 12) by condensing compounds of the formula (XVII), wherein X, $R_1$, n, $R_7$, $R_8$ and A are as defined in formula I, and in which Xc is is a leaving group such as, for example, chlorine, bromine or iodine (preferably chlorine or bromine), with compounds of the formula (XVIII), wherein $G_3$ and $R_2$ are as defined in formula I, in an inert solvent, for example ethanol or acetonitrile, optionally in the presence of a suitable base, such as sodium, potassium or cesium carbonate, at temperatures between 80 and 150° C., optionally under microwave heating conditions. Such processes have been described previously, for example, in WO 2012/49280 or WO 2003/031587. Compounds of formula (XVIII), wherein $G_3$ and $R_2$ are as defined in formula I, are either known compounds, commercially available or may be prepared by known methods known to those skilled in the art.

Compounds of the formula (XVII), wherein X, $R_1$, n, $R_7$, $R_8$ and A are as defined in formula I, and in which Xc is is a leaving group such as, for example, chlorine, bromine or iodine (preferably chlorine or bromine), thereof, at temperatures between 0° C. and 150° C., preferably between room temperature and 120° C., optionally under microwave heating conditions. Such processes have been described previously, for example, in WO2016/071214.

Compounds of formula (XIXa), wherein X, $R_1$, $R_7$, $R_8$ and A are as defined in formula I, may be prepared by reacting compounds of formula (XX), wherein X, $R_1$ and A are as defined in formula I, and in which Xa is a leaving group such as, for example, chlorine, bromine or iodine (preferably chlorine or bromine), or an aryl-, alkyl- or haloalkylsulfonate such as trifluoromethanesulfonate, with a reagent HN=S(O)$R_7R_8$ of formula III, wherein $R_7$ and $R_8$ are as defined in formula I, under conditions already described above (see scheme 1, transformation of compounds II into Ia).

Compounds of formula (XIXa), wherein X, $R_1$, $R_7$, $R_8$ and A are as defined in formula I, may also be prepared by oxidation of compounds of formula (XIXb), wherein X, $R_1$, $R_7$, $R_8$ and A are as defined in formula I, under conditions already described above (see scheme 2a, transformation of compounds Ib into Ia). Alternatively, compounds of formula (XIXa), wherein X, $R_1$, $R_7$, $R_8$ and A are as defined in formula I, may also be prepared from compounds of formula (XXI), wherein X, $R_1$ and A are as defined in formula I, under conditions already described above (see scheme 2a, transformation of compounds IV into Ia).

Compounds of formula (XIXb), wherein X, $R_1$, $R_7$, $R_8$ and A are as defined in formula I, may be prepared by reacting compounds of formula (XXI), wherein X, $R_1$ and A are as defined in formula I, with a reagent S(O)$R_7R_8$ of Scheme 13

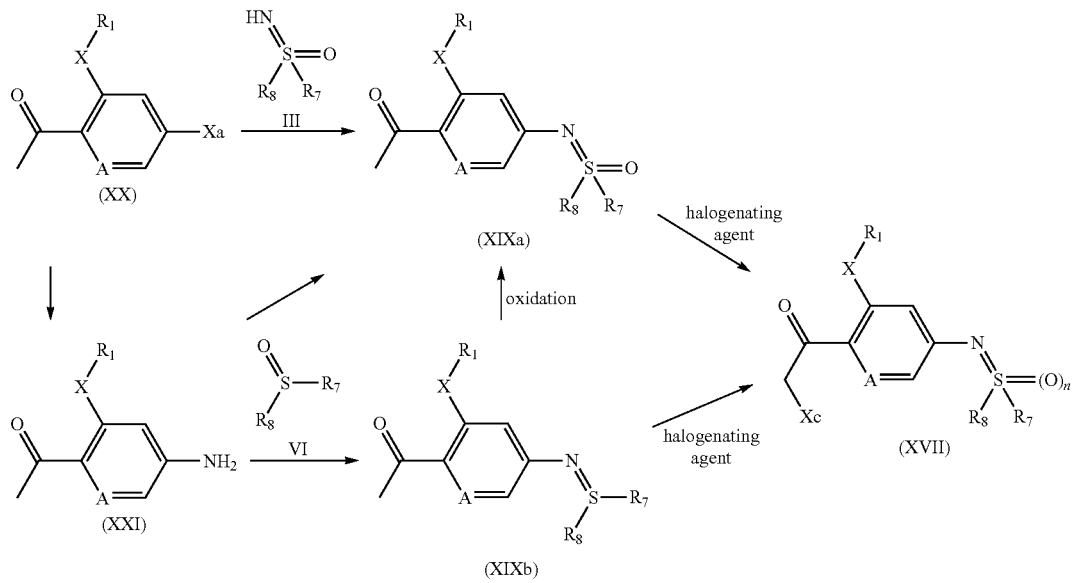

may be prepared (scheme 13) by treatment of either compounds of formula (XIXa) or compounds of formula (XIXb), wherein X, $R_1$, $R_7$, $R_8$ and A are as defined in formula I, with a halogenating agent ("Xc$^+$" source), e.g. N-bromosuccinimide, N-iodosuccinimide, N-chlorosuccinimide, $I_2$, $CuBr_2$, $Br_2$ in acetic acid, PhNMe$_3^+$Br$_3^-$, typically in a solvent such as methanol, acetonitrile, tetrahydrofuran, ethyl acetate, chloroform or dichloromethane, or mixtures formula VI, wherein $R_7$ and $R_8$ are as defined in formula I, under conditions already described above (see scheme 2b, transformation of compounds IV into Ib). Alternatively, compounds of formula (XIXb), wherein X, $R_1$, $R_7$, $R_8$ and A are as defined in formula I, may be prepared by reacting compounds of formula (XXI), wherein X, $R_1$ and A are as defined in formula I, with a reagent SR$_7R_8$ of formula V, wherein $R_7$ and $R_8$ are as defined in formula I, under conditions already described above (see scheme 2a, transformation of compounds IV into Ib).

Compounds of formula (XXI), wherein X, $R_1$ and A are as defined in formula I, may be prepared from compounds of formula (XX), wherein X, $R_1$ and A are as defined in formula I, and in which Xa is a leaving group such as, for example, chlorine, bromine or iodine (preferably chlorine or bromine), or an aryl-, alkyl- or haloalkylsulfonate such as trifluoromethanesulfonate, under conditions already described above (see scheme 3, transformation of compounds II into IV).

Compounds of formula (XX), wherein X, $R_1$ and A are as defined in formula I, and wherein Xa is a leaving group such as, for example, chlorine, bromine or iodine, or an aryl-, alkyl- or haloalkylsulfonate such as trifluoromethanesulfonate, in particular those compounds wherein Xa is a halogen (even more preferably chlorine, bromine or iodine; particularly preferred is chlorine or bromine), are either known compounds, commercially available or may be prepared by known methods, described in the literature, as for example in WO 2016/071214.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula I can be converted in a manner known per se into another compound of formula I by replacing one or more substituents of the starting compound of formula I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties can be obtained in free form or in the form of salts.

The compounds of formula I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diastereomers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl celulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from J. Med. Chem., 32 (12), 2561-73, 1989 or WO 00/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the following Tables 1 to 9 below can be prepared according to the methods described above. The examples which follow are intended to illustrate the invention and show preferred compounds of formula I.

Table 1:
This table discloses the 14 compounds 1.001 to 1.014 of the formula I-1a:

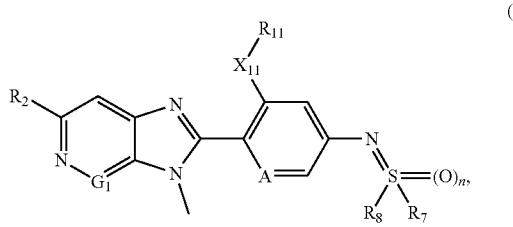

(I-1a)

wherein $X_{11}$ is S, and A, $R_{11}$, $G_1$, $R_2$, n, $R_7$ and $R_8$ are as defined below:

TABLE 1

| Comp. No | A | $R_{11}$ | $G_1$ | $R_2$ | n | $R_7$ | $R_8$ |
|---|---|---|---|---|---|---|---|
| 1.001 | N | —CH$_2$CH$_3$ | CH | CF$_3$ | 1 | CH$_3$ | CH$_3$ |
| 1.002 | N | —CH$_2$CH$_3$ | CH | CF$_3$ | 1 | CH$_3$ | cycloC3 |
| 1.003 | N | —CH$_2$CH$_3$ | N | CF$_3$ | 1 | CH$_3$ | CH$_3$ |
| 1.004 | N | —CH$_2$CH$_3$ | N | CF$_3$ | 1 | CH$_3$ | cycloC3 |
| 1.005 | N | —CH$_2$CH$_3$ | CH | CF$_3$ | 1 | CH$_2$CH$_3$ | CH$_2$CH$_3$ |
| 1.006 | N | —CH$_2$CH$_3$ | CH | CF$_3$ | 1 | —CH$_2$CH$_2$CH$_2$— | |
| 1.007 | N | —CH$_2$CH$_3$ | CH | CF$_3$ | 1 | —CH$_2$CH$_2$CH$_2$CH$_2$— | |
| 1.008 | N | —CH$_2$CH$_3$ | CH | CF$_3$ | 1 | —CH$_2$CH$_2$OCH$_2$CH$_2$— | |
| 1.009 | N | —CH$_2$CH$_3$ | CH | CF$_3$ | 0 | CH$_3$ | CH$_3$ |
| 1.010 | N | —CH$_2$CH$_3$ | N | CF$_3$ | 1 | —CH$_2$CH$_2$OCH$_2$CH$_2$— | |
| 1.011 | CH | —CH$_2$CH$_3$ | N | CF$_3$ | 1 | —CH$_2$CH$_2$OCH$_2$CH$_2$— | |
| 1.012 | N | —CH$_2$CH$_3$ | CH | CF$_3$ | 0 | CH$_2$CH$_3$ | CH$_2$CH$_3$ |
| 1.013 | N | —CH$_2$CH$_3$ | CH | CF$_3$ | 1 | CH$_3$ | CH$_2$CH$_3$ |
| 1.014 | CH | —CH$_2$CH$_3$ | CH | CF$_3$ | 1 | —CH$_2$CH$_2$OCH$_2$CH$_2$— | | and the N-oxides of the compounds of Table 1. CycloC3 is cyclopropyl.

Table 2:
This table discloses the 14 compounds 2.001 to 2.014 of the formula I-1a, wherein $X_{11}$ is SO, and A, $R_{11}$, $G_1$, $R_2$, n, $R_7$ and $R_8$ are as defined in Table 1.

Table 3:
This table discloses the 14 compounds 3.001 to 3.014 of the formula I-1a, wherein $X_{11}$ is SO$_2$, and A, $R_{11}$, $G_1$, $R_2$, n, $R_7$ and $R_8$ are as defined in Table 1.

Table 4:
This table discloses the 9 compounds 4.001 to 4.009 of the formula I-2a:

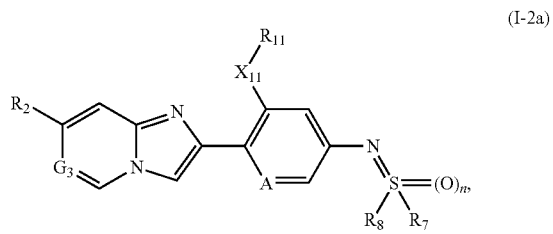

(I-2a)

wherein $X_{11}$ is S, and A, $R_{11}$, $G_3$, $R_2$, n, $R_7$ and $R_8$ are as defined below:

TABLE 4

| Comp. No | A | $R_{11}$ | $G_3$ | $R_2$ | n | $R_7$ | $R_8$ |
|---|---|---|---|---|---|---|---|
| 4.001 | N | —CH$_2$CH$_3$ | CH | CF$_3$ | 1 | CH$_3$ | CH$_3$ |
| 4.002 | N | —CH$_2$CH$_3$ | CH | CF$_3$ | 1 | CH$_3$ | cycloC3 |
| 4.003 | N | —CH$_2$CH$_3$ | N | CF$_3$ | 1 | CH$_3$ | CH$_3$ |
| 4.004 | N | —CH$_2$CH$_3$ | N | CF$_3$ | 1 | CH$_3$ | cycloC3 |
| 4.005 | CH | —CH$_2$CH$_3$ | N | CF$_3$ | 1 | CH$_3$ | CH$_3$ |
| 4.006 | CH | —CH$_2$CH$_3$ | N | CF$_3$ | 1 | CH$_3$ | cycloC3 |
| 4.007 | N | —CH$_2$CH$_3$ | N | CF$_3$ | 1 | CH$_3$ | 4-CH$_3$-phenyl |
| 4.008 | N | —CH$_2$CH$_3$ | N | CF$_3$ | 1 | —CH$_2$CH$_2$CH$_2$— | |
| 4.009 | N | —CH$_2$CH$_3$ | N | CF$_3$ | 1 | —CH$_2$CH$_2$OCH$_2$CH$_2$— | | and the N-oxides of the compounds of Table 4. CycloC3 is cyclopropyl.

Table 5:
This table discloses the 9 compounds 5.001 to 5.009 of the formula I-2a, wherein $X_{11}$ is SO, and A, $R_{11}$, $G_3$, $R_2$, n, $R_7$ and $R_8$ are as defined in Table 4.

Table 6:
This table discloses the 9 compounds 6.001 to 6.009 of the formula I-2a, wherein $X_{11}$ is SO$_2$, and A, $R_{11}$, $G_3$, $R_2$, n, $R_7$ and $R_8$ are as defined in Table 4.

Table 7:
This table discloses the 4 compounds 7.001 to 7.004 of the formula I-3a:

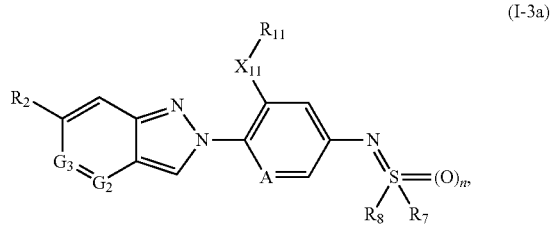

(I-3a)

wherein $X_{11}$ is S, and A, $R_{11}$, $G_2$, $G_3$, $R_2$, n, $R_7$ and $R_8$ are as defined below:

TABLE 7

| Comp. No | A | $R_{11}$ | $G_2$ | $G_3$ | $R_2$ | n | $R_7$ | $R_8$ |
|---|---|---|---|---|---|---|---|---|
| 7.001 | N | —CH$_2$CH$_3$ | CH | N | CF$_3$ | 1 | CH$_3$ | CH$_3$ |
| 7.002 | N | —CH$_2$CH$_3$ | N | CH | CF$_3$ | 1 | CH$_3$ | CH$_3$ |

TABLE 7-continued

| Comp. No | A | $R_{11}$ | $G_2$ | $G_3$ | $R_2$ | n | $R_7$ | $R_8$ |
|---|---|---|---|---|---|---|---|---|
| 7.003 | N | —CH$_2$CH$_3$ | CH | N | CF$_3$ | 1 | CH$_3$ | cycloC3 |
| 7.004 | N | —CH$_2$CH$_3$ | N | CH | CF$_3$ | 1 | CH$_3$ | cycloC3 | and the N-oxides of the compounds of Table 7. CycloC3 is cyclopropyl.

Table 8:

This table discloses the 4 compounds 8.001 to 8.004 of the formula I-3a, wherein $X_{11}$ is SO, and A, $R_{11}$, $G_2$, $G_3$, $R_2$, n, $R_7$ and $R_8$ are as defined in Table 7.

Table 9:

This table discloses the 4 compounds 9.001 to 9.004 of the formula I-3a, wherein $X_{11}$ is SO$_2$, and A, $R_{11}$, $G_2$, $G_3$, $R_2$, n, $R_7$ and $R_8$ are as defined in Table 7.

The compounds of formula I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order *Acarina*. The insecticidal or acaricidal activity of the active ingredients according to the invention can manifest itself directly, i. e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

Examples of the abovementioned animal pests are:

from the order *Acarina*, for example,

*Acalitus* spp, *Aculus* spp, *Acaricalus* spp, *Aceria* spp, *Acarus siro*, *Amblyomma* spp., *Argas* spp., *Boophilus* spp., *Brevipalpus* spp., *Bryobia* spp, *Calipitrimerus* spp., *Chorioptes* spp., *Dermanyssus gallinae*, *Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.;

from the order Coleoptera, for example,

*Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp, *Phlyctinus* spp., *Popillia* spp., *Psylliodes* spp., *Rhyssomatus aubtilis*, *Rhizopertha* spp., *Scarabeidae*, *Sitophilus* spp., *Sitotroga* spp., *Somaticus* spp, *Sphenophorus* spp, *Sternechus subsignatus*, *Tenebrio* spp., *Tribolium* spp. and *Trogoderma* spp.;

from the order Diptera, for example,

*Aedes* spp., *Anopheles* spp, *Antherigona soccata*, *Bactrocea oleae*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *Tannia* spp. and *Tipula* spp.;

from the order Hemiptera, for example,

*Acanthocoris scabrator*, *Acrosternum* spp, *Adelphocoris lineolatus*, *Amblypelta nitida*, *Bathycoelia thalassina*, *Blissus* spp, *Cimex* spp., *Clavigralla tomentosicollis*, *Creontiades* spp, *Distantiella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilellus*, *Leptocorisa* spp., *Lygus* spp, *Margarodes* spp., *Murgantia histrionic*, *Neomegalotomus* spp, *Nesidiocoris tenuis*, *Nezara* spp., *Nysius simulans*, *Oebalus insularis*, *Piesma* spp., *Piezodorus* spp, *Rhodnius* spp., *Sahlbergella singularis*, *Scaptocoris castanea*, *Scotinophara* spp., *Thyanta* spp, *Triatoma* spp., *Vatiga illudens*;

*Acyrthosium pisum*, *Adalges* spp, *Agalliana ensigera*, *Agonoscena targionii*, *Aleurodicus* spp, *Aleurocanthus* spp, *Aleurolobus barodensis*, *Aleurothrixus floccosus*, *Aleyrodes brassicae*, *Amarasca biguttula*, *Amritodus atkinsoni*, *Aonidiella* spp., *Aphididae*, *Aphis* spp., *Aspidiotus* spp., *Aulacorthum solani*, *Bactericera cockerelli*, *Bemisia* spp, *Brachycaudus* spp, *Brevicoryne brassicae*, *Cacopsylla* spp, *Cavariella aegopodii* Scop., *Ceroplaster* spp., *Chrysomphalus aonidium*, *Chrysomphalus dictyospermi*, *Cicadella* spp, *Cofana spectra*, *Cryptomyzus* spp, *Cicadulina* spp, *Coccus hesperidum*, *Dalbulus maidis*, *Dialeurodes* spp, *Diaphorina citri*, *Diuraphis noxia*, *Dysaphis* spp, *Empoasca* spp., *Eriosoma larigerum*, *Erythroneura* spp., *Gascardia* spp., *Glycaspis brimblecombei*, *Hyadaphis pseudobrassicae*, *Hyalopterus* spp, *Hyperomyzus pallidus*, *Idioscopus clypealis*, *Jacobiasca lybica*, *Laodelphax* spp., *Lecanium corni*, *Lepidosaphes* spp., *Lopaphis erysimi*, *Lyogenys maidis*, *Macrosiphum* spp., *Mahanarva* spp, *Metcalfa pruinosa*, *Metopolophium dirhodum*, *Myndus crudus*, *Myzus* spp., *Neotoxoptera* sp, *Nephotettix* spp., *Nilaparvata* spp., *Nippolachnus piri* Mats, *Odonaspis ruthae*, *Oregma lanigera Zehnter*, *Parabemisia myricae*, *Paratrioza cockerelli*, *Parlatoria* spp., *Pemphigus* spp., *Peregrinus maidis*, *Perkinsiella* spp, *Phorodon humuli*, *Phylloxera* spp, *Planococcus* spp., *Pseudaulacaspis* spp., *Pseudococcus* spp., *Pseudatomoscelis seriatus*, *Psylla* spp., *Pulvinaria aethiopica*, *Quadraspidiotus* spp., *Quesada gigas*, *Recilia dorsalis*, *Rhopalosiphum* spp., *Saissetia* spp., *Scaphoideus* spp., *Schizaphis* spp., *Sitobion* spp., *Sogatella furcifera*, *Spissistilus festinus*, *Tarophagus Proserpina*, *Toxoptera* spp, *Trialeurodes* spp, *Tridiscus sporoboli*, *Trionymus* spp, *Trioza erytreae*, *Unaspis citri*, *Zygina flammigera*, *Zyginidia scutellaris*;

from the order Hymenoptera, for example,

*Acromyrmex*, *Arge* spp, *Atta* spp., *Cephus* spp., *Diprion* spp., *Diprionidae*, *Gilpinia polytoma*, *Hoplo-campa* spp., *Lasius* spp., *Monomorium pharaonis*, *Neodiprion* spp., *Pogonomyrmex* spp, *Slenopsis invicta*, *Solenopsis* spp. and *Vespa* spp.;

from the order Isoptera, for example,

*Coptotermes* spp, *Corniternes cumulans*, *Incisitermes* spp, *Macrotermes* spp, *Mastotermes* spp, *Microtermes* spp, *Reticulitermes* spp.; *Solenopsis geminate* from the order Lepidoptera, for example,

*Acleris* spp., *Adoxophyes* spp., *Aegeria* spp., *Agrotis* spp., *Alabama argillaceae*, *Amylois* spp., *Anticarsia gemmatalis*, *Archips* spp., *Argyresthia* spp, *Argyrotaenia* spp., *Autographa* spp., *Bucculatrix thurberiella*, *Busseola fusca*, *Cadra cautella*, *Carposina nipponensis*, *Chilo* spp., *Choristoneura* spp., *Chrysoteuchia topiaria*, *Clysia ambiguella*, *Cnaphalocrocis* spp., *Cnephasia* spp., *Cochylis* spp., *Coleophora* spp., *Colias lesbia*, *Cosmophila flava*, *Crambus* spp, *Crocidolomia binotalis*, *Cryptophlebia leucotreta*, *Cydalima perspectalis*, *Cydia* spp., *Diaphania perspectalis*, *Diatraea* spp., *Diparopsis castanea*, *Earias* spp., *Eldana saccharina*, *Ephestia* spp., *Epinotia* spp, *Estigmene acrea*, *Etiella zinckinella*, *Eucosma* spp., *Eupoecilia ambiguella*, *Euproctis* spp., *Euxoa* spp., *Feltia jaculiferia*, *Gra-pholita* spp., *Hedya nubiferana*, *Heliothis* spp., *Hellula undalis*, *Herpetogramma* spp, *Hyphantria cunea*, *Keiferia lycopersicella*, *Lasmopalpus lignosellus*, *Leucoptera scitella*, *Lithocollethis* spp., *Lobesia botrana*, *Loxostege bifidalis*, *Lymantria* spp., *Lyonetia* spp., *Malacosoma* spp., *Mamestra brassicae*, *Manduca sexta*, *Mythimna* spp, *Noctua* spp, *Operophtera* spp., *Orniodes indica*, *Ostrinia nubilalis*, *Pammene* spp., *Pandemis* spp., *Panolis flammea*, *Papaipema nebris*, *Pectinophora gossypi-ela*, *Perileucoptera coffeella*, *Pseudaletia unipuncta*, *Phthorimaea operculella*, *Pieris rapae*, *Pieris* spp., *Plutella xylostella*, *Prays* spp., *Pseudoplusia* spp, *Rachiplusia nu*, *Richia albicosta*, *Scirpophaga* spp., *Sesamia* spp., *Sparganothis* spp., *Spodoptera* spp., *Sylepta derogate*, *Synanthedon* spp., *Thaumetopoea* spp., *Tortrix* spp., *Trichoplusia ni*, *Tuta absoluta*, and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae*, *Locusta* spp., *Neocurtilla hexadactyla*, *Periplaneta* spp., *Scapteriscus* spp, and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis*;

from the order Thysanoptera, for example,

*Calliothrips phaseoli*, *Frankliniella* spp., *Heliothrips* spp, *Hercinothrips* spp., *Parthenothrips* spp, *Scirtothrips aurantii*, *Sericothrips variabilis*, *Taeniothrips* spp., *Thrips* spp;

from the order Thysanura, for example, *Lepisma saccharina*.

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family and latex plants.

The compositions and/or methods of the present invention may be also used on any ornamental and/or vegetable crops, including flowers, shrubs, broad-leaved trees and evergreens.

For example the invention may be used on any of the following ornamental species: *Ageratum* spp., *Alonsoa* spp., *Anemone* spp., *Anisodontea capsenisis*, *Anthemis* spp., *Antirrhinum* spp., *Aster* spp., *Begonia* spp. (e.g. *B. elatior*, *B. semperflorens*, *B. tubéreux*), *Bougainvillea* spp., *Brachycome* spp., *Brassica* spp. (ornamental), *Calceolaria* spp., *Capsicum annuum*, *Catharanthus roseus*, *Canna* spp., *Centaurea* spp., *Chrysanthemum* spp., *Cineraria* spp. (*C. maritime*), *Coreopsis* spp., *Crassula coccinea*, *Cuphea ignea*, *Dahlia* spp., *Delphinium* spp., *Dicentra spectabilis*, *Dorotheantus* spp., *Eustoma grandiflorum*, *Forsythia* spp., *Fuchsia* spp., *Geranium gnaphalium*, *Gerbera* spp., *Gomphrena globosa*, *Heliotropium* spp., *Helianthus* spp., *Hibiscus* spp., *Hortensia* spp., *Hydrangea* spp., *Hypoestes phyllostachya*, *Impatiens* spp. (*I. Walleriana*), *Iresines* spp., *Kalanchoe* spp., *Lantana camara*, *Lavatera trimestris*, *Leonotis leonurus*, *Lilium* spp., *Mesembryanthemum* spp., *Mimulus* spp., *Monarda* spp., *Nemesia* spp., *Tagetes* spp., *Dianthus* spp. (carnation), *Canna* spp., *Oxalis* spp., *Bellis* spp., *Pelargonium* spp. (*P. peltatum*, *P. Zonale*), *Viola* spp. (pansy), *Petunia* spp., *Phlox* spp., *Plecthranthus* spp., *Poinsettia* spp., *Parthenocissus* spp. (*P. quinquefolia*, *P. tricuspidata*), *Primula* spp., *Ranunculus* spp., *Rhododendron* spp., *Rosa* spp. (rose), *Rudbeckia* spp., *Saintpaulia* spp., *Salvia* spp., *Scaevola aemola*, *Schizanthus wisetonensis*, *Sedum* spp., *Solanum* spp., *Surfinia* spp., *Tagetes* spp., *Nicotinia* spp., *Verbena* spp., *Zinnia* spp. and other bedding plants.

For example the invention may be used on any of the following vegetable species: *Allium* spp. (*A. sativum*, *A. cepa*, *A. oschaninii*, *A. Porrum*, *A. ascalonicum*, *A. fistulosum*), *Anthriscus cerefolium*, *Apium graveolus*, *Asparagus officinalis*, *Beta vulgarus*, *Brassica* spp. (*B. Oleracea*, *B. Pekinensis*, *B. rapa*), *Capsicum annuum*, *Cicer arietinum*, *Cichorium endivia*, *Cichorum* spp. (*C. intybus*, *C. endivia*), *Citrillus lanatus*, *Cucumis* spp. (*C. sativus*, *C. melo*), *Cucurbita* spp. (*C. pepo*, *C. maxima*), *Cyanara* spp. (*C. scolymus*, *C. cardunculus*), *Daucus carota*, *Foeniculum vulgare*, *Hypericum* spp., *Lactuca sativa*, *Lycopersicon* spp. (*L. esculentum*, *L. lycopersicum*), *Mentha* spp., *Ocimum basilicum*, *Petroselinum crispum*, *Phaseolus* spp. (*P. vulgaris*, *P. coccineus*), *Pisum sativum*, *Raphanus sativus*, *Rheum rhaponticum*, *Rosemarinus* spp., *Salvia* spp., *Scorzonera hispanica*, *Solanum melongena*, *Spinacea oleracea*, *Valerianella* spp. (*V. locusta*, *V. eriocarpa*) and *Vicia faba*.

Preferred ornamental species include African violet, Begonia, Dahlia, Gerbera, Hydrangea, Verbena, Rosa, Kalanchoe, Poinsettia, Aster, Centaurea, Coreopsis, Delphinium, Monarda, Phlox, Rudbeckia, Sedum, Petunia, Viola, Impatiens, Geranium, Chrysanthemum, Ranunculus, Fuchsia, Salvia, Hortensia, rosemary, sage, St. Johnswort, mint, sweet pepper, tomato and cucumber.

The active ingredients according to the invention are especially suitable for controlling *Aphis craccivora*, *Diabrotica balteata*, *Heliothis virescens*, *Myzus persicae*, *Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatos) and *Chilo supressalis* (preferably in rice).

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatos) and *Chilo supressalis* (preferably in rice).

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla, Meloidogyne incognita, Meloidogyne javanica, Meloidogyne arenaria* and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

The compounds of the invention may also have activity against the molluscs. Examples of which include, for example, Ampullariidae; *Arion* (*A. ater, A. circumscriptus, A. hortensis, A. rufus*); Bradybaenidae (*Bradybaena fruticum*); *Cepaea* (*C. hortensis, C. Nemoralis*); ochlodina; *Deroceras* (*D. agrestis, D. empiricorum, D. laeve, D. reticulatum*); *Discus* (*D. rotundatus*); Euomphalia; *Galba* (*G. trunculata*); *Helicelia* (*H. itala, H. obvia*); Helicidae *Helicigona arbustorum*); Helicodiscus; *Helix* (*H. aperta*); *Limax* (*L. cinereoniger, L. flavus, L. marginatus, L. maximus, L. tenellus*); *Lymnaea; Milax* (*M. gagates, M. marginatus, M. sowerbyi*); *Opeas; Pomacea* (*P. canaticulata*); *Vallonia* and Zanitoides.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810). Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cry1-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1 Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:
1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.
7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defense (so-called "plant disease resistance genes", as described in WO 03/000906).

Further areas of use of the compositions according to the invention are the protection of stored goods and store rooms and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO2006/128870, EP 1724392, WO2005113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables A and B:

TABLE A

Examples of exotic woodborers of economic importance.

| Family | Species | Host or Crop Infested |
|---|---|---|
| Buprestidae | Agrilus planipennis | Ash |
| Cerambycidae | Anoplura glabripennis | Hardwoods |
| Scolytidae | Xylosandrus crassiusculus | Hardwoods |
|  | X. mutilatus | Hardwoods |
|  | Tomicus piniperda | Conifers |

TABLE B

Examples of native woodborers of economic importance.

| Family | Species | Host or Crop Infested |
|---|---|---|
| Buprestidae | Agrilus anxius | Birch |
|  | Agrilus politus | Willow, Maple |
|  | Agrilus sayi | Bayberry, Sweetfern |
|  | Agrilus vittaticolllis | Apple, Pear, Cranberry, Serviceberry, Hawthorn |
|  | Chrysobothris femorata | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
|  | Texania campestris | Basswood, Beech, Maple, Oak, Sycamore, Willow, Yellow-poplar |
| Cerambycidae | Goes pulverulentus | Beech, Elm, Nuttall, Willow, Black oak, Cherrybark oak, Water oak, Sycamore |
|  | Goes tigrinus | Oak |
|  | Neoclytus acuminatus | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
|  | Neoptychodes trilineatus | Fig, Alder, Mulberry, Willow, Netleaf hackberry |
|  | Oberea ocellata | Sumac, Apple, Peach, Plum, Pear, Currant, Blackberry |
|  | Oberea tripunctata | Dogwood, Viburnum, Elm, Sourwood, Blueberry, Rhododendron, Azalea, Laurel, Poplar, Willow, Mulberry |
|  | Oncideres cingulata | Hickory, Pecan, Persimmon, Elm, Sourwood, Basswood, Honeylocust, Dogwood, Eucalyptus, Oak, Hackberry, Maple, Fruit trees |
|  | Saperda calcarata | Poplar |
|  | Strophiona nitens | Chestnut, Oak, Hickory, Walnut, Beech, Maple |
| Scolytidae | Corthylus columbianus | Maple, Oak, Yellow-poplar, Beech, Boxelder, Sycamore, Birch, Basswood, Chestnut, Elm |
|  | Dendroctonus frontalis | Pine |
|  | Dryocoetes betulae | Birch, Sweetgum, Wild cherry, Beech, Pear |
|  | Monarthrum fasciatum | Oak, Maple, Birch, Chestnut, Sweetgum, Blackgum, Poplar, Hickory, Mimosa, Apple, Peach, Pine |
|  | Phloeotribus liminaris | Peach, Cherry, Plum, Black cherry, Elm, Mulberry, Mountain-ash |
|  | Pseudopityophthorus pruinosus | Oak, American beech, Black cherry, Chickasaw plum, Chestnut, Maple, Hickory, Hornbeam, Hophornbeam |

TABLE B-continued

Examples of native woodborers of economic importance.

| Family | Species | Host or Crop Infested |
| --- | --- | --- |
| Sesiidae | Paranthrene simulans | Oak, American chestnut |
| | Sannina uroceriformis | Persimmon |
| | Synanthedon exitiosa | Peach, Plum, Nectarine, Cherry, Apricot, Almond, Black cherry |
| | Synanthedon pictipes | Peach, Plum, Cherry, Beach, Black Cherry |
| | Synanthedon rubrofascia | Tupelo |
| | Synanthedon scitula | Dogwood, Pecan, Hickory, Oak, Chestnut, Beech, Birch, Black cherry, Elm, Mountain-ash, Viburnum, Willow, Apple, Loquat, Ninebark, Bayberry |
| | Vitacea polistiformis | Grape |

The present invention may be also used to control any insect pests that may be present in turfgrass, including for example beetles, caterpillars, fire ants, ground pearls, millipedes, sow bugs, mites, mole crickets, scales, mealybugs ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as Cyclocephala spp. (e.g. masked chafer, C. lurida), Rhizotrogus spp. (e.g. European chafer, R. majalis), Cotinus spp. (e.g. Green June beetle, C. nitida), Popillia spp. (e.g. Japanese beetle, P. japonica), Phyllophaga spp. (e.g. May/June beetle), Ataenius spp. (e.g. Black turfgrass Ataenius, A. spretulus), Maladera spp. (e.g. Asiatic garden beetle, M. castanea) and Tomarus spp.), ground pearls (Margarodes spp.), mole crickets (tawny, southern, and short-winged; Scapteriscus spp., Gryllotalpa africana) and leatherjackets (European crane fly, Tipula spp.).

The present invention may also be used to control insect pests of turfgrass that are thatch dwelling, including armyworms (such as fall armyworm Spodoptera frugiperda, and common armyworm Pseudaletia unipuncta), cutworms, billbugs (Sphenophorus spp., such as S. venatus verstitus and S. parvulus), and sod webworms (such as Crambus spp. and the tropical sod webworm, Herpetogramma phaeopteralis).

The present invention may also be used to control insect pests of turfgrass that live above the ground and feed on the turfgrass leaves, including chinch bugs (such as southern chinch bugs, Blissus insularis), Bermudagrass mite (Eriophyes cynodoniensis), rhodesgrass mealybug (Antonina graminis), two-lined spittlebug (Propsapia bicincta), leafhoppers, cutworms (Noctuidae family), and greenbugs. The present invention may also be used to control other pests of turfgrass such as red imported fire ants (Solenopsis invicta) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: Haematopinus spp., Linognathus spp., Pediculus spp. and Phtirus spp., Solenopotes spp.

Of the order Mallophagida: Trimenopon spp., Menopon spp., Trinoton spp., Bovicola spp., Werneckiella spp., Lepikentron spp., Damalina spp., Trichodectes spp. and Felicola spp.

Of the order Diptera and the suborders Nematocerina and Brachycerina, for example Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp.

Of the order Siphonapterida, for example Pulex spp., Ctenocephalides spp., Xenopsylla spp., Ceratophyllus spp.

Of the order Heteropterida, for example Cimex spp., Triatoma spp., Rhodnius spp., Panstrongylus spp.

Of the order Blattarida, for example Blatta orientalis, Periplaneta americana, Blattelagermanica and Supella spp.

Of the subclass Acaria (Acarida) and the orders Meta- and Meso-stigmata, for example Argas spp., Ornithodorus spp., Otobius spp., Ixodes spp., Amblyomma spp., Boophilus spp., Dermacentor spp., Haemophysalis spp., Hyalomma spp., Rhipicephalus spp., Dermanyssus spp., Raillietia spp., Pneumonyssus spp., Sternostoma spp. and Varroa spp.

Of the orders Actinedida (Prostigmata) and Acaridida (Astigmata), for example Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp. and Laminosioptes spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus spec., Tryptodendron spec., Apate monachus, Bostrychus capucins, Heterobostrychus brunneus, Sinoxylon spec. and Dinoderus minutus, and also hymenopterans such as Sirex juvencus, Urocerus gigas, Urocerus gigas taignus and Urocerus augur, and termites such as Kalotermes flavicollis, Cryptotermes brevis, Heterotermes

*indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharina*.

The compounds according to the invention can be used as pesticidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, microemulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, 10$^{th}$ Edition, Southern Illinois University, 2010.

The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):

Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%
Dusts:
active ingredient: 0.1 to 10%, preferably 0.1 to 5%
solid carrier: 99.9 to 90%, preferably 99.9 to 99%
Suspension Concentrates:
active ingredient: 5 to 75%, preferably 10 to 50%
water: 94 to 24%, preferably 88 to 30%
surface-active agent: 1 to 40%, preferably 2 to 30%
Wettable Powders:
active ingredient: 0.5 to 90%, preferably 1 to 80%
surface-active agent: 0.5 to 20%, preferably 1 to 15%
solid carrier: 5 to 95%, preferably 15 to 90%
Granules:
active ingredient: 0.1 to 30%, preferably 0.1 to 15%
solid carrier: 99.5 to 70%, preferably 97 to 85%

The following Examples further illustrate, but do not limit, the invention.

| Wettable powders | a) | b) | c) |
| --- | --- | --- | --- |
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
| --- | --- | --- | --- |
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The combination is thoroughly mixed with the adjuvants and the mixture is thoroughly ground in a suitable mill, affording powders that can be used directly for seed treatment.

| Emulsifiable concentrate | |
| --- | --- |
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
| --- | --- | --- | --- |
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder granules | |
| --- | --- |
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated granules | |
| --- | --- |
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

Suspension Concentrate

| Suspension concentrate | |
| --- | --- |
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Flowable Concentrate for Seed Treatment

| Flowable concentrate for seed treatment | |
| --- | --- |
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

Formulation types include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

PREPARATORY EXAMPLES

"Mp" means melting point in ° C. Free radicals represent methyl groups. $^1$H NMR measurements were recorded on a Brucker 400 MHz spectrometer, chemical shifts are given in ppm relevant to a TMS standard. Spectra measured in deuterated solvents as indicated. Either one of the LCMS methods below was used to characterize the compounds. The characteristic LCMS values obtained for each compound were the retention time ("Rt", recorded in minutes) and the measured molecular ion $(M+H)^+$.

LCMS and GCMS Methods:

Method 1:

Spectra were recorded on a Mass Spectrometer from Waters (ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 μm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: 0 min 0% B, 100% A; 1.2-1.5 min 100% B; Flow (ml/min) 0.85.

Method 2:

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 μm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH; gradient: 0 min 0% B, 100% A; 2.7-3.0 min 100% B; Flow (ml/min) 0.85.

Method 3:

Spectra were recorded on a Mass Spectrometer from Agilent Technologies (6410 Triple Quadruple Mass Spectrometer) equipped with an electrospray source (Polarity: Positive and Negative Polarity Switch, Capillary: 4.00 kV, Fragmentor: 100.00 V, Gas Temperature: 350° C., Gas Flow: 11 L/min, Nebulizer Gas: 45 psi, Mass range: 110-1000 Da, DAD Wavelength range: 210-400 nm). Column: KINETEX EVO C18, length 50 mm, diameter 4.6 mm, particle size 2.6 μm. Column oven temperature 40° C. Solvent gradient: A=Water with 0.1% formic acid: Acetonitrile (95:5 v/v). B=Acetonitrile with 0.1% formic acid. Gradient=0 min 90% A, 10% B; 0.9-1.8 min 0% A, 100% B, 2.2-2.5 min 90% A, 10% B. Flow rate 1.8 mL/min.

Method 4:

Spectra were recorded on a Mass Spectrometer from Waters (Acquity SDS Mass Spectrometer) equipped with an electrospray source (Polarity: Positive and Negative Polarity Switch, Capillary: 3.00 kV, Cone Voltage: 41.00 V, Source temperature: 150° C., Desolvation Gas Flow: 1000 L/Hr, Desolvation temperature: 500° C., Gas Flow @Cone: 50 L/hr, Mass range: 110-800 Da, PDA wavelength range: 210-400 nm. Column: Acquity UPLC HSS T3 C18, length 30 mm, diameter 2.1 mm, particle size 1.8 μm. Column oven temperature 40° C. Solvent gradient: A=Water with 0.1% formic acid: Acetonitrile (95:5 v/v). B=Acetonitrile with 0.05% formic acid. Gradient=0 min 90% A, 10% B; 0.2 min 50% A, 50% B; 0.7-1.3 min 0% A, 100% B; 1.4-1.6 min 90% A, 10% B. Flow rate 0.8 mL/min.

Method 5:

Spectra were recorded on a Mass Spectrometer from Waters (SQ detector 2 single quadrupole mass spectrometer) equipped with an electrospray source (Polarity: positive or negative ions, Capillary: 2.50 kV, Cone voltage: 41 V, Extractor: 3.00 V, Source Temperature: 150° C., Desolvation Temperature: 500° C., Cone Gas Flow: 50 L/Hr, Desolvation Gas Flow: 1000 L/Hr, Mass range: 100 to 600 Da) and an Acquity UPLC from Waters: Quaternary pump, heated column compartment and diode-array detector. Column used Waters UPLC HSS T3, 1.8 μm, 30×2.1 mm. Column oven temperature 40° C. DAD Wavelength range (nm): 200 to 350. Solvent Gradient: A=water+5% Acetonitrile+0.05% HCOOH, B=Acetonitrile+0.05% HCOOH. Gradient=0 min 90% A, 10% B; 0.2 min 50% A, 50% B; 0.7-1.3 min 0% A, 100% B; 1.4-1.6 min 90% A, 10% B. Flow rate 0.6 mL/min.

a) Preparation of Examples of Compounds of Formula (I)

Example P1: Preparation of [5-ethylsulfonyl-6-[7-(trifluoromethyl)imidazo[1,2-c]pyrimidin-2-yl]-3-pyridyl]imino-dimethyl-oxo-λ$^6$-sulfane (compound P1)

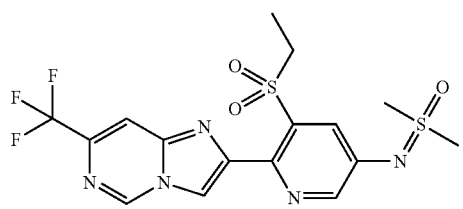

(P1)

To a solution of 2-(5-chloro-3-ethylsulfonyl-2-pyridyl)-7-(trifluoromethyl)imidazo[1,2-c]pyrimidine (WO16/071214) (0.4 g, 1.024 mmol) in toluene (8.2 mL) in a microwave vial under argon was added (S)-(−)-BINAP (0.1971 g, 0.3071 mmol), cesium carbonate (0.8338 g, 2.559 mmol), palladium(II) acetate (0.046 g, 0.2047 mmol) followed by imino-dimethyl-oxo-λ$^6$-sulfane (0.2479 g, 2.661 mmol). The vial was sealed and the mixture stirred in the microwave at 160° C. for 30 minutes. The reaction mixture was filtered over HYFLO and the filtrate evaporated under reduced pressure. The residue was purified by Combiflash over silicagel (0-5% methanol gradient in dichloromethane) and the fractions containing product were combined and concentrated. The residue was stirred in diethyl ether for 30 minutes, the suspension filtered and the solid dried in vacuo to afford [5-ethylsulfonyl-6-[7-(trifluoromethyl)imidazo[1,2-c] pyrimidin-2-yl]-3-pyridyl]imino-dimethyl-oxo-λ$^6$-sulfane (compound P1) as a solid (150 mg), mp 241-243° C. LCMS (method 1): 448 (M+H)$^+$, retention time 0.75 min.

Example P2: Preparation of [5-ethylsulfonyl-6-[3-methyl-6-(trifluoromethyl)imidazo[4,5-c]pyridin-2-yl]-3-pyridyl]imino-dimethyl-λ$^4$-sulfane (compound P17)

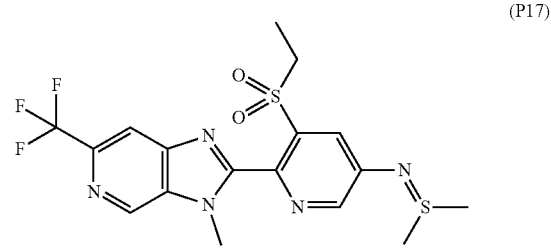 [SMILES: CCS(=O)(=O)c1cc(N=S(C)C)cnc1-c1nc2cc(C(F)(F)F)ncc2n1C]

(P17)

To a suspension of 5-ethylsulfonyl-6-[3-methyl-6-(trifluoromethyl)imidazo[4,5-c]pyridin-2-yl]pyridin-3-amine (WO16/091731) (200 mg, 0.52 mmol) and phosphorus pentoxide (147 mg, 1.04 mmol) in dry chloroform (5 ml) under argon was added a mixture of dimethylsulfoxide (142 mg, 0.13 ml, 1.82 mmol) and triethylamine (55 mg, 76 μl, 0.54 mmol) dropwise while keeping the internal temperature below 35-40° C. The mixture was stirred at room temperature overnight. The reaction mixture was carefully poured into an ice-cold aqueous NaOH solution (in excess to phosphorus pentoxide) while keeping the internal temperature below 10° C. The aqueous phase was extracted several times with chloroform, the combined organic layers washed with water and brine, dried over sodium sulfate, filtered and concentrated under reduced pressure. The residue was purified by Combiflash over silicagel (5% methanol in ethyl acetate) to afford [5-ethylsulfonyl-6-[3-methyl-6-(trifluoromethyl) imidazo[4,5-c]pyridin-2-yl]-3-pyridyl]imino-dimethyl-λ$^4$-sulfane (compound P17) as a solid (108 mg), mp 208-210° C. LCMS (method 1): 446 (M+H)$^+$, retention time 0.66 min.

TABLE P

Examples of compounds of formula (I)

| No. | IUPAC name | Structures | $R_t$ (min) | [M + H]$^+$ (measured) | Method | Mp (° C.) |
|---|---|---|---|---|---|---|
| P1 | [5-ethylsulfonyl-6-[7-(trifluoromethyl)imidazo[1,2-c]pyrimidin-2-yl]-3-pyridyl]imino-dimethyl-oxo-λ$^6$-sulfane | 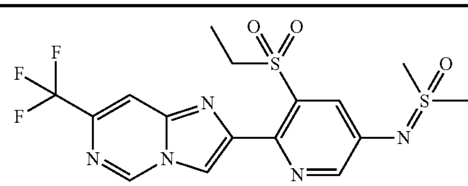 | 0.75 | 448 | 1 | 241-243 |

TABLE P-continued

Examples of compounds of formula (I)

| No. | IUPAC name | Structures | LCMS R$_t$ (min) | [M + H]$^+$ (measured) | Method | Mp (° C.) |
|---|---|---|---|---|---|---|
| P2 | [5-ethylsulfonyl-6-[3-methyl-6-(trifluoromethyl)imidazo[4,5-c]pyridin-2-yl]-3-pyridyl]imino-dimethyl-oxo-λ$^6$-sulfane | 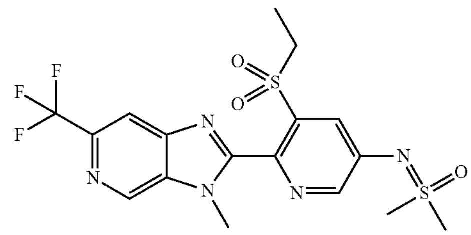 [SMILES: CCS(=O)(=O)c1cc(N=S(C)(C)=O)cnc1-c1nc2cc(C(F)(F)F)ncc2n1C] | 0.80 | 462 | 1 | 190-192 |
| P3 | cyclopropyl-[[5-ethylsulfonyl-6-[3-methyl-6-(trifluoromethyl)imidazo[4,5-c]pyridin-2-yl]-3-pyridyl]imino]-methyl-oxo-λ$^6$-sulfane | 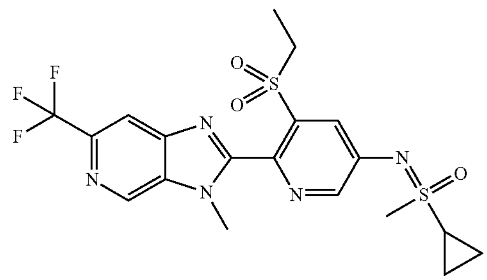 [SMILES: CCS(=O)(=O)c1cc(N=S(C)(=O)C2CC2)cnc1-c1nc2cc(C(F)(F)F)ncc2n1C] | 0.88 | 488 | 1 | 166-168 |
| P4 | diethyl-[[5-ethylsulfonyl-6-[3-methyl-6-(trifluoromethyl)imidazo[4,5-c]pyridin-2-yl]-3-pyridyl]imino]-oxo-λ$^6$-sulfane | 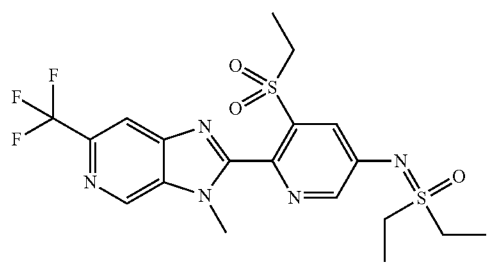 [SMILES: CCS(=O)(=O)c1cc(N=S(=O)(CC)CC)cnc1-c1nc2cc(C(F)(F)F)ncc2n1C] | 0.90 | 490 | 1 | 168-170 |
| P5 | 4-[[5-ethylsulfonyl-6-[3-methyl-6-(trifluoromethyl)imidazo[4,5-c]pyridin-2-yl]-3-pyridyl]imino]-1,4-oxathiane 4-oxide | 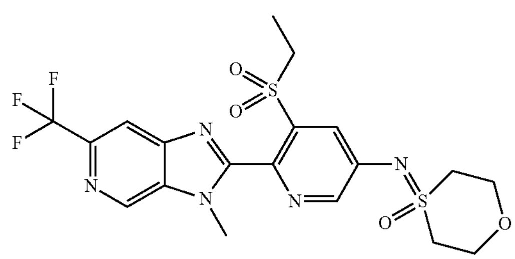 [SMILES: CCS(=O)(=O)c1cc(N=S2(=O)CCOCC2)cnc1-c1nc2cc(C(F)(F)F)ncc2n1C] | 0.85 | 504 | 1 | 198-200 |
| P6 | 1-[[5-ethylsulfonyl-6-[3-methyl-6-(trifluoromethyl)imidazo[4,5-c]pyridin-2-yl]-3-pyridyl]imino]thiolane 1-oxide | 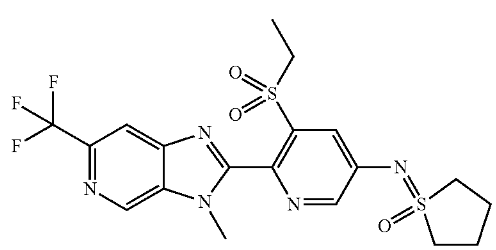 [SMILES: CCS(=O)(=O)c1cc(N=S2(=O)CCCC2)cnc1-c1nc2cc(C(F)(F)F)ncc2n1C] | 0.87 | 488 | 1 | 192-194 |
| P7 | cyclopropyl-[[5-ethylsulfonyl-6-[7-methyl-3-(trifluoromethyl)imidazo[4,5-c]pyridazin-6-yl]-3-pyridyl]imino]-methyl-oxo-λ$^6$-sulfane | 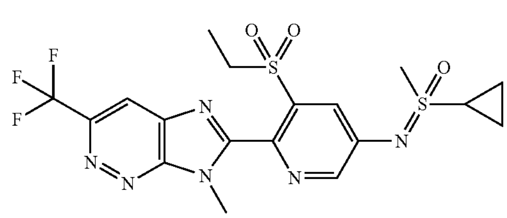 [SMILES: CCS(=O)(=O)c1cc(N=S(C)(=O)C2CC2)cnc1-c1nc2cc(C(F)(F)F)nnc2n1C] | 0.86 | 489 | 1 | |

TABLE P-continued

Examples of compounds of formula (I)

| No. | IUPAC name | Structures | LCMS R$_t$ (min) | [M + H]$^+$ (measured) | Method | Mp (° C.) |
|---|---|---|---|---|---|---|
| P8 | cyclopropyl-[[5-ethylsulfonyl-6-[7-(trifluoromethyl)imidazo[1,2-c]pyrimidin-2-yl]-3-pyridyl]imino]-methyl-oxo-λ$^6$-sulfane | | 0.82 | 474 | 1 | |
| P9 | [5-ethylsulfonyl-6-[7-methyl-3-(trifluoromethyl)imidazo[4,5-c]pyridazin-6-yl]-3-pyridyl]imidno-dimethyl-oxo-λ$^6$-sulfane | | 0.80 | 463 | 1 | |
| P10 | [5-ethylsulfonyl-6-[7-(trifluoromethyl)imidazo[1,2-c]pyrimidin-2-yl]-3-pyridyl]imino-methyl-oxo-(p-tolyl)-λ$^6$-sulfane | | 0.94 | 524 | 1 | 155-157 |
| P11 | 1-[[5-ethylsulfonyl-6-[3-methyl-6-(trifluoromethyl)imidazo[4,5-c]pyridin-2-yl]-3-pyridyl]imino]thietane 1-oxide | | 0.84 | 474 | 1 | |
| P12 | cyclopropyl-[[5-ethylsulfonyl-6-[6-(trifluoromethyl)pyrazolo[4,3-c]pyridin-2-yl]-3-pyridyl]imino]-methyl-oxo-λ$^6$-sulfane | | 0.91 | 474 | 4 | 203-205 |
| P13 | 1-[[5-ethylsulfonyl-6-[7-(trifluoromethyl)imidazo[1,2-c]pyrimidin-2-yl]-3-pyridyl]imino]thietane 1-oxide | | 0.82 | 460 | 1 | 226-228 |

TABLE P-continued

Examples of compounds of formula (I)

| No. | IUPAC name | Structures | LCMS R$_t$ (min) | [M + H]$^+$ (measured) | Method | Mp (° C.) |
|---|---|---|---|---|---|---|
| P14 | [3-ethylsulfonyl-4-[7-(trifluoromethyl)imidazo[1,2-c]pyrimidin-2-yl]phenyl]imino-dimethyl-oxo-λ$^6$-sulfane | 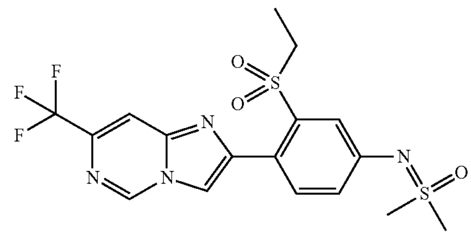 [SMILES: CCS(=O)(=O)c1cc(N=S(C)(C)=O)ccc1-c1cn2cnc(C(F)(F)F)cc2n1] | 0.80 | 447 | 1 | 177-179 |
| P15 | cyclopropyl-[3-ethylsulfonyl-4-[7-(trifluoromethyl)imidazo[1,2-c]pyrimidin-2-yl]phenyl]imino-methyl-oxo-λ$^6$-sulfane | 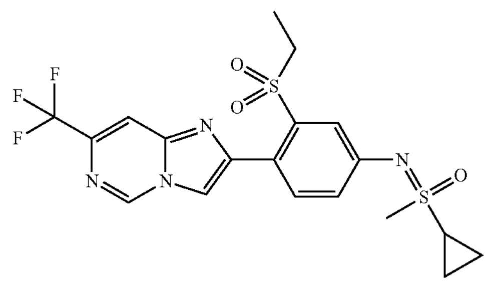 [SMILES: CCS(=O)(=O)c1cc(N=S(C)(=O)C2CC2)ccc1-c1cn2cnc(C(F)(F)F)cc2n1] | 0.87 | 473 | 1 | |
| P16 | [5-ethylsulfonyl-6-[6-(trifluoromethyl)pyrazolo[4,3-c]pyridin-2-yl]-3-pyridyl]imino-dimethyl-oxo-λ$^6$-sulfane | 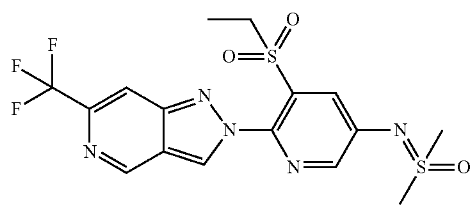 [SMILES: CCS(=O)(=O)c1cc(N=S(C)(C)=O)cnc1-n1cc2cnc(C(F)(F)F)cc2n1] | 0.88 | 448 | 4 | 258-260 |
| P17 | [5-ethylsulfonyl-6-[3-methyl-6-(trifluoromethyl)imidazo[4,5-c]pyridin-2-yl]-3-pyridyl]imino-dimethyl-λ$^4$-sulfane | 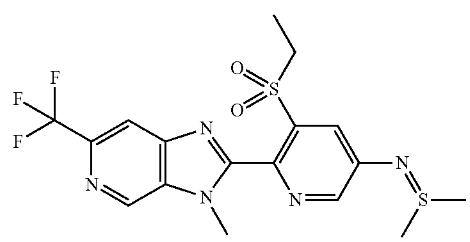 [SMILES: CCS(=O)(=O)c1cc(N=S(C)C)cnc1-c1nc2cc(C(F)(F)F)ncc2n1C] | 0.66 | 446 | 1 | 208-210 |
| P18 | diethyl-[[5-ethylsulfonyl-6-[3-methyl-6-(trifluoromethyl)imidazo[4,5-c]pyridin-2-yl]-3-pyridyl]imino-λ$^4$-sulfane | 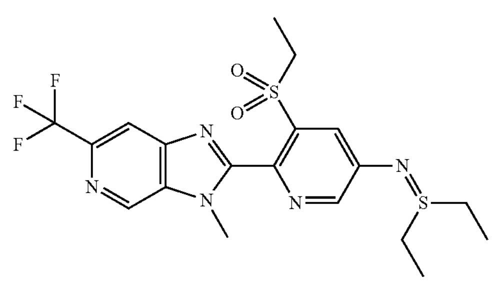 [SMILES: CCS(CC)=Nc1cnc(-c2nc3cc(C(F)(F)F)ncc3n2C)c(S(=O)(=O)CC)c1] | 0.71 | 474 | 1 | 173-173 |
| P19 | ethyl-[[5-ethylsulfonyl-6-[3-methyl-6-(trifluoromethyl)imidazo[4,5-c]pyridin-2-yl]-3-pyridyl]imino]-methyl-oxo-λ$^6$-sulfane | 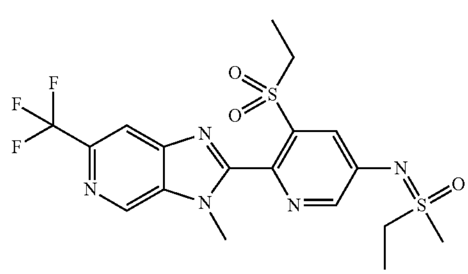 [SMILES: CCS(=O)(=O)c1cc(N=S(C)(=O)CC)cnc1-c1nc2cc(C(F)(F)F)ncc2n1C] | 0.85 | 476 | 1 | 164-164 |

TABLE P-continued

Examples of compounds of formula (I)

| No. | IUPAC name | Structures | LCMS R_f (min) | [M + H]+ (measured) | Method | Mp (° C.) |
|---|---|---|---|---|---|---|
| P20 | [5-ethylsulfanyl-6-[3-methyl-6-(trifluoromethyl)imidazo[4,5-c]pyridin-2-yl]-3-pyridyl]imino-dimethyl-oxo-$\lambda^6$-sulfane | | 0.85 | 430 | 1 | 196-198 |
| P21 | 4-[3-ethylsulfonyl-4-[3-methyl-6-(trifluoromethyl)imidazo[4,5-c]pyridin-2-yl]phenyl]imino-1,4-oxathiane 4-oxide | | 0.84 | 503 | 1 | 237-238 |
| P22 | 4-[[5-ethylsulfonyl-6-[7-(trifluoromethyl)imidazo[1,2-c]pyrimidin-2-yl]-3-pyridyl]imino]-1,4-oxathiane 4-oxide | | 0.81 | 490 | 1 | 232-235 |
| P23 | 4-[[5-ethylsulfonyl-6-[7-methyl-3-(trifluoromethyl)imidao[4,5-c]pyridazin-6-yl]-3-pyridyl]imino]-1,4-oxathiane 4-oxide | | 0.85 | 505 | 1 | |
| P24 | 4-[3-ethylsulfanyl-4-[7-methyl-3-(trifluoromethyl)imidazo[4,5-c]pyridazin-6-yl]phenyl]imino-1,4-oxathiane 4-oxide | | 0.91 | 472 | 1 | |

TABLE P-continued

Examples of compounds of formula (I)

| No. | IUPAC name | Structures | LCMS R_t (min) | [M + H]+ (measured) | Method | Mp (° C.) |
|---|---|---|---|---|---|---|
| P25 | 4-[3-ethylsulfonyl-4-[7-methyl-3-(trifluoromethyl)imidazo[4,5-c]pyridazin-6-yl]phenyl]imino-1,4-oxathiane 4-oxide | | 0.82 | 504 | 1 | 253-255 |
| P26 | 2-[3-ethylsulfonyl-5-(1,4-oxathian-4-ylideneamino)-2-pyridyl]-3-methyl-6-(trifluoromethyl)imidazo[4,5-c]pyridine | | 0.98 | 488 | 2 | 214 (dec) | b) Preparation of Intermediates of Formula 16, 17, 10, 11, 12 and (XI-A, wherein Rf is CF$_3$)

Example P-I1: (Z)-6,6,6-trifluoro-5-hydroxy-1,1-dimethoxy-hex-4-en-3-one (compound 16-A)

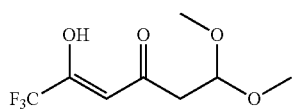

(16-A)

To a stirred mixture of 4,4-dimethoxybutan-2-one (47.39 g) and ethyl trifluoroacetate (76.54 g) was added a sodium methoxide solution in methanol (25 mass %, 123 mL) dropwise at room temperature and stirring was continued at the same temperature for 6 hours. The reaction mixture was then cooled to 10° C. and an aqueous 20% H$_3$PO$_4$ solution (150 mL) was added dropwise till pH ~4. The reaction mixture was partitioned between water and ethyl acetate and the organic layer was separated. The aqueous phase was re-extracted twice with ethyl acetate. The combined organic layers were dried over sodium sulfate and concentrated under reduced pressure to afford (Z)-6,6,6-trifluoro-5-hydroxy-1,1-dimethoxy-hex-4-en-3-one (16-A) as brown oil (64.05 g). LCMS (method 5): 227.26 (M–H+), retention time 0.53 min.

$^1$H NMR (400 MHz, CDCl$_3$) δ ppm 5.98 (s, 1H), 4.79 (t, J=5.7 Hz, 1H), 3.39-3.35 (m, 7H), 2.76 (d, J=5.6 Hz, 2H).

Example P-I2: (Z)-4-amino-1,1,1-trifluoro-6,6-dimethoxy-hex-3-en-2-one (compound 17-A)

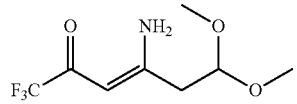

(17-A)

A stirred solution of (Z)-6,6,6-trifluoro-5-hydroxy-1,1-dimethoxy-hex-4-en-3-one (16-A) (8.50 g) in dioxane was purged using gaseous NH$_3$ for 1 hour. The vessel was sealed and heated at 40° C. for 8 hours. The reaction mixture was then cooled to room temperature and concentrated under reduced pressure. The residue was purified by flash chromatography to afford (Z)-4-amino-1,1,1-trifluoro-6,6-dimethoxy-hex-3-en-2-one (17-A) as a brown oil (5.92 g). LCMS (method 5): 226.28 (M+H+), retention time 0.88 min.

$^1$H NMR (400 MHz, DMSO-d$_6$) δ ppm 2.60 (d, J=5.8 Hz, 2H), 3.26 (s, 6H), 4.66 (t, J=5.8 Hz, 1H), 5.35 (s, 1H), 8.93 (br s, 1H), 9.88 (br s, 1H).

Example P-I3: 2-(trifluoromethyl)pyridin-4-amine (compound 10-A)

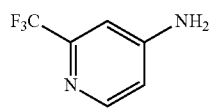

(10-A)

Method-A: From Compound (17-A)

To a stirred solution of (Z)-4-amino-1,1,1-trifluoro-6,6-dimethoxy-hex-3-en-2-one (17-A) (4.34 g) in acetonitrile was added NH$_4$OAc (7.35 g) followed by the addition of acetic acid (3.1 mL). The vessel was sealed and heated at 150° C. for 8 hours. The reaction mixture was then cooled to room temperature, diluted with water and extracted twice with CH$_2$Cl$_2$. The combined organic layers were washed with brine, dried over sodium sulfate and concentrated under reduced pressure. The crude was purified by flash chromatography to afford 2-(trifluoromethyl)pyridin-4-amine (10-A) as a yellowish oil (1.86 g). LCMS (method 5): 163.24 (M+H$^+$), retention time 0.19 min.

$^1$H NMR (400 MHz, DMSO-d$_6$) δ 6.56 (br. s., 2H) 6.65 (dd, J=5.6, 1.96 Hz, 1H) 6.89 (d, J=2.1 Hz, 1H) 8.09 (d, J=5.6 Hz, 1H).

Method-B: Via Smiles Rearrangement

To a stirred solution of 2-(trifluoromethyl)pyridin-4-ol (4.7 g) in N,N-dimethylacetamide (50 mL) was added potassium carbonate (9.96 g) followed by the addition of 2-chloro-acetamide (3.23 g) at room temperature. The reaction mixture was heated to 90° C. and continued stirring at the same temperature for 3 hours. The reaction temperature was further increased to 150° C. and allowed to stir at the same temperature for 3 hours. The reaction mixture was partitioned between water and t-butylmethylether TBME. The organic layer was separated and the aqueous layer was re-extracted twice with TBME. The combined organic layers were washed with brine, dried over sodium sulfate and concentrated under reduced pressure to afford 2-(trifluoromethyl)pyridin-4-amine (10-A) as a yellowish oil (3.97 g). The sample generated with Method-B showed the same analytical data as the one produced with Method-A.

Method-C: From Compound (12-A)

To a stirred suspension of 4-chloro-2-(trifluoromethyl)pyridine (12-A) (0.180 g) in DMSO (2 mL) was added CuI (0.038 g) followed by the addition of L-proline (0.0461 g), potassium carbonate (0.208 g) and ammonium hydroxide (25%, 1.39 g) The reaction vessel was sealed and heated at 100° C. for 5 hours. The reaction mixture was partitioned between TBME and a saturated aqueous solution of NaHCO$_3$. The organic layer was separated and the aqueous layer was re-extracted with TBME. The combined organic layers were washed with brine, dried over sodium sulfate and concentrated under reduced pressure. The residue was purified by flash chromatography to afford 2-(trifluoromethyl)pyridin-4-amine (10-A) as a yellowish oil.

The sample generated with Method-C showed the same analytical data as the one produced with Method-A.

Method-D: From Compound (16-A)

A stirred solution of (Z)-6,6,6-trifluoro-5-hydroxy-1,1-dimethoxy-hex-4-en-3-one (16-A) (0.90 g) in propionitrile was saturated using gaseous NH$_3$ for 1 hour. The reaction vessel was sealed and heated at 50° C. for 6 hours. The reaction mixture was then cooled to room temperature and NH$_4$OAc (0.94 g) followed by acetic acid (0.71 g) were added. The vessel was sealed and heated at 150° C. for 8 hours. The reaction vessel was closed and heated at 150° C. for 6 h. The reaction mixture was then cooled to room temperature, diluted with water and extracted twice with CH$_2$Cl$_2$. The combined organic layers were washed with brine, dried over sodium sulfate and concentrated under reduced pressure. The crude was purified by flash chromatography to afford 2-(trifluoromethyl)pyridin-4-amine (10-A) as a yellowish oil (0.315 g).

The sample generated with Method-D showed the same analytical data as the one produced with Method-A.

Example P-I4: 5-bromo-2-(trifluoromethyl)pyridin-4-amine (compound 11-A)

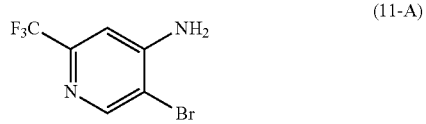

(11-A)

To a stirred solution of 2-(trifluoromethyl)pyridin-4-amine (10-A) (4.84 g) in acetic acid (50 mL) was added ammonium bromide (3.77 g) and the mixture was heated to 70° C. To the reaction mixture was added hydrogen peroxide (30% in water, 4.58 mL) dropwise over a period of 1 hour at 70° C. and heating was continued at the same temperature for 1 hour. The reaction mixture was cooled down to room temperature and carefully poured on a 10% sodium bisulfite aqueous solution (150 mL). A solid precipitated, which was filtered off and dried to afford 5-bromo-2-(trifluoromethyl)pyridin-4-amine (11-A) as a white solid (5.59 g). LCMS (method 5): 241.06 (M+H$^+$), retention time 0.77 min.

$^1$H NMR (400 MHz, CDCl$_3$) δ ppm 6.96 (s, 1H) 8.43-8.51 (m, 1H).

Example P-I5: N3-methyl-6-(trifluoromethyl)pyridine-3,4-diamine (compound XI-A, wherein Rf is CF$_3$)

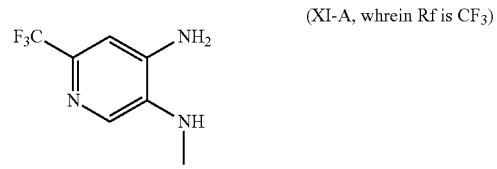

(XI-A, whrein Rf is CF$_3$)

To a stirred suspension of 5-bromo-2-(trifluoromethyl)pyridin-4-amine (11-A) (1.89 g) and methyl amine MeNH$_2$ (40% in water, 10.2 mL) in water was added CuI (0.076 g) followed by the addition of 1-(2-pyridyl)ethanone oxime (0.0678 g). The reaction vessel was sealed and heated at 85° C. for 6 hours. The reaction mixture was partitioned between TBME and a saturated aqueous solution of NaHCO$_3$. The organic layer was separated and the aqueous layer was re-extracted with TBME. Combined organic layers were washed with brine, dried over sodium sulfate and concentrated under reduced pressure. The residue was purified by flash chromatography to afford N3-methyl-6-(trifluoromethyl)pyridine-3,4-diamine (XI-A, wherein Rf is CF$_3$) as a white solid (1.10 g), mp 138-140° C. LCMS (method 5): 192.33 (M+H$^+$), retention time 0.15 min.

$^1$H NMR (400 MHz, DMSO-d$_6$) δ ppm 2.80 (d, J=4.9 Hz, 3H) 5.22 (br d, J=5.0 Hz, 1H) 5.82 (s, 2H) 6.84 (s, 1H) 7.58 (s, 1H).

Example P-I6: 4-chloro-2-(trifluoromethyl)pyridine (compound 12-A)

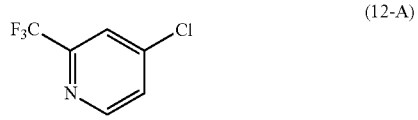 [SMILES: FC(F)(F)c1cc(Cl)ccn1]

To a stirred solution of 2-(trifluoromethyl)pyridin-4-ol (9.4 g) in 50 mL cyclohexane and a drop of DMF, oxalyl dichloride (2.6 equiv.) was added dropwise over a period of 5 minutes at 25° C. After addition, the reaction mixture was heated to 80° C. for 3 hours. The reaction mixture was cooled to room temperature and 50 mL of water were added dropwise. The aqueous phase was extracted with 3×100 mL TBME. The combined TBME layers were washed with 70 ml of a saturated aqueous solution of sodium bicarbonate. The organic layers were dried over sodium sulfate and concentrated under reduced pressure to obtain 4-chloro-2-(trifluoromethyl)pyridine (12-A) as a yellow liquid (7.31 g). LCMS (method 5): 192 (M+H⁺), retention time 0.96 min.

$^1$H NMR (400 MHz, CDCl$_3$) δ ppm 7.51 (dd, J=5.2, 1.5 Hz, 1H) 7.71 (d, J=1.6 Hz, 1H) 8.64 (d, J=5.3 Hz, 1H).

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use. Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds described in Tables 1 to 9 and Table P of the present invention"):

an adjuvant selected from the group of substances consisting of petroleum oils (alternative name) (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromo-cyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin 1 (696)+TX, pyrethrin 11 (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+

TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquinbutyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin 11 (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxy-aminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin 11 (696)+TX, jodfenphos (1248)+TX, juvenile hormone I (alternative name) [CCN]+TX, juvenile hormone II (alternative name) [CCN]+TX, juvenile hormone lll (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemetonmethyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin 1 (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, fluxametamide (WO 2007/026965)+TX, epsilon-metofluthrin [240494-71-7]+TX, epsilon-momfluorothrin [1065124-65-3]+TX, fluazaindolizine [1254304-22-7]+TX, chloroprallethrin [399572-87-3]+TX, fluxametamide [928783-29-3]+TX, cyhalodiamide [1262605-53-7]+TX, tioxazafen [330459-31-9]+TX, broflanilide [1207727-04-5]+TX, flufiprole [704886-18-0]+TX, cyclaniliprole [1031756-98-5]+TX, tetraniliprole [1229654-66-3]+TX, guadipyr (described in WO2010/060231)+TX, cycloxaprid (described in WO2005/077934)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-

4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, meta-laxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzo-lar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-LI90 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphtalen-5-yl)-amide (dislosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a,12b-decahydro-6,12-dihyd roxy-4,6a, 12b-trimethyl-1-oxo-9-(3-pyridinyl)-2H, 11 Hnaphtho[2,1-b]pyrano[3,4-e]pyran-4-yl] methyl-cyclopropanecarboxylate [915972-17-7]+TX, 1,3,5-trimethyl-N-(2-methyl-1-oxopropyl)-N-[3-(2-methylpropyl)-4-[2,2,2-trifluoro-1-methoxy-1-(trifluoromethyl)ethyl] phenyl]-1H-pyrazole-4-carboxamide [926914-55-8]+TX; lancotrione [1486617-21-3], florpyrauxifen [943832-81-3], ipfentrifluconazole[1417782-08-1], mefentrifluconazole [1417782-03-6], quinofumelin [861647-84-9], chloropralle-thrin [399572-87-3], cyhalodiamide [1262605-53-7], fluazaindolizine [1254304-22-7], fluxametamide [928783-29-3], epsilon-metofluthrin [240494-71-7], epsilon-momfluorothrin [1065124-65-3], pydiflumetofen [1228284-64-7], kappa-bifenthrin [439680-76-9], broflanilide [1207727-04-5], dicloromezotiaz [1263629-39-5], dipymetitrone [16114-35-5], pyraziflumid [942515-63-1], kappa-tefluthrin [391634-71-2], fenpicoxamid [517875-34-2], fluindapyr [1383809-87-7], alpha-bromadiolone [28772-56-7], flupyrimin [1689566-03-7], benzpyrimoxan [1449021-97-9], acynonapyr [1332838-17-1], inpyrfluxam [1352994-67-2], isoflucypram [1255734-28-1], tyclopyrazoflor [1477919-27-9], spiropidion [1229023-00-0] and pyrapropoyne [1803108-03-3]; and microbials including: *Acinetobacter lwoffii*+TX, *Acremonium alternatum*+TX+TX, *Acremonium cephalosporium*+TX+TX, *Acremonium diospyri*+TX, *Acremonium obclavatum*+TX, *Adoxophyes orana granulovirus* (AdoxGV) (Capex®)+TX, *Agrobacterium radiobacter* strain K84 (Galltrol-A®)+TX, *Alternaria alternate*+TX, *Alternaria cassia*+TX, *Alternaria destruens* (Smolder®)+TX, *Ampelomyces quisqualis* (AQ10®)+TX, *Aspergillus flavus* AF36 (AF36®)+TX, *Aspergillus flavus* NRRL 21882 (Aflaguard®)+TX, *Aspergillus* spp.+TX, *Aureobasidium pullulans*+TX, *Azospirillum*+TX, (MicroAZ®+TX, TAZO B®)+TX, *Azotobacter*+TX, *Azotobacter chroococcum* (Azotomeal®)+TX, *Azotobacter* cysts (Bionatural Blooming Blossoms®)+TX, *Bacillus amyloliquefaciens*+TX, *Bacillus cereus*+TX, *Bacillus chitinosporus* strain CM-1+TX, *Bacillus chitinosporus* strain AQ746+TX, *Bacillus licheniformis* strain HB-2 (Biostart™ Rhizoboost®)+TX, *Bacillus licheniformis* strain 3086 (EcoGuard®+TX, Green Releaf®)+TX, *Bacillus circulans*+TX, *Bacillus firmus* (BioSafe®+TX, BioNem-WP®+TX, VOTiVO®)+TX, *Bacillus firmus* strain 1-1582+TX, *Bacillus macerans*+TX, *Bacillus marismortui*+TX, *Bacillus megaterium*+TX, *Bacillus mycoides* strain AQ726+TX, *Bacillus papillae* (Milky Spore Powder®)+TX, *Bacillus pumilus* spp.+TX, *Bacillus pumilus* strain GB34 (Yield Shield®)+TX, *Bacillus pumilus* strain AQ717+TX, *Bacillus pumilus* strain QST 2808 (Sonata®+TX, Ballad Plus®)+TX, *Bacillus sphaericus* (VectoLex®)+TX, *Bacillus* spp.+TX, *Bacillus* spp. strain AQ175+TX, *Bacillus* spp. strain AQ177+TX, *Bacillus* spp. strain AQ178+TX, *Bacillus subtilis* strain QST 713 (CEASE®+

TX, Serenade®+TX, Rhapsody®)+TX, *Bacillus subtilis* strain QST 714 (JAZZ®)+TX, *Bacillus subtilis* strain AQ153+TX, *Bacillus subtilis* strain AQ743+TX, *Bacillus subtilis* strain QST3002+TX, *Bacillus subtilis* strain QST3004+TX, *Bacillus subtilis* var. *amyloliquefaciens* strain FZB24 (Taegro®+TX, Rhizopro®)+TX, *Bacillus thuringiensis* Cry 2Ae+TX, *Bacillus thuringiensis* Cry1Ab+TX, *Bacillus thuringiensis aizawai* GC 91 (Agree®)+TX, *Bacillus thuringiensis israelensis* (BMP123®+TX, Aquabac®+TX, VectoBac®)+TX, *Bacillus thuringiensis kurstaki* (Javelin®+TX, Deliver®+TX, CryMax®+TX, Bonide®+TX, Scutella WP®+TX, Turilav WP®+TX, Astuto®+TX, Dipel WP®+TX, Biobit®+TX, Foray®)+TX, *Bacillus thuringiensis kurstaki* BMP 123 (Baritone®)+TX, *Bacillus thuringiensis kurstaki* HD-1 (Bioprotec-CAF/3P®)+TX, *Bacillus thuringiensis* strain BD#32+TX, *Bacillus thuringiensis* strain AQ52+TX, *Bacillus thuringiensis* var. *aizawai* (XenTari®+TX, DiPel®)+TX, bacteria spp. (GROWMEND®+TX, GROWSWEET®+TX, Shootup®)+TX, bacteriophage of *Clavipacter michiganensis* (AgriPhage®)+TX, Bakflor®+TX, *Beauveria bassiana* (Beaugenic®+TX, Brocaril WP®)+TX, *Beauveria bassiana* GHA (Mycotrol ES®+TX, Mycotrol O®+TX, BotaniGuard®)+TX, *Beauveria brongniartii* (Engerlingspilz®+TX, *Schweizer Beauveria*®+TX, Melocont®)+TX, *Beauveria* spp.+TX, *Botrytis cineria*+TX, *Bradyrhizobium japonicum* (TerraMax®)+TX, *Brevibacillus brevis*+TX, *Bacillus thuringiensis tenebrionis* (Novodor®)+TX, BtBooster+TX, *Burkholderia cepacia* (Deny®+TX, Intercept®+TX, Blue Circle®)+TX, *Burkholderia gladii*+TX, *Burkholderia gladioli*+TX, *Burkholderia* spp.+TX, Canadian thistle fungus (CBH Canadian Bioherbicide®)+TX, *Candida butyri*+TX, *Candida famata*+TX, *Candida fructus*+TX, *Candida glabrata*+TX, *Candida guilliermondii*+TX, *Candida melibiosica*+TX, *Candida oleophila* strain O+TX, *Candida parapsilosis*+TX, *Candida pelliculosa*+TX, *Candida pulcherrima*+TX, *Candida reukaufii*+TX, *Candida saitoana* (Bio-Coat®+TX, Biocure®)+TX, *Candida sake*+TX, *Candida* spp.+TX, *Candida tenius*+TX, *Cedecea dravisae*+TX, *Cellulomonas flavigena*+TX, *Chaetomium cochliodes* (Nova-Cide®)+TX, *Chaetomium globosum* (Nova-Cide®)+TX, *Chromobacterium subtsugae* strain PRAA4-1T (Grandevo®)+TX, *Cladosporium cladosporioides*+TX, *Cladosporium oxysporum*+TX, *Cladosporium chlorocephalum*+TX, *Cladosporium* spp.+TX, *Cladosporium tenuissimum*+TX, *Clonostachys rosea* (EndoFine®)+TX, *Colletotrichum acutatum*+TX, *Coniothyrium minitans* (Cotans WG®)+TX, *Coniothyrium* spp.+TX, *Cryptococcus albidus* (YIELDPLUS®)+TX, *Cryptococcus humicola*+TX, *Cryptococcus infirmo-miniatus*+TX, *Cryptococcus laurentii*+TX, *Cryptophlebia leucotreta granulovirus* (Cryptex®)+TX, *Cupriavidus campinensis*+TX, *Cydia pomonella granulovirus* (CYD-X®)+TX, *Cydia pomonella granulovirus* (Madex®+TX, Madex Plus®+TX, Madex Max/Carpovirusine®)+TX, *Cylindrobasidium laeve* (Stumpout®)+TX, *Cylindrocladium*+TX, *Debaryomyces hansenii*+TX, *Drechslera hawaiinensis*+TX, *Enterobacter cloacae*+TX, Enterobacteriaceae+TX, *Entomophtora virulenta* (Vektor@)+TX, *Epicoccum nigrum*+TX, *Epicoccum purpurascens*+TX, *Epicoccum* spp.+TX, *Filobasidium floriforme*+TX, *Fusarium acuminatum*+TX, *Fusarium chlamydosporum*+TX, *Fusarium oxysporum* (Fusaclean®/Biofox C®)+TX, *Fusarium proliferatum*+TX, *Fusarium* spp.+TX, *Galactomyces geotrichum*+TX, *Gliocladium catenulatum* (Primastop®+TX, Prestop®)+TX, *Gliocladium roseum*+TX, *Gliocladium* spp. (SoilGard®)+TX, *Gliocladium virens* (Soilgard®)+TX, *Granulovirus* (Granupom®)+TX, *Halobacillus halophilus*+TX, *Halobacillus litoralis*+TX, *Halobacillus trueperi*+TX, *Halomonas* spp.+TX, *Halomonas subglaciescola*+TX, *Halovibrio variabilis*+TX, *Hanseniaspora uvarum*+TX, *Helicoverpa armigera* nucleopolyhedrovirus (Helicovex®)+TX, *Helicoverpa zea* nuclear polyhedrosis virus (Gemstar®)+TX, Isoflavone—formononetin (Myconate®)+TX, *Kloeckera apiculata*+TX, *Kloeckera* spp.+TX, *Lagenidium giganteum* (Laginex®)+TX, *Lecanicillium longisporum* (Vertiblast®)+TX, *Lecanicillium muscarium* (Vertikil®)+TX, *Lymantria Dispar* nucleopolyhedrosis virus (Disparvirus®)+TX, *Marinococcus halophilus*+TX, *Meira geulakonigii*+TX, *Metarhizium anisopliae* (Met52®)+TX, *Metarhizium anisopliae* (Destruxin WP®)+TX, *Metschnikowia fruticola* (Shemer®)+TX, *Metschnikowia pulcherrima*+TX, *Microdochium dimerum* (Antibot®)+TX, *Micromonospora coerulea*+TX, *Microsphaeropsis ochracea*+TX, *Muscodor albus* 620 (Muscudor®)+TX, *Muscodor roseus* strain A3-5+TX, *Mycorrhizae* spp. (AMykor®+TX, Root Maximizer®)+TX, *Myrothecium verrucaria* strain AARC-0255 (DiTera®)+TX, BROS PLUS®+TX, *Ophiostoma piliferum* strain D97 (Sylvanex®)+TX, *Paecilomyces farinosus*+TX, *Paecilomyces fumosoroseus* (PFR-97®+TX, PreFeRal®)+TX, *Paecilomyces linacinus* (Biostat WP®)+TX, *Paecilomyces lilacinus* strain 251 (MeloCon WG®)+TX, *Paenibacillus polymyxa*+TX, *Pantoea agglomerans* (BlightBan C9-1®)+TX, *Pantoea* spp.+TX, *Pasteuria* spp. (Econem®)+TX, *Pasteuria nishizawae*+TX, *Penicillium aurantiogriseum*+TX, *Penicillium billai* (Jumpstart®+TX, TagTeam®)+TX, *Penicillium brevicompactum*+TX, *Penicillium frequentans*+TX, *Penicillium griseofulvum*+TX, *Penicillium purpurogenum*+TX, *Penicillium* spp.+TX, *Penicillium viridicatum*+TX, *Phlebiopsis gigantean* (Rotstop®)+TX, phosphate solubilizing bacteria (Phosphomeal®)+TX, *Phytophthora cryptogea*+TX, *Phytophthora palmivora* (Devine®)+TX, *Pichia anomala*+TX, *Pichia guilermondii*+TX, *Pichia membranaefaciens*+TX, *Pichia onychis*+TX, *Pichia stipites*+TX, *Pseudomonas aeruginosa*+TX, *Pseudomonas aureofasciens* (Spot-Less Biofungicide®)+TX, *Pseudomonas cepacia*+TX, *Pseudomonas chlororaphis* (AtEze®)+TX, *Pseudomonas corrugate*+TX, *Pseudomonas fluorescens* strain A506 (BlightBan A506®)+TX, *Pseudomonas putida*+TX, *Pseudomonas reactans*+TX, *Pseudomonas* spp.+TX, *Pseudomonas syringae* (Bio-Save®)+TX, *Pseudomonas viridiflava*+TX, *Pseudomons fluorescens* (Zequanox®)+TX, *Pseudozyma flocculosa* strain PF-A22 UL (Sporodex L®)+TX, *Puccinia canaliculata*+TX, *Puccinia thlaspeos* (Wood Warrior®)+TX, *Pythium paroecandrum*+TX, *Pythium oligandrum* (Polygandron®+TX, Polyversum®)+TX, *Pythium periplocum*+TX, *Rhanella aquatilis*+TX, *Rhanella* spp.+TX, *Rhizobia* (Dormal®+TX, Vault®)+TX, *Rhizoctonia*+TX, *Rhodococcus globerulus* strain AQ719+TX, *Rhodosporidium diobovatum*+TX, *Rhodosporidium toruloides*+TX, *Rhodotorula* spp.+TX, *Rhodotorula glutinis*+TX, *Rhodotorula graminis*+TX, *Rhodotorula mucilagnosa*+TX, *Rhodotorula rubra*+TX, *Saccharomyces cerevisiae*+TX, *Salinococcus roseus*+TX, *Sclerotinia minor*+TX, *Sclerotinia minor* (SARRITOR®)+TX, *Scytalidium* spp.+TX, *Scytalidium uredinicola*+TX, *Spodoptera exigua* nuclear polyhedrosis virus (Spod-X®+TX, Spexit®)+TX, *Serratia marcescens*+TX, *Serratia plymuthica*+TX, *Serratia* spp.+TX, *Sordaria fimicola*+TX, *Spodoptera littoralis* nucleopolyhedrovirus (Littovir®)+TX, *Sporobolomyces roseus*+TX, *Stenotrophomonas maltophilia*+TX, *Streptomyces ahygroscopicus*+TX, *Streptomyces albaduncus*+TX, *Streptomyces exfoliates*+TX, *Streptomyces galbus*+TX, *Streptomyces griseoplanus*+TX, *Streptomyces griseoviridis* (Mycostop®)+TX, *Streptomyces lydicus* (Actinovate®)+TX,

*Streptomyces lydicus* WYEC-108 (ActinoGrow®)+TX, *Streptomyces violaceus*+TX, *Tilletiopsis minor*+TX, *Tilletiopsis* spp.+TX, *Trichoderma asperellum* (T34 Biocontrol®)+TX, *Trichoderma gamsii* (Tenet®)+TX, *Trichoderma atroviride* (Plantmate®)+TX, *Trichoderma hamatum* TH 382+TX, *Trichoderma harzianum rifai* (Mycostar®)+TX, *Trichoderma harzianum* T-22 (Trianum-P®+TX, PlantShield HC®+TX, RootShield®+TX, Trianum-G®)+TX, *Trichoderma harzianum* T-39 (Trichodex®)+TX, *Trichoderma inhamatum*+TX, *Trichoderma koningii*+TX, *Trichoderma* spp. LC 52 (Sentinel®)+TX, *Trichoderma lignorum*+TX, *Trichoderma longibrachiatum*+TX, *Trichoderma polysporum* (Binab T®)+TX, *Trichoderma taxi*+TX, *Trichoderma virens*+TX, *Trichoderma virens* (formerly *Gliocladium virens* GL-21) (SoilGuard®)+TX, *Trichoderma viride*+TX, *Trichoderma viride* strain ICC 080 (Remedier®)+TX, *Trichosporon pullulans*+TX, *Trichosporon* spp.+TX, *Trichothecium* spp.+TX, *Trichothecium roseum*+TX, *Typhula phacorrhiza* strain 94670+TX, *Typhula phacorrhiza* strain 94671+TX, *Ulocladium atrum*+TX, *Ulocladium oudemansii* (Botry-Zen®)+TX, *Ustilago maydis*+TX, various bacteria and supplementary micronutrients (Natural II®)+TX, various fungi (Millennium Microbes®)+TX, *Verticillium chlamydosporium*+TX, *Verticillium lecanii* (Mycotal®+TX, Vertalec®)+TX, Vip3Aa20 (VIPtera®)+TX, *Virgibacillus marismortui*+TX, *Xanthomonas campestris* pv. Poae (Camperico®)+TX, *Xenorhabdus bovienii*+TX, *Xenorhabdus nematophilus*; and Plant extracts including: pine oil (Retenol®)+TX, azadirachtin (Plasma Neem Oil®+TX, AzaGuard®+TX, MeemAzal®+TX, Molt-X®+TX, Botanical IGR (Neemazad®+TX, Neemix®)+TX, canola oil (Lilly Miller Vegol®)+TX, *Chenopodium ambrosioides* near *ambrosioides* (Requiem®)+TX, *Chrysanthemum* extract (Crisant®)+TX, extract of neem oil (Trilogy®)+TX, essentials oils of Labiatae (Botania®)+TX, extracts of clove rosemary peppermint and thyme oil (Garden insect Killer®)+TX, Glycinebetaine (Greenstim®)+TX, garlic+TX, lemongrass oil (GreenMatch®)+TX, neem oil+TX, *Nepeta cataria* (Catnip oil)+TX, *Nepeta catarina*+TX, nicotine+TX, oregano oil (MossBuster®)+TX, Pedaliaceae oil (Nematon®)+TX, pyrethrum+TX, *Quillaja saponaria* (NemaQ®)+TX, *Reynoutria sachalinensis* (Regalia®+TX, Sakalia®)+TX, rotenone (Eco Roten®)+TX, Rutaceae plant extract (Soleo®)+TX, soybean oil (Ortho Ecosense®)+TX, tea tree oil (Timorex Gold®)+TX, thymus oil+TX, AGNIQUE® MMF+TX, BugOil®+TX, mixture of rosemary sesame pepermint thyme and cinnamon extracts (EF 300®)+TX, mixture of clove rosemary and peppermint extract (EF 400®)+TX, mixture of clove pepermint garlic oil and mint (Soil Shot®)+TX, kaolin (Screen®)+TX, storage glucam of brown algae (Laminarin®); and pheromones including: blackheaded fireworm pheromone (3M Sprayable Blackheaded Fireworm Pheromone®)+TX, Codling Moth Pheromone (Paramount dispenser-(CM)/Isomate C-Plus®)+TX, Grape Berry Moth Pheromone (3M MEC-GBM Sprayable Pheromone®)+TX, Leafroller pheromone (3M MEC—LR Sprayable Pheromone®)+TX, Muscamone (Snip7 Fly Bait®+TX, Starbar Premium Fly Bait®)+TX, Oriental Fruit Moth Pheromone (3M oriental fruit moth sprayable Pheromone®)+TX, Peachtree Borer Pheromone (Isomate-P®)+TX, Tomato Pinworm Pheromone (3M Sprayable Pheromone®)+TX, Entostat powder (extract from palm tree) (Exosex CM®)+TX, (E+TX,Z+TX, Z)-3+TX,8+TX,11 Tetradecatrienyl acetate+TX, (Z+TX,Z+TX,E)-7+TX,11+TX,13-Hexadecatrienal+TX, (E+TX,Z)-7+TX,9-Dodecadien-1-yl acetate+TX, 2-Methyl-1-butanol+TX, Calcium acetate+TX, Scenturion®+TX, Biolure®+TX, Check-Mate®+TX, Lavandulyl senecioate; and Macrobials including: *Aphelinus abdominalis*+TX, *Aphidius ervi* (Aphelinus-System®)+TX, *Acerophagus papaya*+TX, *Adalia bipunctata* (Adalia-System®)+TX, *Adalia bipunctata* (Adaline®)+TX, *Adalia bipunctata* (Aphidalia®)+TX, *Ageniaspis citricola*+TX, *Ageniaspis fuscicollis*+TX, *Amblyseius andersoni* (Anderline®+TX, Andersoni-System®)+TX, *Amblyseius californicus* (Amblyline®+TX, Spical®)+TX, *Amblyseius cucumeris* (Thripex®+TX, Bugline *cucumeris*®)+TX, *Amblyseius fallacis* (Fallacis®)+TX, *Amblyseius swirskii* (Bugline *swirskii*®+TX, *Swirskii*-Mite®)+TX, *Amblyseius womersleyi* (WomerMite®)+TX, *Amitus hesperidum*+TX, *Anagrus atomus*+TX, *Anagyrus fusciventris*+TX, *Anagyrus kamali*+TX, *Anagyrus loecki*+TX, *Anagyrus pseudococci* (Citripar®)+TX, *Anicetus benefices*+TX, *Anisopteromalus calandrae*+TX, *Anthocoris nemoralis* (Anthocoris-System®)+TX, *Aphelinus abdominalis* (Apheline®+TX, Aphiline®)+TX, *Aphelinus asychis*+TX, *Aphidius colemani* (Aphipar®)+TX, *Aphidius ervi* (Ervipar®)+TX, *Aphidius gifuensis*+TX, *Aphidius matricariae* (Aphipar-M®)+TX, *Aphidoletes aphidimyza* (Aphidend®)+TX, *Aphidoletes aphidimyza* (Aphidoline®)+TX, *Aphytis lingnanensis*+TX, *Aphytis melinus*+TX, *Aprostocetus hagenowii*+TX, *Atheta coriaria* (Staphyline®)+TX, *Bombus* spp.+TX, *Bombus terrestris* (Natupol Beehive®)+TX, *Bombus terrestris* (Beeline®+TX, Tripol®)+TX, *Cephalonomia stephanoderis*+TX, *Chilocorus nigritus*+TX, *Chrysoperla carnea* (Chrysoline®)+TX, *Chrysoperla carnea* (Chrysopa®)+TX, *Chrysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, *Cryptolaemus montrouzieri* (Cryptobug®+TX, Cryptoline®)+TX, *Cybocephalus nipponicus*+TX, *Dacnusa sibirica*+TX, *Dacnusa sibirica* (Minusa®)+TX, *Diglyphus isaea* (Diminex®)+TX, *Delphastus catalinae* (Delphastus®)+TX, *Delphastus pusillus*+TX, *Diachasmimorpha krausii*+TX, *Diachasmimorpha Iongicaudata*+TX, *Diaparsis jucunda*+TX, *Diaphorencyrtus aligarhensis*+TX, *Diglyphus isaea*+TX, *Diglyphus isaea* (Miglyphus®+TX, Digline®)+TX, *Dacnusa sibirica* (DacDigline®+TX, Minex®)+TX, *Diversinervus* spp.+TX, *Encarsia citrina*+TX, *Encarsia formosa* (Encarsia Max®+TX, Encarline®+TX, En-Strip®)+TX, *Eretmocerus eremicus* (Enermix®)+TX, *Encarsia guadeloupae*+TX, *Encarsia haitiensis*+TX, *Episyrphus balteatus* (Syrphidend®)+TX, *Eretmoceris siphonini*+TX, *Eretmocerus californicus*+TX, *Eretmocerus eremicus* (Ercal®+TX, Eretline e®)+TX, *Eretmocerus eremicus* (Bemimix®)+TX, *Eretmocerus hayati*+TX, *Eretmocerus mundus* (Bemipar®+TX, Eretline m®)+TX, *Eretmocerus siphonini*+TX, *Exochomus quadripustulatus*+TX, *Feltiella acarisuga* (Spidend®)+TX, *Feltiella acarisuga* (Feltiline®)+TX, *Fopius arisanus*+TX, *Fopius ceratitivorus*+TX, Formononetin (Wirless Beehome®)+TX, *Franklinothrips vespiformis* (Vespop®)+TX, *Galendromus occidentalis*+TX, *Goniozus legneri*+TX, *Habrobracon hebetor*+TX, *Harmonia axyridis* (HarmoBeetle®)+TX, *Heterorhabditis* spp. (Lawn Patrol®)+TX, *Heterorhabditis bacteriophora* (NemaShield HB®+TX, Nemaseek®+TX, Terranem-Nam®+TX, Terranem®+TX, Larvanem®+TX, B-Green®+TX, NemAttack®+TX, Nematop®)+TX, *Heterorhabditis* megidis (Nemasys H®+TX, BioNem H®+TX, Exhibitline hm®+TX, Larvanem-M®)+TX, *Hippodamia convergens*+TX, *Hypoaspis aculeifer* (Aculeifer-System®+TX, Entomite-A®)+TX, *Hypoaspis miles* (Hypoline m®+TX, Entomite-M®)+TX, *Lbalia leucospoides*+TX, *Lecanoideus floccissimus*+TX, *Lemophagus errabundus*+TX, *Leptomastidea abnormis*+TX, *Leptomastix dactylopii* (Leptopar®)+TX, *Leptomastix epona*+TX, *Lindorus lophanthae*+TX, *Lipolexis oregmae*+TX, *Lucilia caesar* (Natufly®)+TX, *Lysiphlebus testaceipes*+TX, *Macrolophus caliginosus* (Mirical-N®+TX, Macroline c®+TX, Mirical®)+TX, *Mesoseiulus longipes*+TX, *Metaphycus flavus*+TX, *Metaphycus lounsburyi*+TX, *Micromus angulatus* (Milacewing®)+TX, *Microterys flavus*+TX, *Muscidifurax raptorellus* and *Spalangia cameroni* (Biopar®)+TX, *Neodryinus typhlocybae*+TX, *Neoseiulus californicus*+TX, *Neoseiulus cucumeris* (THRYPEX®)+TX, *Neoseiulus fallacis*+TX, *Nesideocoris tenuis* (NesidioBug®+TX, Nesibug®)+TX, *Ophyra aenescens* (Biofly®)+TX, *Orius insidiosus* (Thripor-I®+TX, Oriline i®)+TX, *Orius laevigatus* (Thripor-L®+TX, Oriline I®)+TX, *Orius majusculus* (Oriline m®)+TX, *Orius strigicollis* (Thripor-S®)+TX, *Pauesia juniperorum*+TX, *Pediobius foveolatus*+TX, *Phasmarhabditis hermaphrodita* (Nemaslug®)+TX, *Phymastichus coffea*+TX, *Phytoseiulus macropilus*+TX, *Phytoseiulus persimilis* (Spidex®+TX, Phytoline p®)+TX, *Podisus maculiventris* (Podisus®)+TX, *Pseudacteon curvatus*+TX, *Pseudacteon obtusus*+TX, *Pseudacteon tricuspis*+TX, *Pseudaphycus maculipennis*+TX, *Pseudleptomastix mexicana*+TX, *Psyllaephagus pilosus*+TX, *Psyttalia concolor* (complex)+TX, *Quadrastichus* spp.+TX, *Rhyzobius lophanthae*+TX, *Rodolia cardinalis*+TX, *Rumina decollate*+TX, *Semielacher petiolatus*+TX, *Sitobion avenae* (Ervibank®)+TX, *Steinernema carpocapsae* (Nematac C®+TX, Millenium®+TX, BioNem C®+TX, NemAttack®+TX, Nemastar®+TX, Capsanem®)+TX, *Steinernema feltiae* (NemaShield®+TX, Nemasys F®+TX, BioNem F®+TX, *Steinernema*-System®+TX, NemAttack®+TX, Nemaplus®+TX, Exhibitline sf®+TX, Sciarid®+TX, Entonem®)+TX, *Steinernema kraussei* (Nemasys L®+TX, BioNem L®+TX, Exhibitline srb®)+TX, *Steinernema riobrave* (BioVector®+TX, BioVektor®)+TX, *Steinernema scapterisci* (Nematac S®)+TX, *Steinernema* spp.+TX, *Steinernematid* spp. (Guardian Nematodes®)+TX, *Stethorus punctillum* (Stethorus®)+TX, *Tamarixia radiate*+TX, *Tetrastichus setifer*+TX, *Thripobius semiluteus*+TX, *Torymus sinensis*+TX, *Trichogramma brassicae* (Tricholine b®)+TX, *Trichogramma brassicae* (Tricho-Strip®)+TX, *Trichogramma evanescens*+TX, *Trichogramma minutum*+TX, *Trichogramma ostriniae*+TX, *Trichogramma platneri*+TX, *Trichogramma pretiosum*+TX, *Xanthopimpla stemmator*; and other biologicals including: abscisic acid+TX, bioSea®+TX, *Chondrostereum purpureum* (Chontrol Paste®)+TX, *Colletotrichum gloeosporioides* (Collego®)+TX, Copper Octanoate (Cueva®)+TX, Delta traps (Trapline d®)+TX, *Erwinia amylovora* (Harpin) (ProAct®+TX, Ni-HIBIT Gold CST®)+TX, Ferri-phosphate (Ferramol®)+TX, Funnel traps (Trapline y®)+TX, Gallex®+TX, Grower's Secret®+TX, Homo-brassonolide+TX, Iron Phosphate (Lilly Miller Worry Free Ferramol Slug & Snail Bait®)+TX, MCP hail trap (Trapline f®)+TX, *Microctonus hyperodae*+TX, *Mycoleptodiscus terrestris* (Des-X®)+TX, BioGain®+TX, Aminomite®+TX, Zenox®+TX, Pheromone trap (Thripline ams®)+TX, potassium bicarbonate (MilStop®)+TX, potassium salts of fatty acids (Sanova®)+TX, potassium silicate solution (Sil-Matrix®)+TX, potassium iodide+potassium-thiocyanate (Enzicur®)+TX, SuffOil-X®+TX, Spider venom+TX, *Nosema locustae* (Semaspore Organic Grasshopper Control®)+TX, Sticky traps (Trapline YF®+TX, Rebell Amarillo®)+TX and Traps (Takitrapline y+b®)+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright © 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula I selected from Tables 1 to 9 and Table P with active ingredients described above comprises a compound selected from Tables 1 to 9 and Table P and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from Tables 1 to 9 and Table P and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Tables 1 to 9 and Table P and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula (I) can be carried out by any known methods, such as spraying or by dusting the seeds before sowing or during the sowing/planting of the seeds.

BIOLOGICAL EXAMPLES

Example B1: Activity Against *Plutella xylostella* (Diamond Back Moth)

24-well microtiter plates with artificial diet were treated with aqueous test solutions prepared from 10'000 ppm DMSO stock solutions by pipetting. After drying, the plates were infested with L2 larvae (10 to 15 per well). The samples were assessed for mortality and growth inhibition in comparison to untreated samples 5 days after infestation.

The following compounds gave an effect of at least 80% in at least one of the two categories (mortality or growth inhibition) at an application rate of 200 ppm: P1, P2, P3, P4, P5, P6, P7, P8, P9, P11, P12, P13, P14, P15, P16, P19, P22 and P23.

Example B2: Activity Against *Myzus persicae* (Green Peach Aphid)

Sunflower leaf discs were placed on agar in a 24-well microtiter plate and sprayed with aqueous test solutions prepared from 10'000 ppm DMSO stock solutions. After drying, the leaf discs were infested with an aphid population of mixed ages. The samples were assessed for mortality 6 days after infestation.

The following compounds resulted in at least 80% mortality at an application rate of 200 ppm: P1, P2, P3, P4, P5, P6, P7, P8, P9, P11, P12, P13, P14, P15, P16, P17, P18, P19, P20, P22 and P23.

Example B3: Activity Against *Myzus persicae* (Green Peach Aphid)

Roots of pea seedlings infested with an aphid population of mixed ages were placed directly in the aqueous test solutions prepared from 10'000 DMSO stock solutions. The samples were assessed for mortality 6 days after placing seedlings in test solutions.

The following compounds resulted in at least 80% mortality at a test rate of 24 ppm: P1, P2, P5, P6, P7, P8, P9, P11, P13, P14, P16, P19, P20, P21, P22 and P23.

Example B4: Activity Against *Frankliniella occidentalis* (Western Flower *Thrips*)

Sunflower leaf discs were placed on agar in 24-well microtiter plates and sprayed with aqueous test solutions prepared from 10'000 DMSO stock solutions. After drying the leaf discs were infested with a *Frankliniella* population of mixed ages. The samples were assessed for mortality 7 days after infestation.

The following compounds resulted in at least 80% mortality at an application rate of 200 ppm: P1, P2, P3, P5, P6, P7, P8, P9, P11, P12, P13, P16, P19, P20 and P22.

Example B5: Activity Against *Bemisia tabaci* (Cotton White Fly)

Cotton leaf discs were placed on agar in 24-well microtiter plates and sprayed with aqueous test solutions prepared from 10'000 ppm DMSO stock solutions. After drying the leaf discs were infested with adult white flies. The samples were checked for mortality 6 days after incubation.

The following compounds resulted in at least 80% mortality at an application rate of 200 ppm: P1, P2, P3, P4, P5, P6, P7, P8, P9, P11, P12, P13, P14, P16, P19, P21, P22 and P23.

Example B6: Activity Against *Euschistus heros* (Neotropical Brown Stink Bug)

Soybean leaf on agar in 24-well microtiter plates were sprayed with aqueous test solutions prepared from 10'000 ppm DMSO stock solutions. After drying the leaf were infested with N-2 nymphs. The samples were assessed for mortality and growth inhibition in comparison to untreated samples 5 days after infestation.

The following compounds gave an effect of at least 80% in at least one of the two categories (mortality or growth inhibition) at an application rate of 200 ppm: P1, P2, P3, P4, P5, P6, P7, P8, P9, P11, P12, P13, P14, P15, P16, P17, P18, P19, P20, P21, P22 and P23.

Example B7: Activity Against *Diabrotica* Balteata (Corn Root Worm)

Maize sprouts placed onto an agar layer in 24-well microtiter plates were treated with aqueous test solutions prepared from 10'000 ppm DMSO stock solutions by spraying. After drying, the plates were infested with L2 larvae (6 to 10 per well). The samples were assessed for mortality and growth inhibition in comparison to untreated samples 4 days after infestation.

The following compounds gave an effect of at least 80% in at least one of the two categories (mortality or growth inhibition) at an application rate of 200 ppm: P2, P3, P4, P7, P8, P9, P11, P12, P15, P16, P17, P18, P19 and P20.

Example B7: Activity Against *Spodoptera littoralis* (Egyptian Cotton Leaf Worm)

Cotton leaf discs were placed onto agar in 24-well microtiter plates and sprayed with aqueous test solutions prepared from 10'000 ppm DMSO stock solutions. After drying the leaf discs were infested with five L1 larvae. The samples were assessed for mortality, anti-feeding effect, and growth inhibition in comparison to untreated samples 3 days after infestation. Control of *Spodoptera littoralis* by a test sample is given when at least one of the categories mortality, anti-feedant effect, and growth inhibition is higher than the untreated sample.

The following compounds resulted in at least 80% control at an application rate of 200 ppm: P1, P2, P3, P4, P5, P7, P8, P9, P11, P12, P13, P16 and P22.

Example B7: Activity Against *Spodoptera littoralis* (Egyptian Cotton Leaf Worm)

Test compounds were applied by pipette from 10'000 ppm DMSO stock solutions into 24-well plates and mixed with agar. Lettuce seeds were placed onto the agar and the multi well plate was closed by another plate which contained also agar. After 7 days the compound was absorbed by the roots and the lettuce grew into the lid plate. The lettuce leaves were then cut off into the lid plate. *Spodoptera* eggs were pipetted through a plastic stencil onto a humid gel blotting paper and the lid plate was closed with it. The samples were assessed for mortality, anti-feedant effect and growth inhibition in comparison to untreated samples 6 days after infestation.

The following compounds gave an effect of at least 80% in at least one of the three categories (mortality, anti-feeding, or growth inhibition) at a test rate of 12.5 ppm: P3 and P7.

Example B7: Activity Against *Tetranychus urticae* (Two-Spotted Spider Mite)

Bean leaf discs on agar in 24-well microtiter plates were sprayed with aqueous test solutions prepared from 10'000 ppm DMSO stock solutions. After drying the leaf discs were infested with a mite population of mixed ages. The samples were assessed for mortality on mixed population (mobile stages) 8 days after infestation.

The following compounds resulted in at least 80% mortality at an application rate of 200 ppm: P2, P3, P4, P7, P11 and P23.

Example B7: Activity Against *Thrips tabaci* (Onion *Thrips*)

Sunflower leaf discs were placed on agar in 24-well microtiter plates and sprayed with aqueous test solutions prepared from 10'000 ppm DMSO stock solutions. After drying the leaf discs were infested with a *Thrips* population of mixed ages. The samples were assessed for mortality 6 days after infestation.

The following compounds resulted in at least 80% mortality at an application rate of 200 ppm: P2 and P9.

The invention claimed is:
1. A compound of formula I

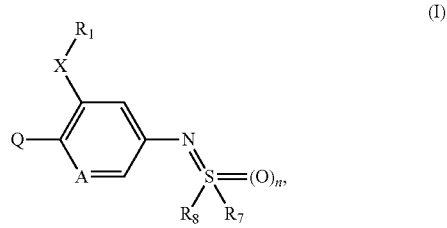

wherein
A is CH or N;
X is S, SO or SO$_2$;

$R_1$ is $C_1$-$C_4$alkyl, $C_1$-$C_4$haloalkyl or $C_3$-$C_6$cycloalkyl-$C_1$-$C_4$alkyl;

$R_7$ and $R_8$ are, independently from each other, $C_1$-$C_6$alkyl, $C_1$-$C_6$haloalkyl, $C_3$-$C_6$cycloalkyl, $C_1$-$C_6$cyanoalkyl, $C_1$-$C_4$alkoxy$C_1$-$C_4$alkyl, pyridyl or phenyl, wherein said pyridyl or phenyl can be mono- or polysubstituted by substituents selected from the group consisting of halogen, cyano, $C_1$-$C_4$alkyl, $C_1$-$C_4$haloalkyl, $C_1$-$C_4$haloalkoxy, $C_1$-$C_4$alkoxy, $C_1$-$C_4$haloalkylsulfanyl, $C_1$-$C_4$haloalkylsulfinyl, $C_1$-$C_4$haloalkylsulfonyl and —C(O)$C_1$-$C_4$haloalkyl; or $R_7$ and $R_8$, together with the sulfur atom to which they are attached, form a four- to six-membered, saturated ring system, said ring system can be mono- or polysubstituted by substituents selected from the group consisting of halogen, cyano, $C_1$-$C_4$alkyl, $C_1$-$C_4$alkoxy and $C_1$-$C_4$haloalkyl; and said ring system may contain one heteroatom selected from the group consisting of nitrogen, oxygen and sulfur;

n is 0 or 1;

Q is a radical selected from the group consisting of formula $Q_1$ to $Q_3$

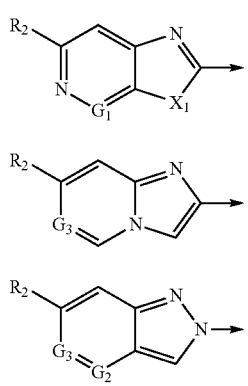

wherein the arrow denotes the point of attachment to the ring incorporating the radical A;
and wherein
$X_1$ is O, S or $NR_3$, wherein $R_3$ is $C_1$-$C_4$alkyl;
$R_2$ is halogen, $C_1$-$C_6$haloalkyl, $C_1$-$C_4$haloalkylsulfanyl, $C_1$-$C_4$haloalkylsulfinyl, $C_1$-$C_4$haloalkylsulfonyl or $C_1$-$C_6$haloalkoxy;
$G_1$ is N or CH;
$G_2$ and $G_3$ are, independently from each other, N or CH; and agrochemically acceptable salts, stereoisomers, enantiomers, tautomers and N-oxides of the compounds of formula I.

2. The compound of claim 1,
wherein
$R_1$ is methyl, ethyl, n-propyl, i-propyl or cyclopropylmethyl.

3. The compound of claim 1,
wherein
Q is $Q_1$; and
$R_2$ is methyl, ethyl, n-propyl, i-propyl or cyclopropylmethyl.

4. The compound of claim 1,
wherein
Q is $Q_1$;
$X_1$ is $NR_3$, and $R_3$ is methyl;

X is $SO_2$;
$R_1$ is ethyl;
A is CH or N;
$R_2$ is $C_1$-$C_6$haloalkyl;
$G_1$ is N or CH;
n is 0 or 1; and
$R_7$ and $R_8$ are, independently from each other, $C_1$-$C_6$alkyl, $C_3$-$C_6$cycloalkyl or phenyl monosubstituted by $C_1$-$C_4$alkyl, or
$R_7$ and $R_8$, together with the sulfur atom to which they are attached, form a four- to six-membered, saturated ring system which can contain one oxygen atom.

5. The compound of claim 1,
wherein
Q is $Q_2$; and
$R_1$ is methyl, ethyl, n-propyl, i-propyl or cyclopropylmethyl.

6. The compound of claim 1,
wherein
Q is $Q_2$;
X is $SO_2$;
$R_1$ is ethyl;
A is CH or N;
$R_2$ is $C_1$-$C_6$haloalkyl;
$G_3$ is N or CH;
n is 0 or 1; and
$R_7$ and $R_8$ are, independently from each other, $C_1$-$C_6$alkyl, $C_3$-$C_6$cycloalkyl or phenyl monosubstituted by $C_1$-$C_4$alkyl; or
$R_7$ and $R_8$, together with the sulfur atom to which they are attached, form a four- to six-membered, saturated ring system, and said ring system can contain one oxygen atom.

7. The compound of claim 1,
wherein
X is $SO_2$;
$R_1$ is ethyl;
A is CH or N;
n is 0 or 1;
$R_7$ and $R_8$ are, independently from each other, $C_1$-$C_6$alkyl, $C_3$-$C_6$cycloalkyl or phenyl monosubstituted by $C_1$-$C_4$alkyl; or
$R_7$ and $R_8$, together with the sulfur atom to which they are attached, form a four- to six-membered, saturated ring system, and said ring system can contain one oxygen atom; and
Q is a radical selected from the group consisting of formula $Q_{1a}$, $Q_{1b}$, $Q_{2a}$ and $Q_{3a}$

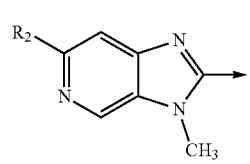

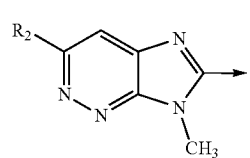

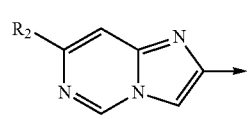

-continued

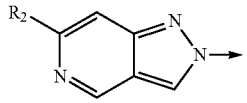

wherein the arrow denotes the point of attachment to the ring incorporating the radical A; and $R_2$ is $C_1$-$C_6$haloalkyl.

8. The compound of claim 1, wherein

Q is $Q_3$; and $R_1$ is methyl, ethyl, n-propyl, i-propyl or cyclopropylmethyl.

9. The compound of claim 1, wherein

Q is $Q_2$;

X is $SO_2$;

$R_1$ is ethyl;

A is CH or N;

$R_2$ is $C_1$-$C_6$haloalkyl;

$G_2$ is CH;

$G_3$ is N or CH;

n is 0 or 1; and $R_7$ and $R_8$ are, independently from each other, $C_1$-$C_6$alkyl, $C_3$-$C_6$cycloalkyl or phenyl which phenyl is monosubstituted by $C_1$-$C_4$alkyl; or $R_7$ and $R_8$, together with the sulfur atom to which they are attached, form a four- to six-membered, saturated ring system, and said ring system can contain one oxygen atom.

10. A pesticidal composition, which comprises a compound of formula I according to claim 1 or, where appropriate, a tautomer thereof, in free form or in agrochemically utilizable salt form, as active ingredient and at least one auxiliary.

11. A method for controlling pests, which comprises applying a composition according to claim 10 to the pests or their environment with the exception of a method for treatment of the human or animal body by surgery or therapy and diagnostic methods practiced on the human or animal body.

12. A method for the protection of plant propagation material from the attack by pests, which comprises treating the propagation material or the site, where the propagation material is planted, with a composition according to claim 10.

13. A process for the preparation of a compound of formula (XI-A)

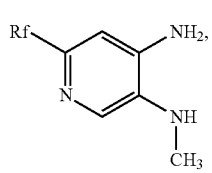

(XI-A)

or a salt thereof; wherein Rf is $C_1$-$C_6$haloalkyl; comprising a. reacting a compound of formula 14

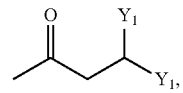

14 wherein $Y_1$ is independently halogen or $C_1$-$C_4$-alkoxy; or the two radicals $Y_1$ in a compound of formula 14 together form a group —O—$(CH_2)_m$—O—, wherein m is 2, 3 or 4; with a compound of formula 15

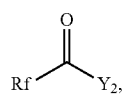

15 wherein Rf is $C_1$-$C_6$haloalkyl; and $Y_2$ is $C_1$-$C_6$alkoxy, chloro, fluoro or $C_1$-$C_6$dialkylamino; in the presence of a base to produce a compound of formula 16

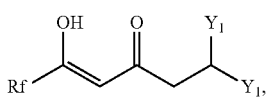

16 or a salt thereof; or tautomers and E/Z isomers thereof; wherein Rf is $C_1$-$C_6$haloalkyl; and $Y_1$ is independently halogen or $C_1$-$C_4$-alkoxy; or the two radicals $Y_1$ in a compound of formula 16 together form a group —O—$(CH_2)_m$—O—, wherein m is 2, 3 or 4; and b. reacting a compound of formula 16

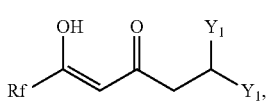

16 or a salt thereof;

or tautomers and E/Z isomers thereof; wherein Rf is $C_1$-$C_6$haloalkyl; and $Y_1$ is independently halogen or $C_1$-$C_4$-alkoxy; or the two radicals $Y_1$ in a compound of formula 16 together form a group —O—$(CH_2)_m$—O—, wherein m is 2, 3 or 4;

with ammonia, or a salt thereof; to produce a compound of formula 17

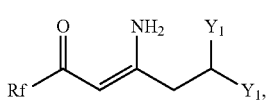

17 or tautomers and E/Z isomers thereof; wherein Rf is $C_1$-$C_6$haloalkyl; and $Y_1$ is independently halogen or $C_1$-$C_4$-alkoxy; or the two radicals $Y_1$ in a compound of formula 17 together form a group —O—$(CH_2)_m$—O—, in which m is 2, 3 or 4; and c. reacting a compound of formula 17

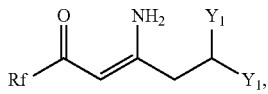

or tautomers and E/Z isomers thereof; wherein Rf is $C_1$-$C_6$haloalkyl; and $Y_1$ is independently halogen or $C_1$-$C_4$-alkoxy; or the two radicals $Y_1$ in a compound of formula 17 together form a group —O—$(CH_2)_m$—O—, in which m is 2, 3 or 4;

with an ammonium salt; in the presence of an acid to produce a compound of formula 10

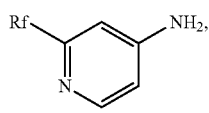

or a salt thereof; wherein Rf is $C_1$-$C_6$haloalkyl; and d. reacting a compound of formula 10

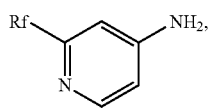

or a salt thereof; wherein Rf is $C_1$-$C_6$haloalkyl; with a halogenating agent;

to produce a compound of formula 11

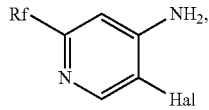

or a salt thereof; wherein Rf is $C_1$-$C_6$haloalkyl; and Hal is a halogen; and e. reacting a compound of formula 11

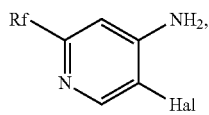

or a salt thereof; wherein Rf is $C_1$-$C_6$haloalkyl; and Hal is a halogen; with methylamine, or a salt thereof; to produce the compound of formula (XI-A)

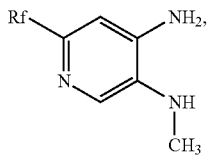

or a salt thereof; wherein Rf is $C_1$-$C_6$haloalkyl.

14. A process for the preparation of a compound of formula 10 according to claim 13 comprising b1. reacting a compound of formula 16

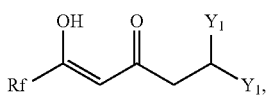

or a salt thereof;

or tautomers and E/Z isomers thereof; wherein Rf is $C_1$-$C_6$haloalkyl; and $Y_1$ is independently halogen or $C_1$-$C_4$-alkoxy; or the two radicals $Y_1$ in a compound of formula 16 together form a group —O—$(CH_2)_m$—O—, wherein m is 2, 3 or 4; with ammonia, or a salt thereof; to produce a reaction mixture comprising a compound of formula 17

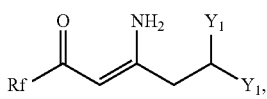

or tautomers and E/Z isomers thereof; wherein Rf is $C_1$-$C_6$haloalkyl; and $Y_1$ is independently halogen or $C_1$-$C_4$-alkoxy; or the two radicals $Y_1$ in a compound of formula 17 together form a group —O—$(CH_2)_m$—O—, wherein m is 2, 3 or 4; and b2. reacting said mixture directly with an ammonium salt; in the presence of an acid to produce the compound of formula 10

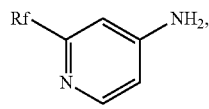

or a salt thereof; wherein Rf is $C_1$-$C_6$haloalkyl.

15. A compound of the formula 17

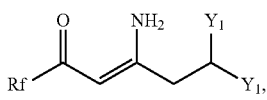

or tautomers and E/Z isomers thereof; wherein Rf is $C_1$-$C_6$haloalkyl; and $Y_1$ is independently halogen or $C_1$-$C_4$-alkoxy; or
the two radicals $Y_1$ in a compound of formula 17 together form a group —O—$(CH_2)_m$—O—, in which m is 2, 3 or 4.
16. The compound of claim 15, wherein
wherein Rf is $CF_3$.
17. The compound of claim 16, wherein the compound is
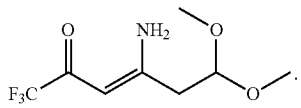
18. A compound, wherein the compound is selected from the group consisting of
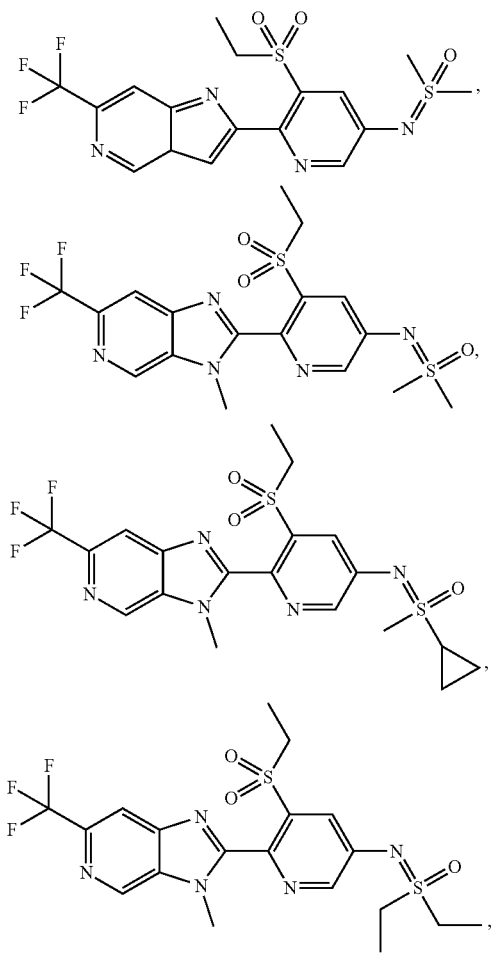
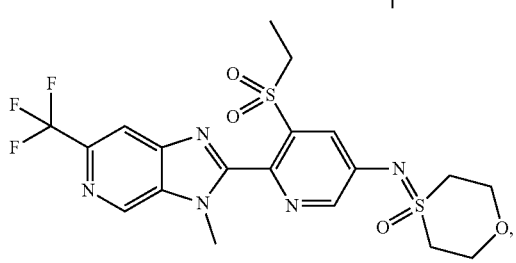
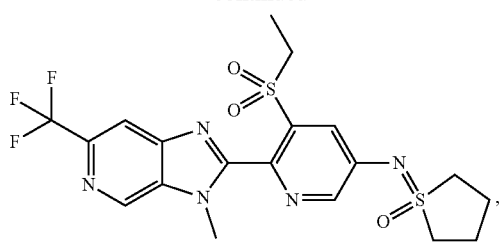
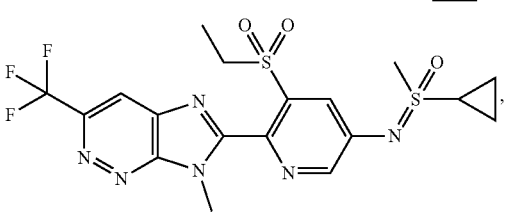
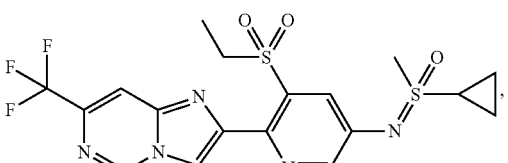
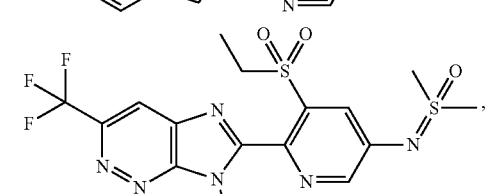
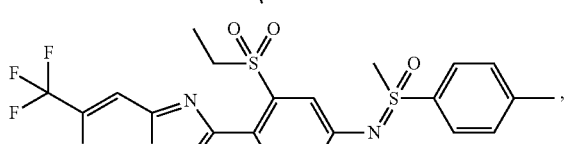
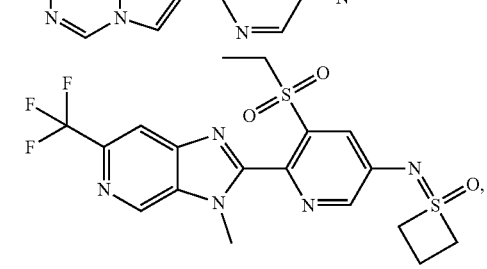
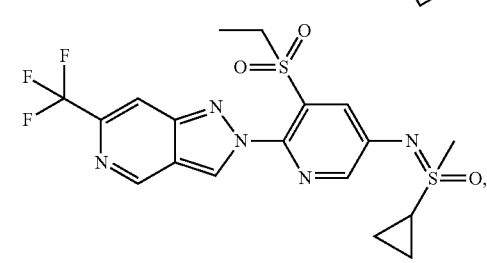
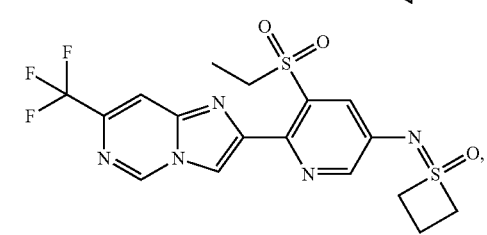

-continued
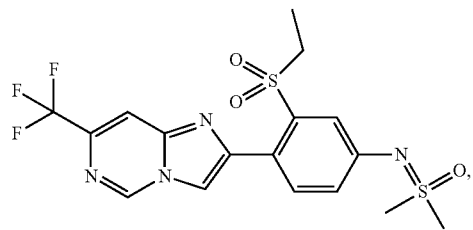
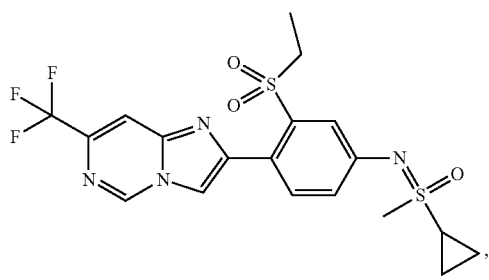
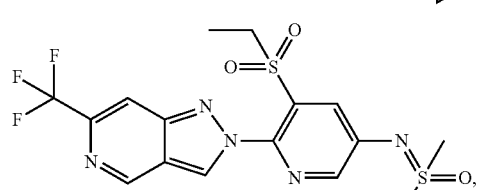
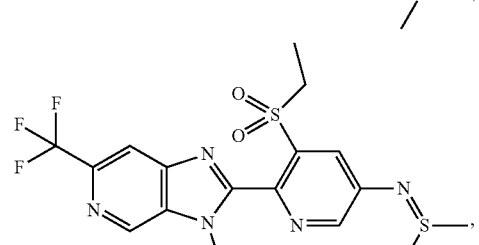
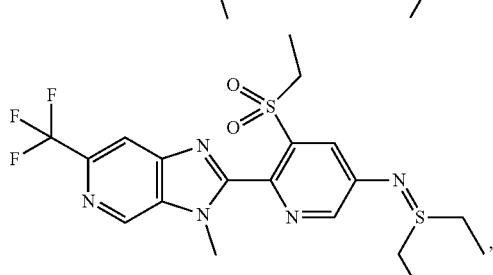
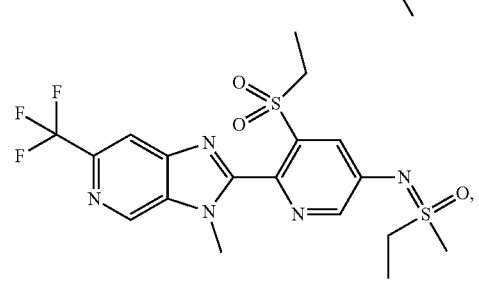
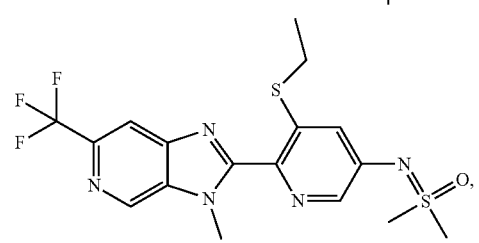
-continued
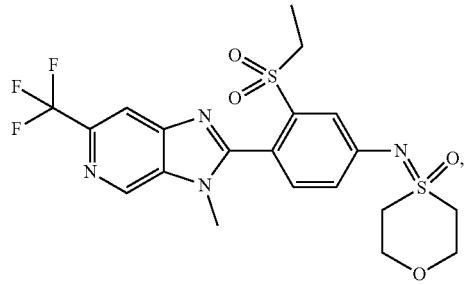
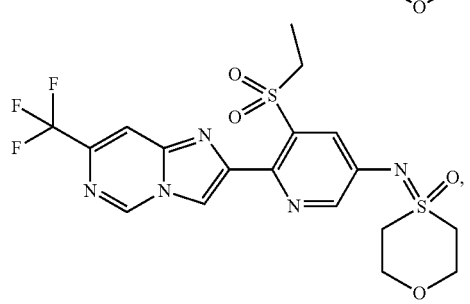
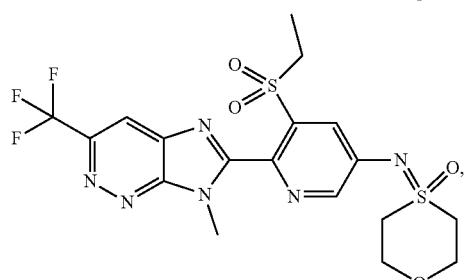
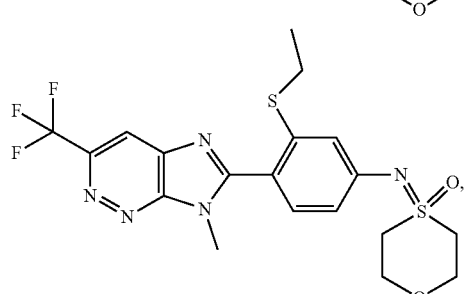
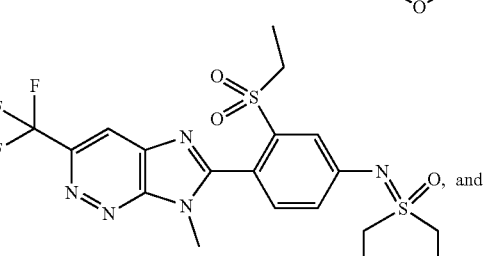, and
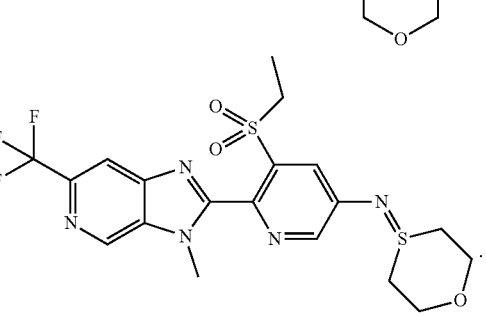.

19. The compound of claim 18, wherein the compound is selected from the group consisting of
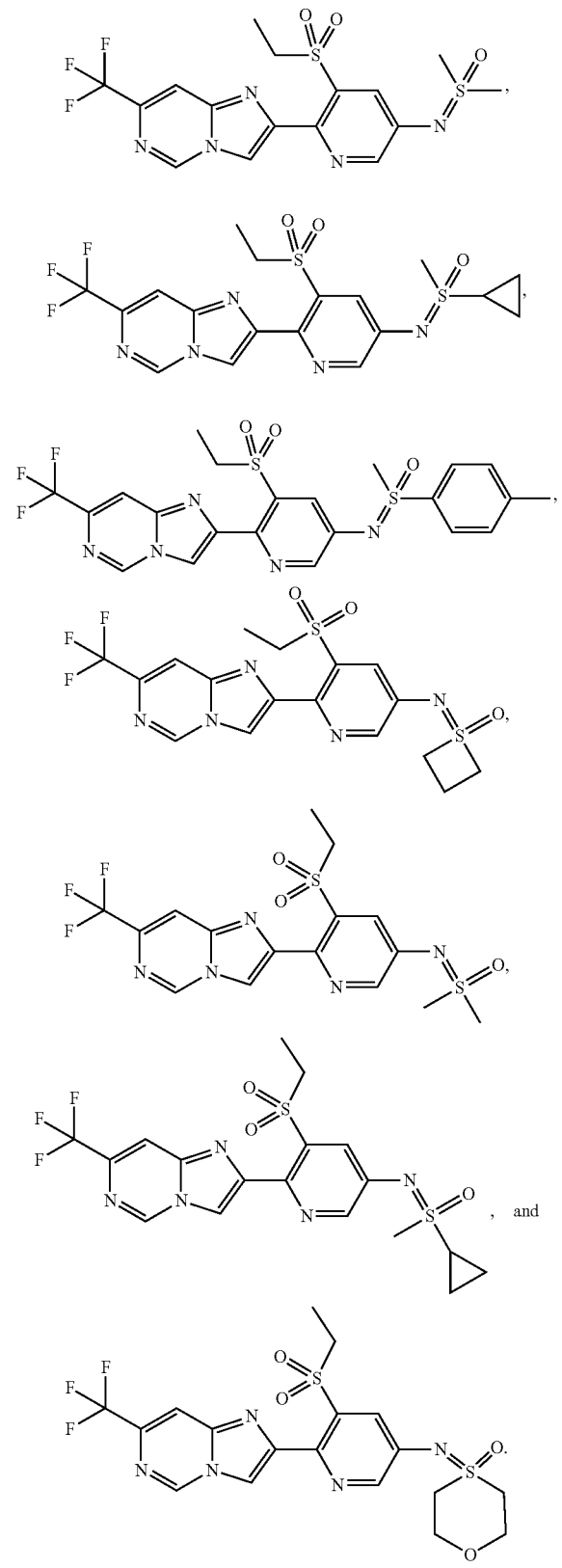
20. The compound of claim 18, wherein the compound is selected from the group consisting of
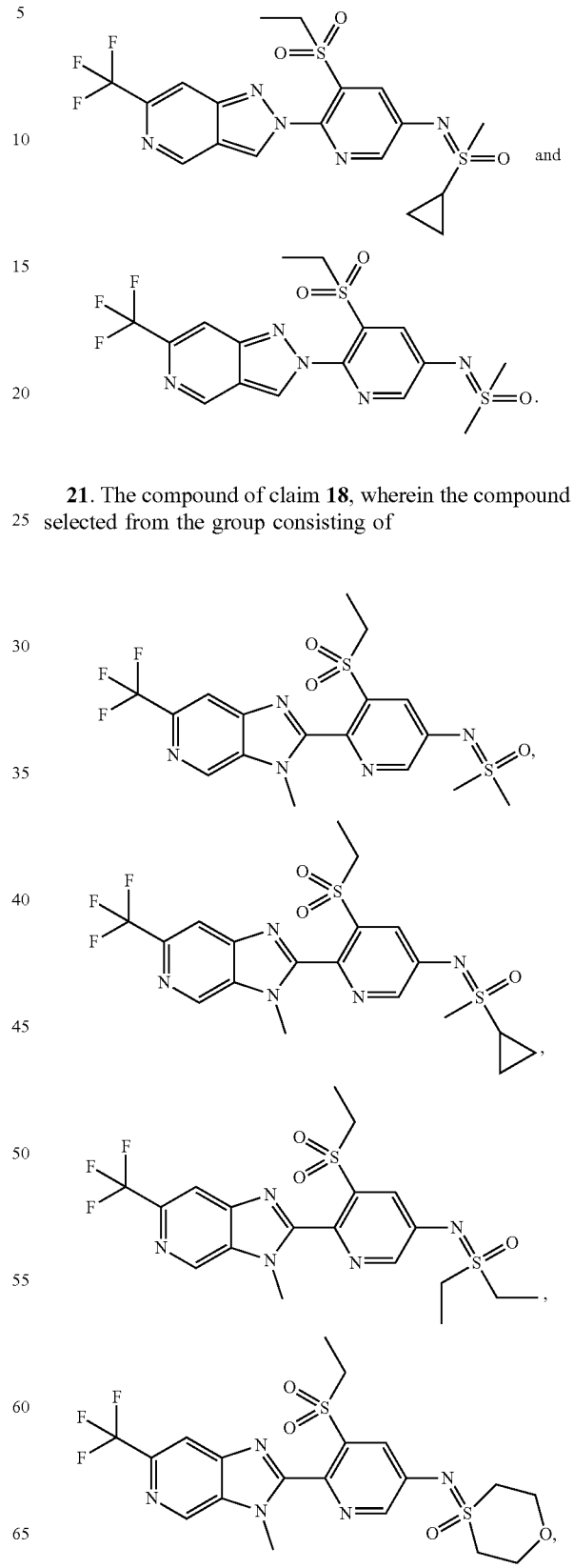
21. The compound of claim 18, wherein the compound is selected from the group consisting of

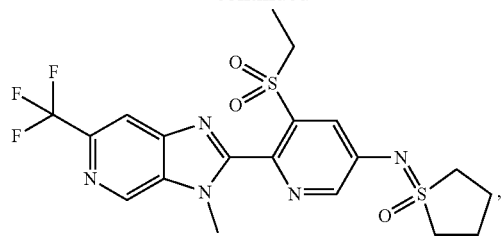
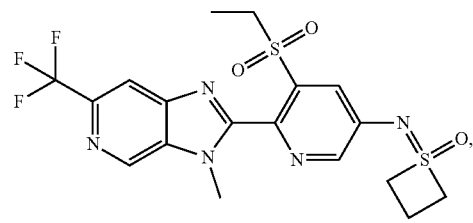
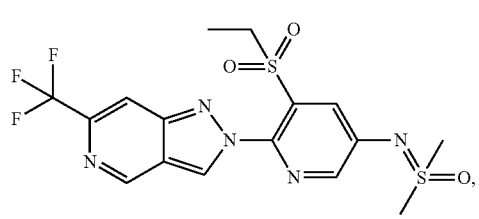
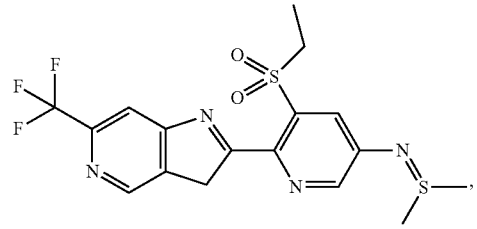
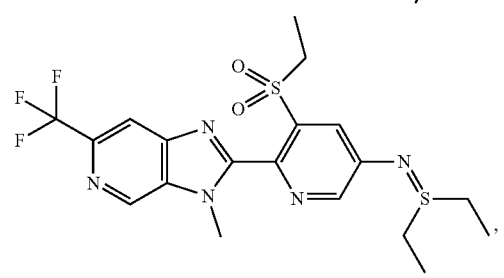
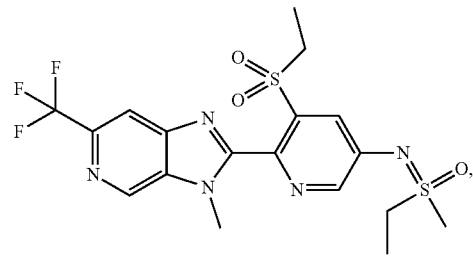
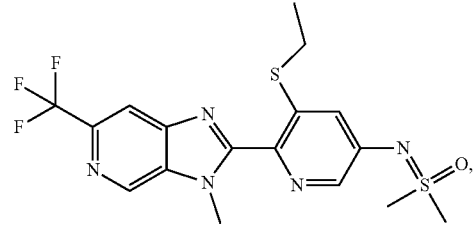
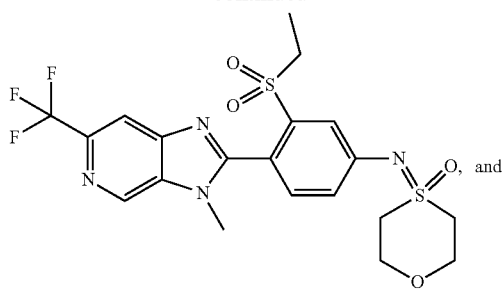, and
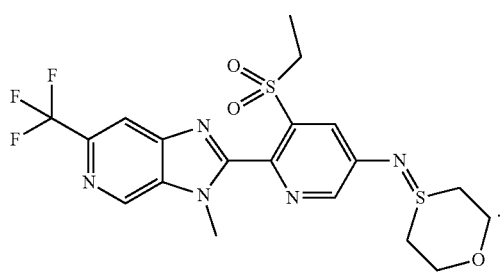;
22. The compound of claim 18, wherein the compound is selected from the group consisting of
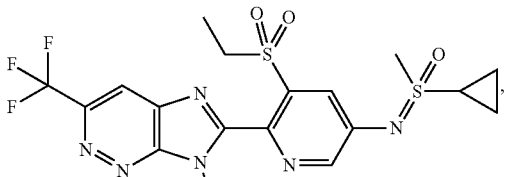
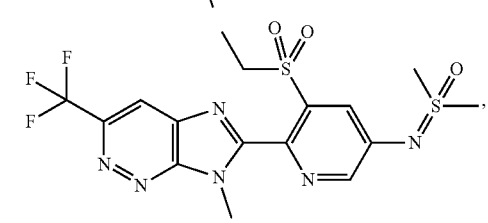
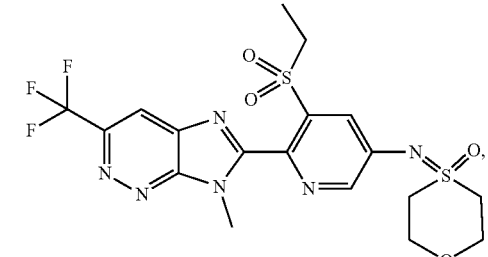
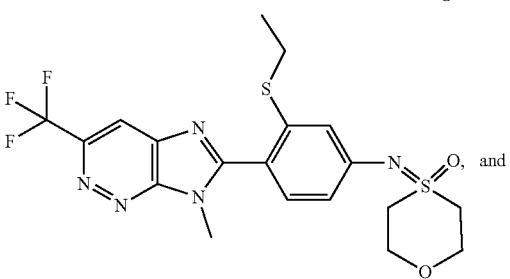, and

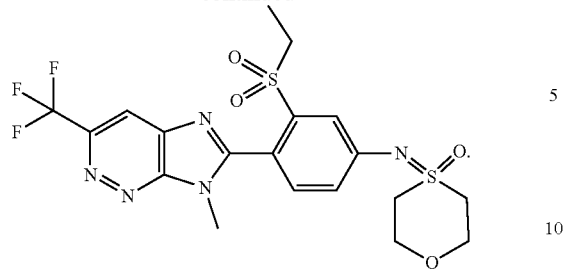
* * * * *